US012575887B2

(12) United States Patent
Metcalfe et al.

(10) Patent No.: US 12,575,887 B2
(45) Date of Patent: Mar. 17, 2026

(54) SURGICAL SYSTEMS, ANATOMICAL MODELS AND ASSOCIATED METHODS

(71) Applicant: ARTHREX, INC., Naples, FL (US)

(72) Inventors: Nick Metcalfe, Bonita Springs, FL (US); Michael Moreland, Fort Myers, FL (US); Aaron Jerome Hewitt, Naples, FL (US); Michael Charles Morris, Naples, FL (US); George Rego, Fort Myers, FL (US); Gianna Christine Vega-Soto, Naples, FL (US); Timothy J. Thompson, Naples, FL (US)

(73) Assignee: ARTHREX, INC., Naples, FL (US)

( * ) Notice: Subject to any disclaimer, the term of this patent is extended or adjusted under 35 U.S.C. 154(b) by 804 days.

(21) Appl. No.: 17/961,913

(22) Filed: Oct. 7, 2022

(65) Prior Publication Data

US 2023/0111376 A1     Apr. 13, 2023

Related U.S. Application Data

(60) Provisional application No. 63/253,290, filed on Oct. 7, 2021.

(51) Int. Cl.
*A61B 34/10* (2016.01)
*G09B 23/30* (2006.01)

(52) U.S. Cl.
CPC .............. *A61B 34/10* (2016.02); *G09B 23/30* (2013.01); *A61B 2034/105* (2016.02)

(58) Field of Classification Search
None
See application file for complete search history.

(56) References Cited

U.S. PATENT DOCUMENTS

| | | | |
|---|---|---|---|
| 6,471,519 | B1 | 10/2002 | Biermann et al. |
| 7,699,615 | B2 | 4/2010 | Sakezles |
| 7,780,451 | B2 | 8/2010 | Willobee et al. |
| 7,857,626 | B2 | 12/2010 | Toly |
| 8,210,852 | B2 | 7/2012 | Miller et al. |
| 8,425,234 | B2 | 4/2013 | Sakezles |
| 8,568,148 | B2 | 10/2013 | Miller et al. |
| 8,843,229 | B2 | 9/2014 | Vanasse et al. |
| 9,741,263 | B2 | 8/2017 | Iannotti et al. |
| 9,805,624 | B2 | 10/2017 | Reihsen et al. |

(Continued)

FOREIGN PATENT DOCUMENTS

| | | |
|---|---|---|
| EP | 3536354 | 9/2019 |
| WO | 2015089118 | 6/2015 |

(Continued)

OTHER PUBLICATIONS

Rader, PhD, S.R. 3D printing of patient specific anatomical models. Stratasys. Retrieved from: https://www.fda.gov/media/107510/download.

(Continued)

*Primary Examiner* — Andrew H Lam

(74) *Attorney, Agent, or Firm* — Carlson, Gaskey & Olds, P.C.

(57) ABSTRACT

This disclosure relates to surgical systems, devices and methods for planning and implementing surgical procedures. The systems and methods disclosed herein may be utilized to establish physical models of anatomy.

19 Claims, 34 Drawing Sheets

(56) References Cited

U.S. PATENT DOCUMENTS

| | | | |
|---|---|---|---|
| 10,553,130 B2 | 2/2020 | Poniatowski et al. | |
| 10,588,752 B2 | 3/2020 | Winslow et al. | |
| 10,973,535 B2 | 4/2021 | Iannotti et al. | |
| 11,033,336 B2 | 6/2021 | Bohl | |
| 11,403,966 B2 | 8/2022 | Tatum et al. | |
| 11,443,654 B2 | 9/2022 | Grant et al. | |
| 11,450,237 B2 | 9/2022 | Grant et al. | |
| 11,850,002 B2 | 12/2023 | Walach et al. | |
| 2013/0085590 A1 | 4/2013 | Byran et al. | |
| 2014/0272881 A1 | 9/2014 | Barsoum | |
| 2017/0249440 A1 | 8/2017 | Lang et al. | |
| 2017/0296205 A1 | 10/2017 | Iannotti et al. | |
| 2019/0142520 A1 | 5/2019 | VanDyken | |
| 2019/0220974 A1 | 7/2019 | Mathaneswaran et al. | |
| 2019/0239973 A9 | 8/2019 | Esterberg et al. | |
| 2020/0015893 A1 | 1/2020 | Walach | |
| 2021/0196290 A1 | 7/2021 | Iannotti et al. | |
| 2021/0233429 A1 | 7/2021 | Barber et al. | |
| 2021/0241656 A1 | 8/2021 | Barber et al. | |
| 2021/0244474 A1 | 8/2021 | Barber et al. | |
| 2021/0280087 A1 | 9/2021 | Logan | |
| 2022/0270517 A1 | 8/2022 | Fink et al. | |

FOREIGN PATENT DOCUMENTS

| | | | |
|---|---|---|---|
| WO | 2019158470 | 8/2019 | |
| WO | 2020123706 | 6/2020 | |
| WO | WO-2020123706 A1 * | 6/2020 | ............ G06N 3/045 |
| WO | 2020163358 | 8/2020 | |
| WO | 2020231654 | 11/2020 | |
| WO | 2021127410 | 6/2021 | |
| WO | 2021237367 | 12/2021 | |
| WO | 2022152681 | 7/2022 | |

OTHER PUBLICATIONS

Paramasivam, V., Sindhu, Singh, G., Santhanakrishnan, S. (2020). 3D printing of human anatomical models for preoperative surgical planning. ScienceDirect. Procedia Manufacturing 48. pp. 684-690.

Monash University revolutionizes human anatomy study. 3D Systems. Retrieved from: https://www.3dsystems.com/learning-center/case-studies/3d-printed-cadavers-monash-university-poised-revolutionize-human.

International Search Report and Written Opinion for International Application No. PCT/US2022/046041 filed Nov. 25, 2022.

International Preliminary Report on Patentability for International Application No. PCT/US2022/046041 mailed Apr. 18, 2024.

* cited by examiner

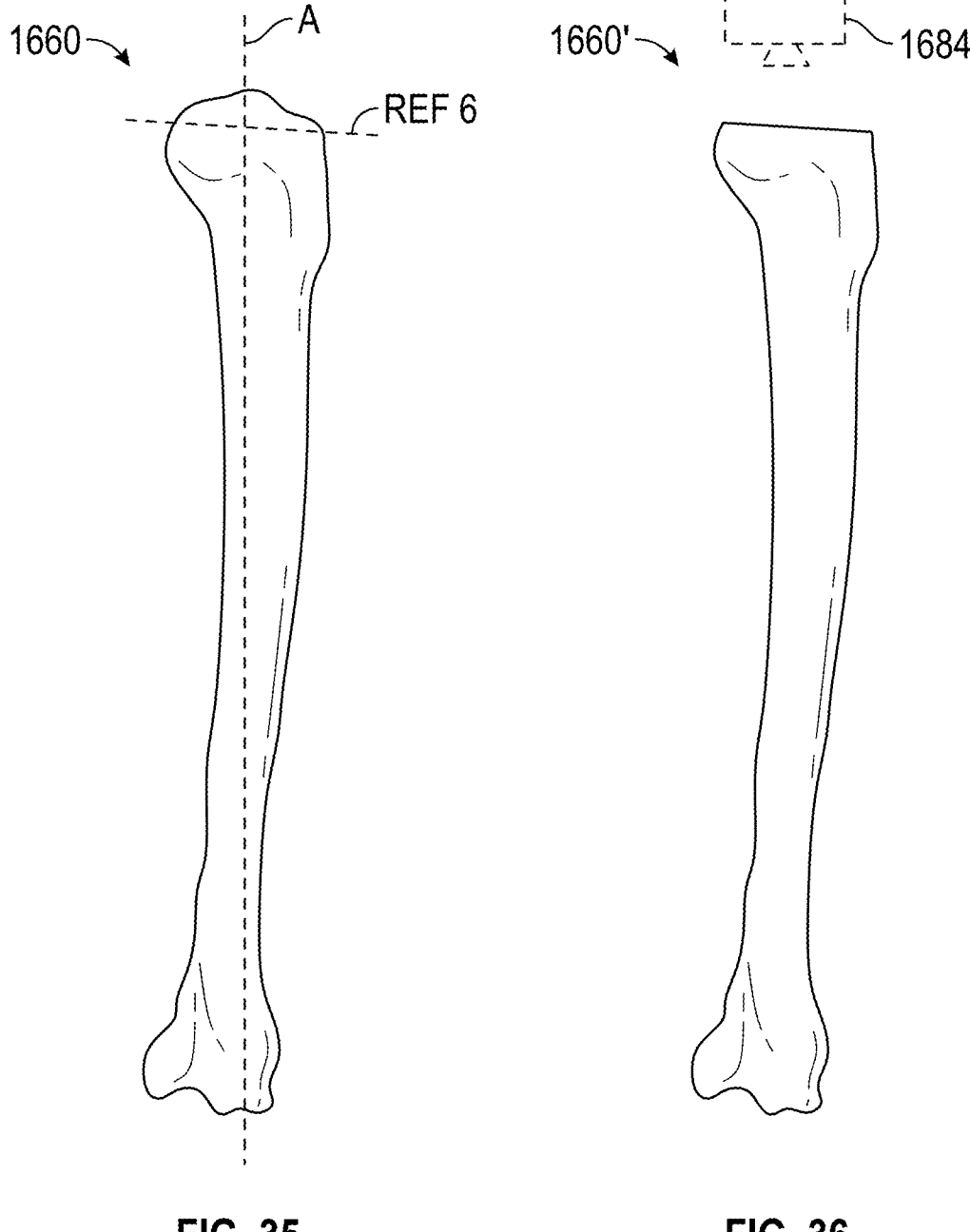
FIG. 35          FIG. 36

SURGICAL SYSTEMS, ANATOMICAL MODELS AND ASSOCIATED METHODS

CROSS-REFERENCE TO RELATED APPLICATION

The present disclosure claims priority to U.S. Provisional Application No. 63/253,290 filed Oct. 7, 2021.

BACKGROUND

This disclosure relates to surgical systems, devices and methods for planning and implementing surgical procedures utilizing physical models of anatomy.

Many bones of the human musculoskeletal system include articular surfaces. The articular surfaces articulate relative to other bones to facilitate different types and degrees of joint movement. The articular surfaces may erode (e.g., experience bone loss) over time due to repeated use or wear or can fracture as a result of a traumatic impact. These types of bone defects can cause joint instability and pain.

Surgeons may prepare for an orthopaedic surgery by performing a procedure on a cadaveric or saw bone specimen.

SUMMARY

This disclosure relates to systems, devices and methods of performing a surgical procedure. The systems may be utilized for performing one or more surgical procedures on physical models representative of anatomy.

A physical anatomical model according to an implementation of the present disclosure includes, inter alia, a main body including a target zone and one or more warning zones adjacent to the target zone that may cooperate to establish a construction representative of an anatomy. The target zone may have a property associated with a respective portion of the anatomy. Each warning zone may have a property that may differ from a natural property of a respective portion of the anatomy and that may differ from the property of the target zone.

A physical anatomical model according to an implementation of the present disclosure includes, inter alia, a main body that may include a target zone and one or more warning zones adjacent to the target zone that may cooperate to establish a construction representative of an anatomy. The target zone may have a color that may correspond to a natural color of a respective portion of the anatomy. Each warning zone may have a respective artificial color that may differ from a natural color of a respective portion of the anatomy and that may establish a visual contrast with the natural color associated with the target zone.

A training device for a surgical procedure according to an implementation of the present disclosure includes, inter alia, a physical anatomical model including a main body representative of an anatomy and an indication member embedded in the main body. The indication member may be representative of a nerve of the anatomy. The indication member may be configured to generate an indicator in response to meeting a predetermined criterion.

A training assembly for a surgical procedure according to an implementation of the present disclosure includes, inter alia, a physical anatomical model including a main body that may have a construction representative of an anatomy. The main body may extend between a first end portion and a second end portion. A measurement device may include a base, a tower and an outrigger. The tower may extend in a first direction from the base. The outrigger may extend laterally from the tower. The outrigger may include a ruler that may be situated over a predetermined position along the base. The base may be dimensioned to support a resected surface along the first end portion of the main body at the predetermined position such that an indicator along the second end portion of the main body may be aligned with a position along ruler. Each position along the ruler may be associated with a respective angle relative an axis. The axis may extend in the first direction from the predetermined position.

A system for rehearsing a surgical procedure according to an implementation of the present disclosure includes, inter alia, a computing device including a processor coupled to memory. The processor may be configured to access a virtual anatomical model from the memory in response to selecting one or more parameters in a graphical user interface. The virtual anatomical model may be associated with an anatomy. The processor may be configured to cause the virtual anatomical model to be displayed in the graphical user interface. The processor may be configured to generate a configuration associated with a physical anatomical model that may be representative of the virtual anatomical model.

A method of rehearsing for a surgical procedure according to an implementation of the present disclosure includes, inter alia, defining a virtual anatomical model associated with an anatomy and forming a plurality of layers of material to establish a physical anatomical model that may be representative of the virtual anatomical model. The layers of material may establish a target zone and one or more warning zones that may bound the target zone. The target zone may have a color that may correspond to a natural color of a respective portion of the anatomy. Each warning zone may have a respective artificial color that may establish a visual contrast with the natural color associated with the target zone.

The present disclosure may include any one or more of the individual features disclosed above and/or below alone or in any combination thereof.

The various features and advantages of this disclosure will become apparent to those skilled in the art from the following detailed description. The drawings that accompany the detailed description can be briefly described as follows.

US 12,575,887 B2

3

Figure 10:
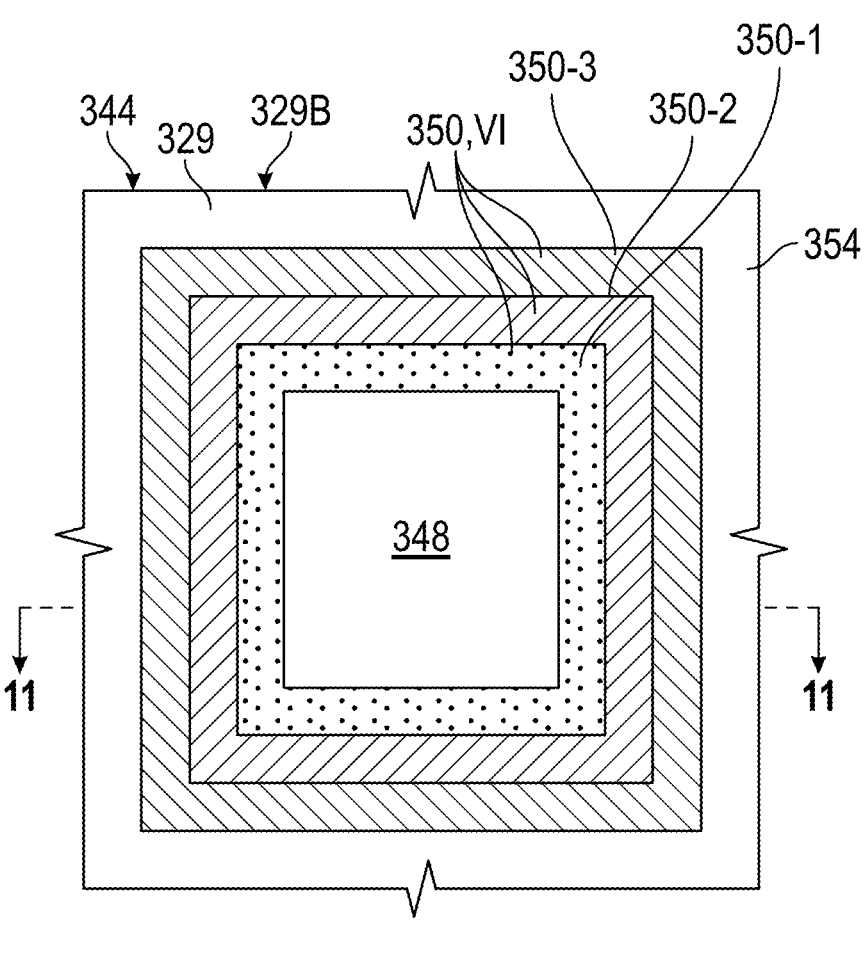
Figure 11:
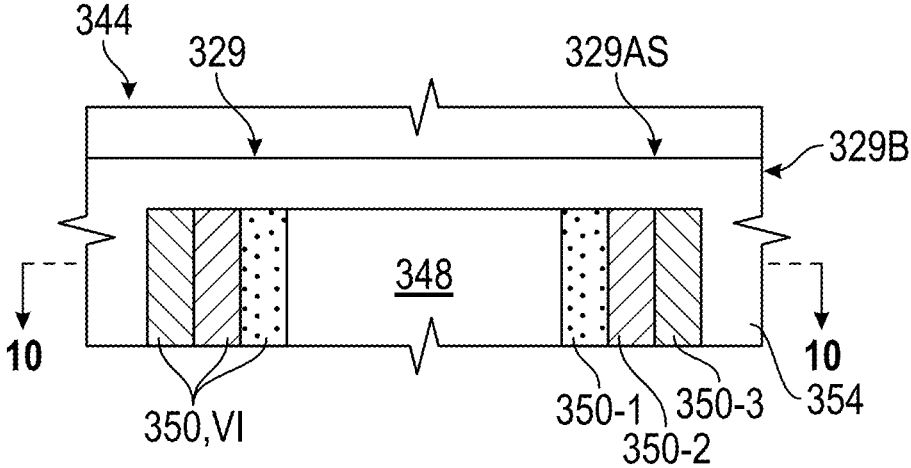

FIGS. 10-11 illustrate views of another virtual anatomical model in a graphical user interface.

Figure 12:
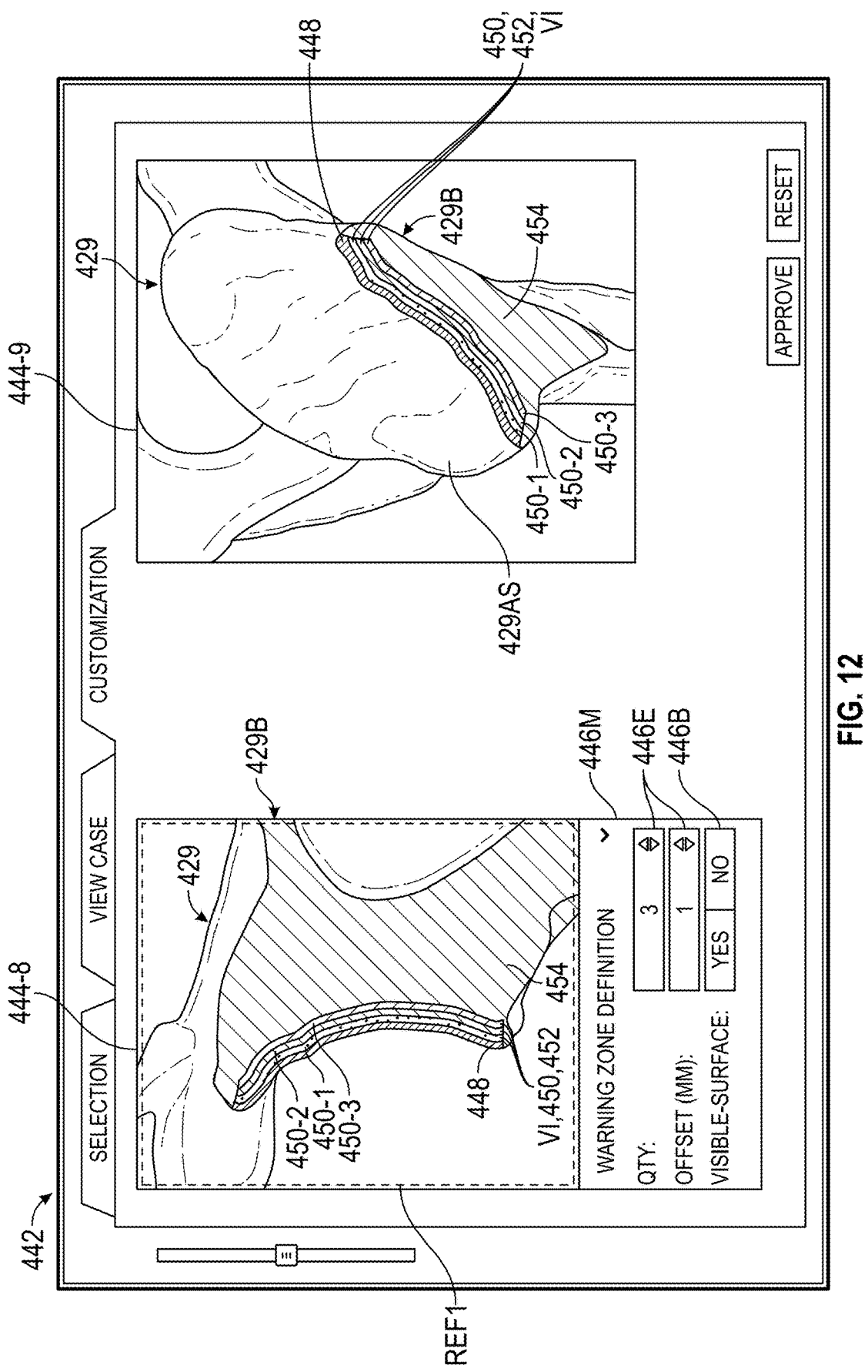

FIG. 12 illustrates another virtual anatomical model including target and warning zones in a graphical user interface.

Figure 13:
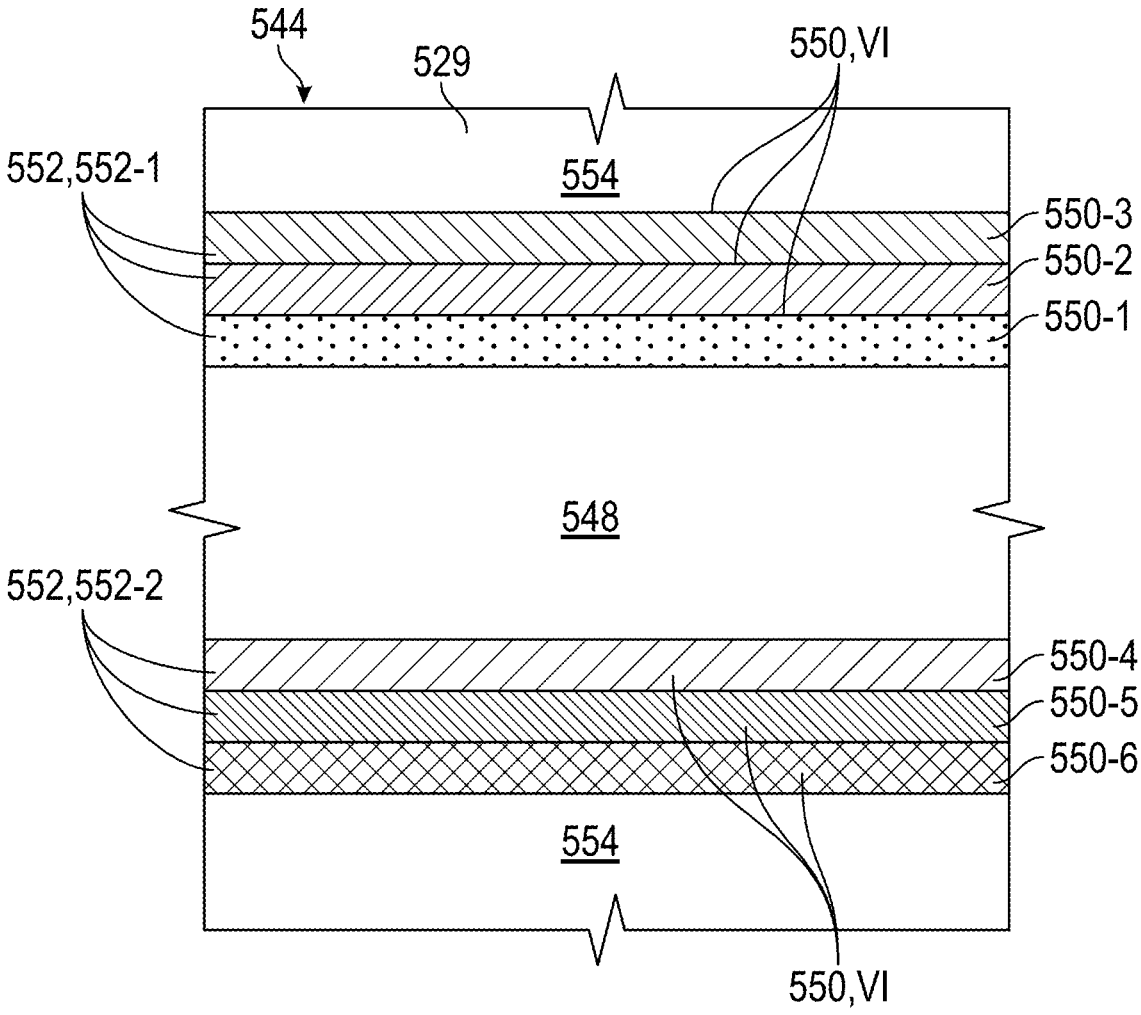

FIG. 13 illustrates another virtual anatomical model in a graphical user interface.

Figure 14:
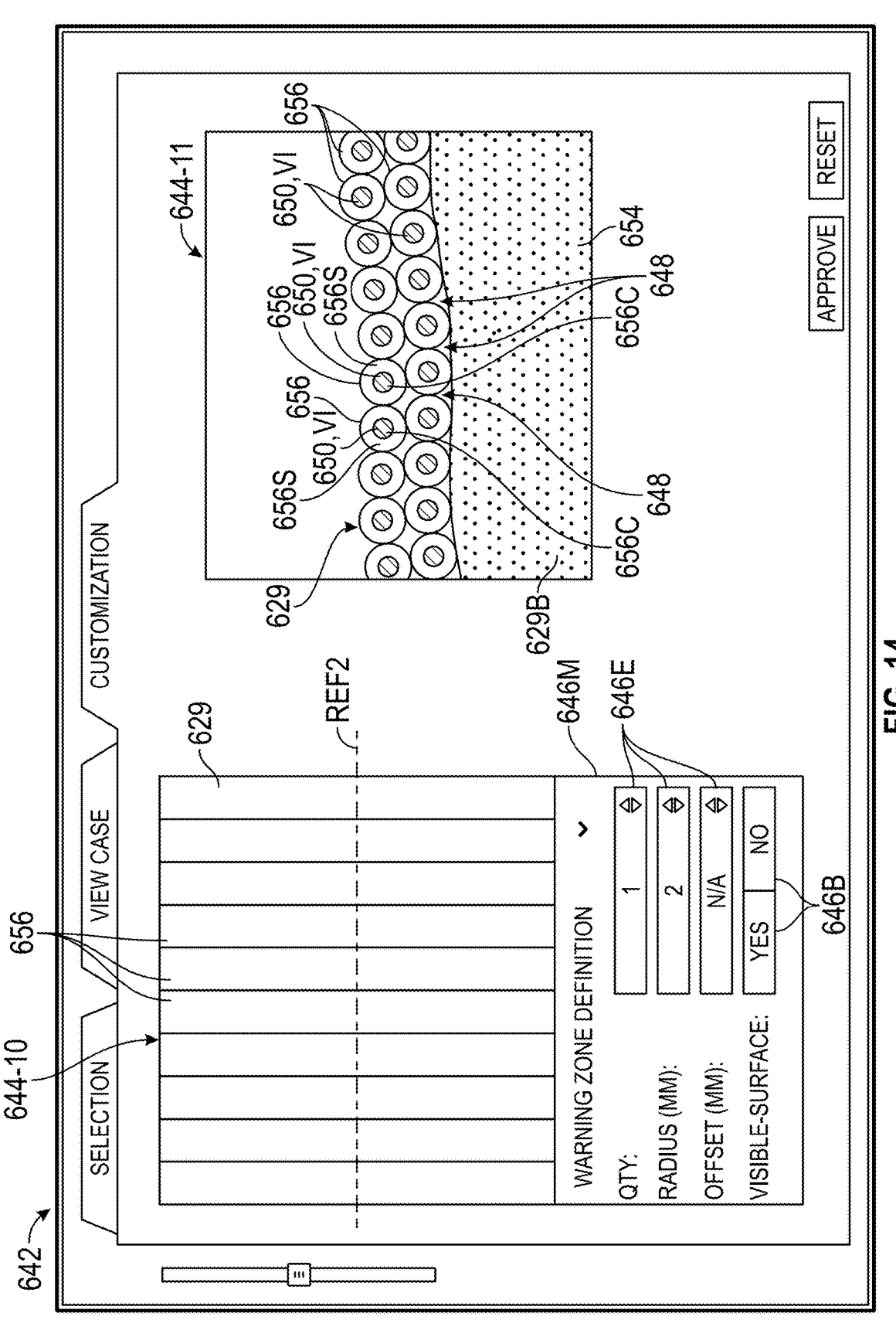

FIG. 14 illustrates a fiber arrangement of a virtual anatomical model in a graphical user interface.

Figure 15:
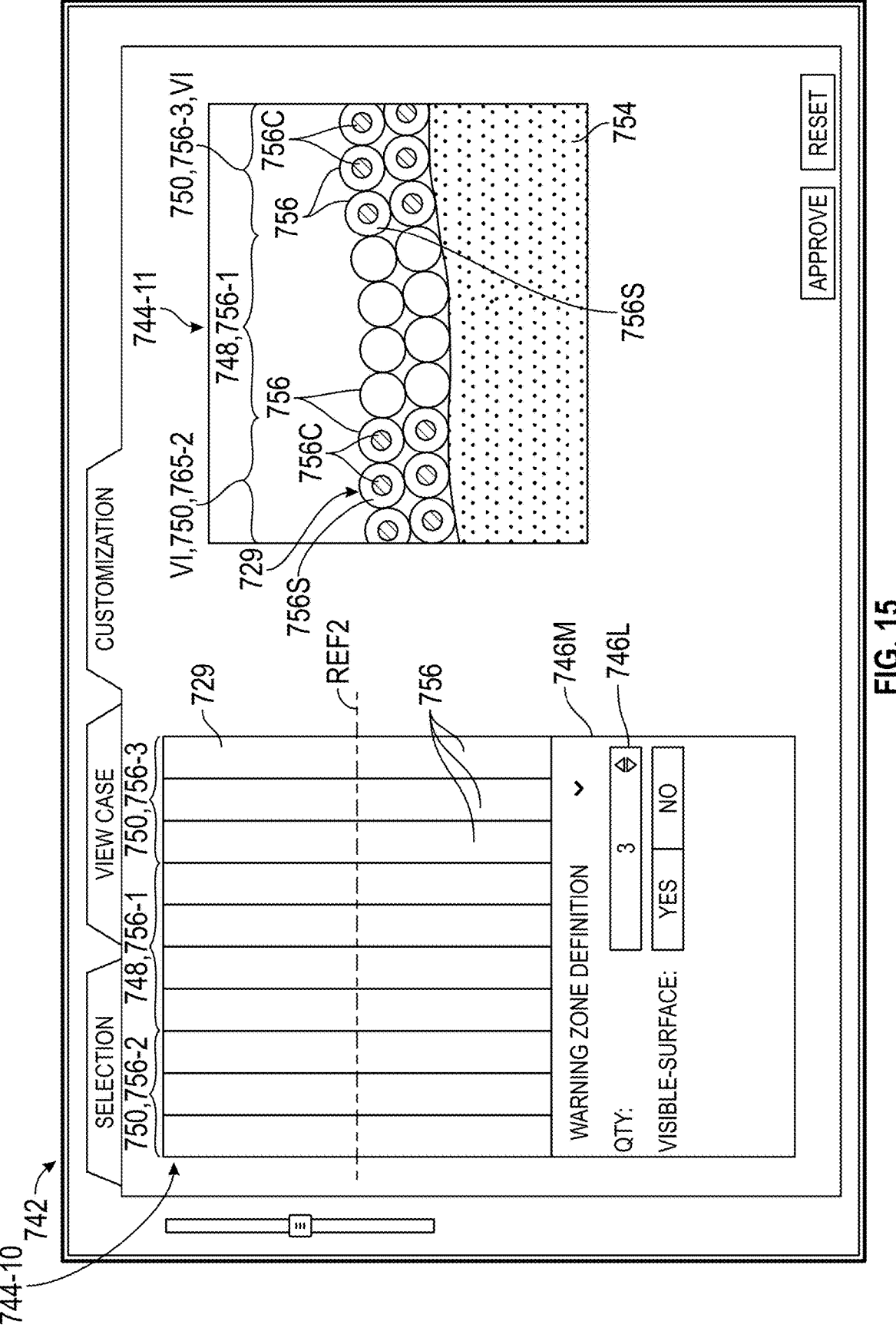

FIG. 15 illustrates another fiber arrangement of a virtual anatomical in a graphical user interface.

Figure 16:
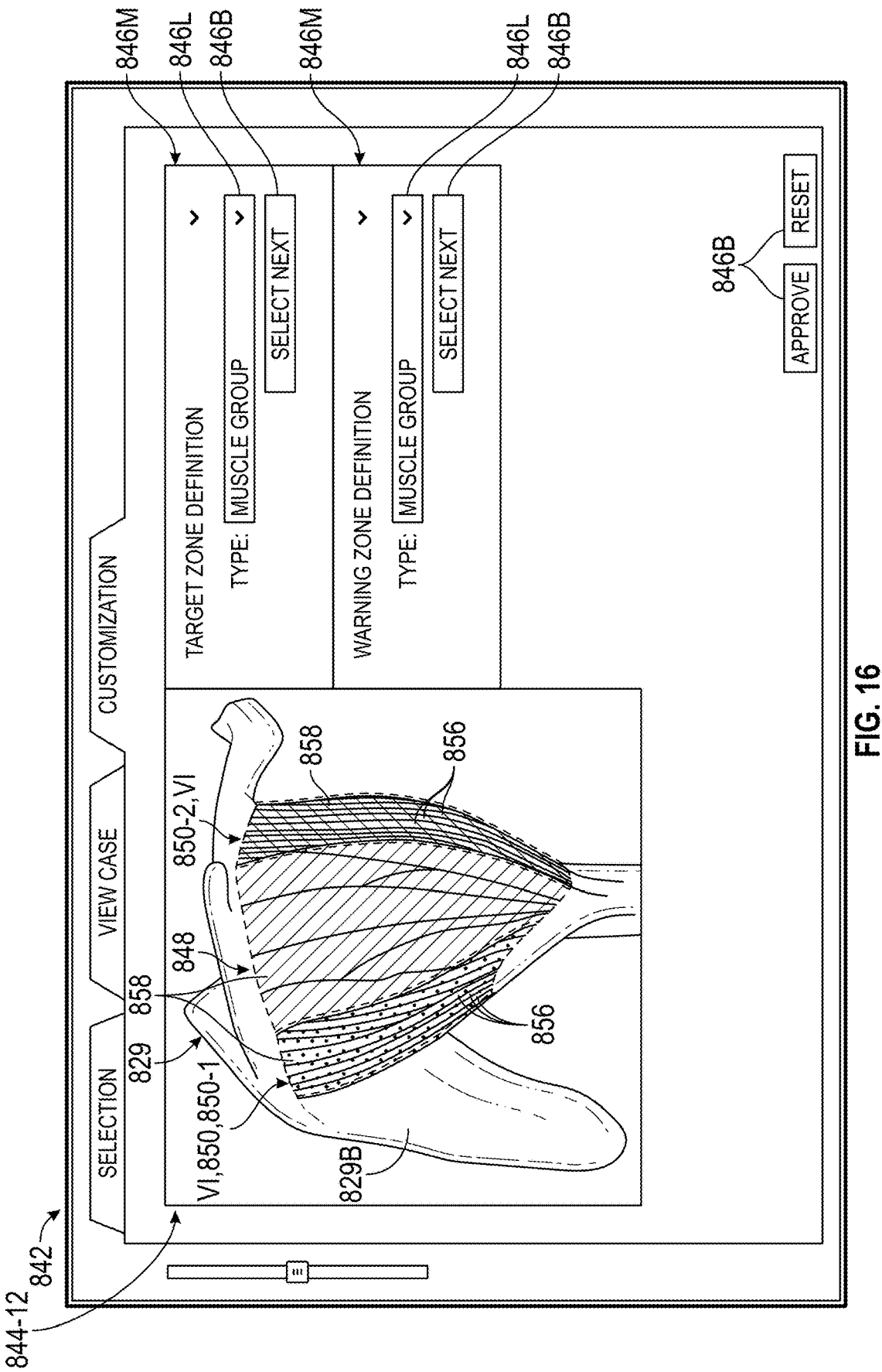

FIG. 16 illustrates an arrangement of muscle groups of a virtual anatomical in a graphical user interface.

Figure 17A:
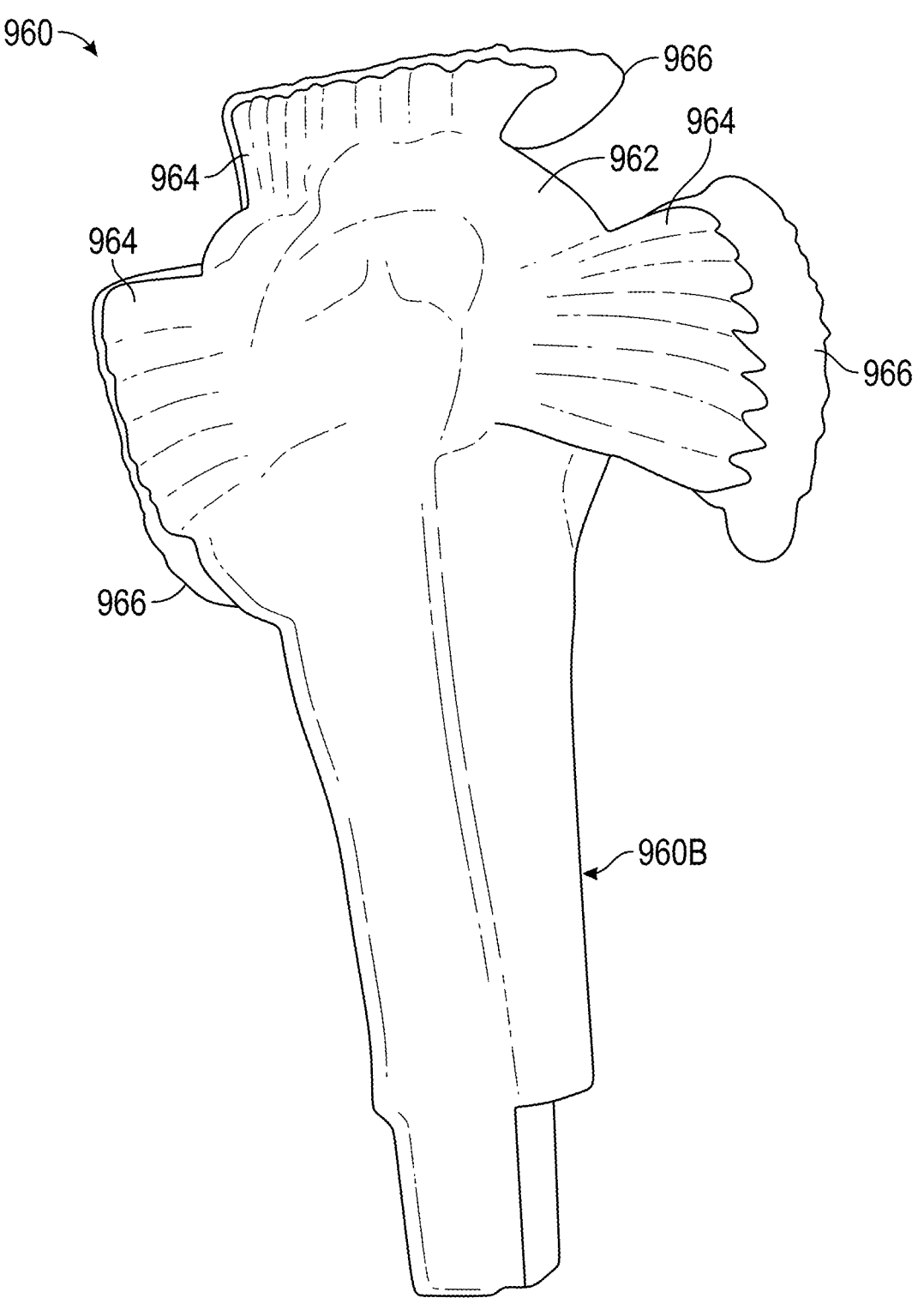

FIG. 17A illustrates a side view of a physical anatomical model.

Figure 17B:
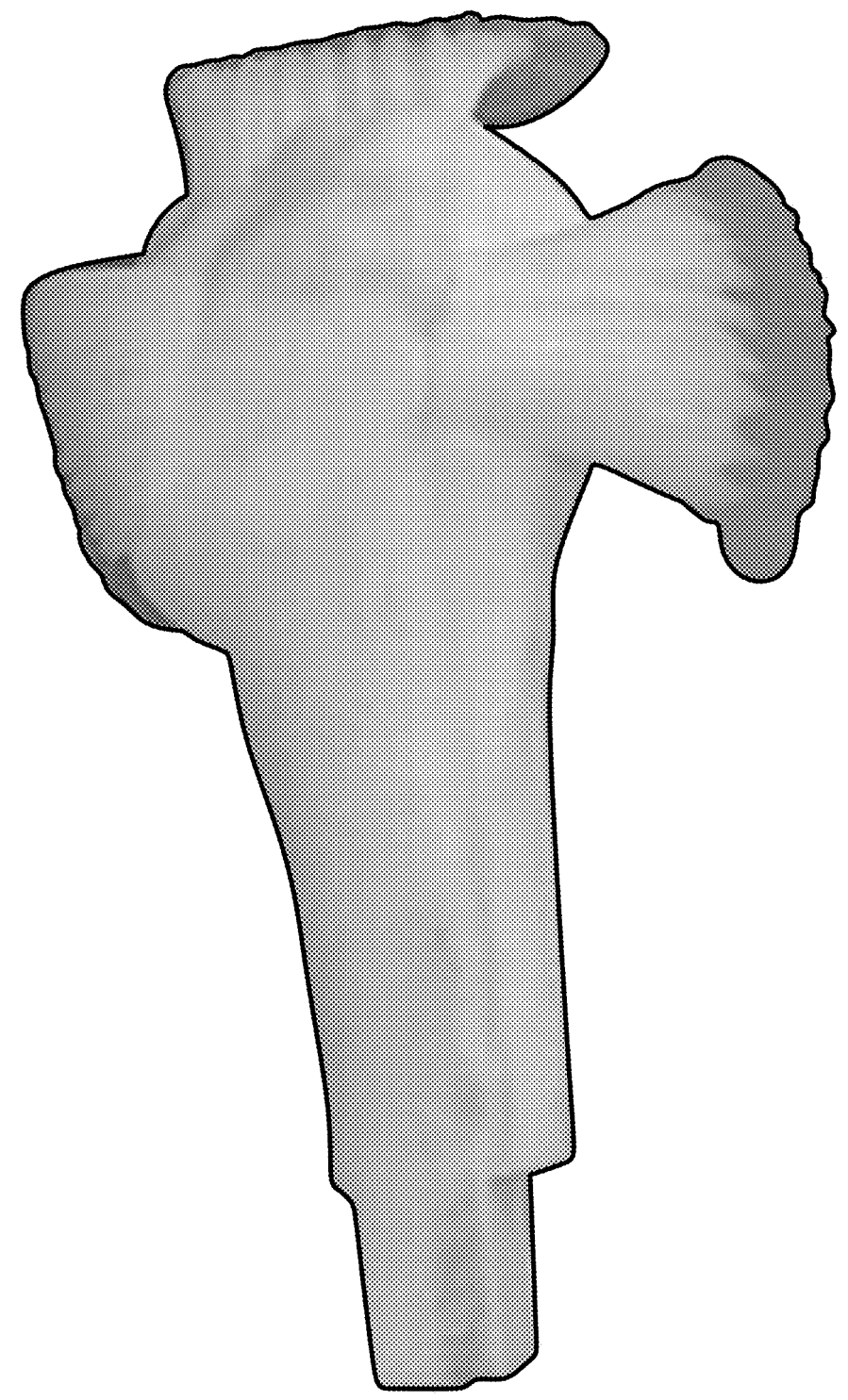

FIG. 17B is a grayscale image of the physical anatomical model of FIG. 17A.

Figure 18:
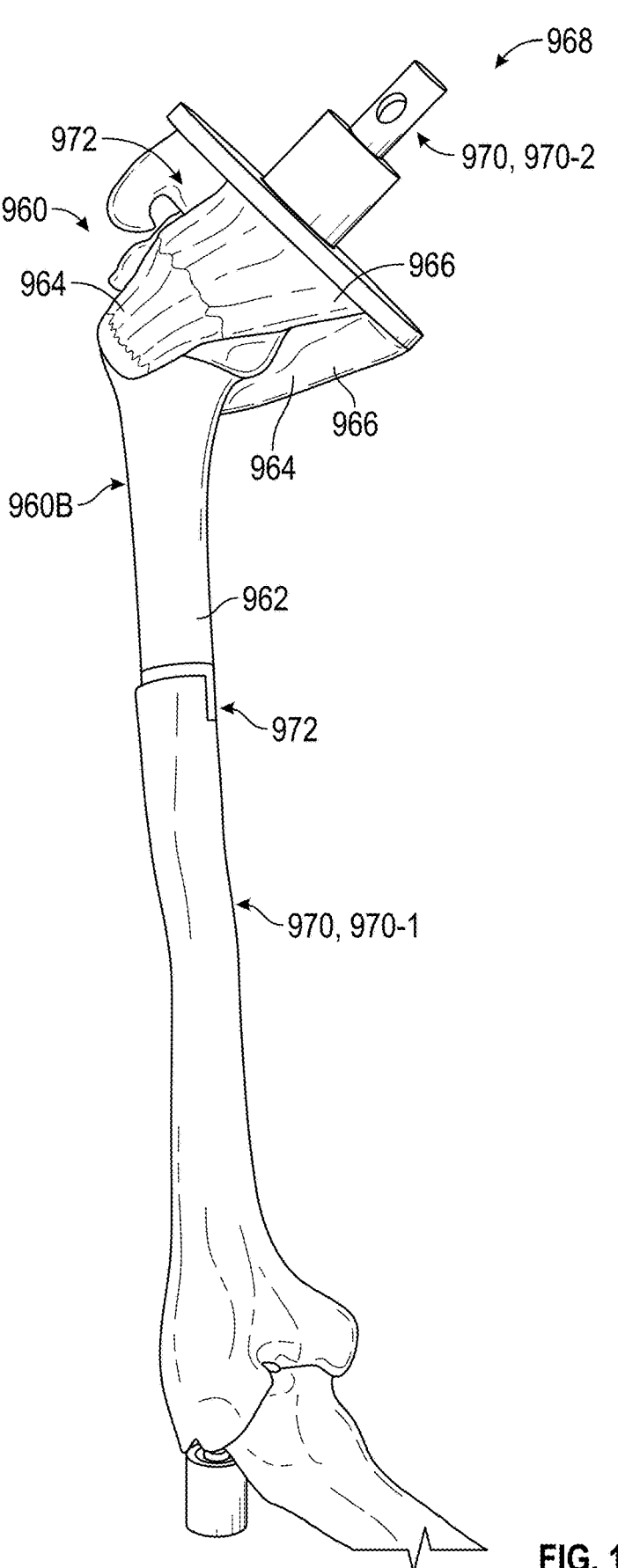
Figure 19:
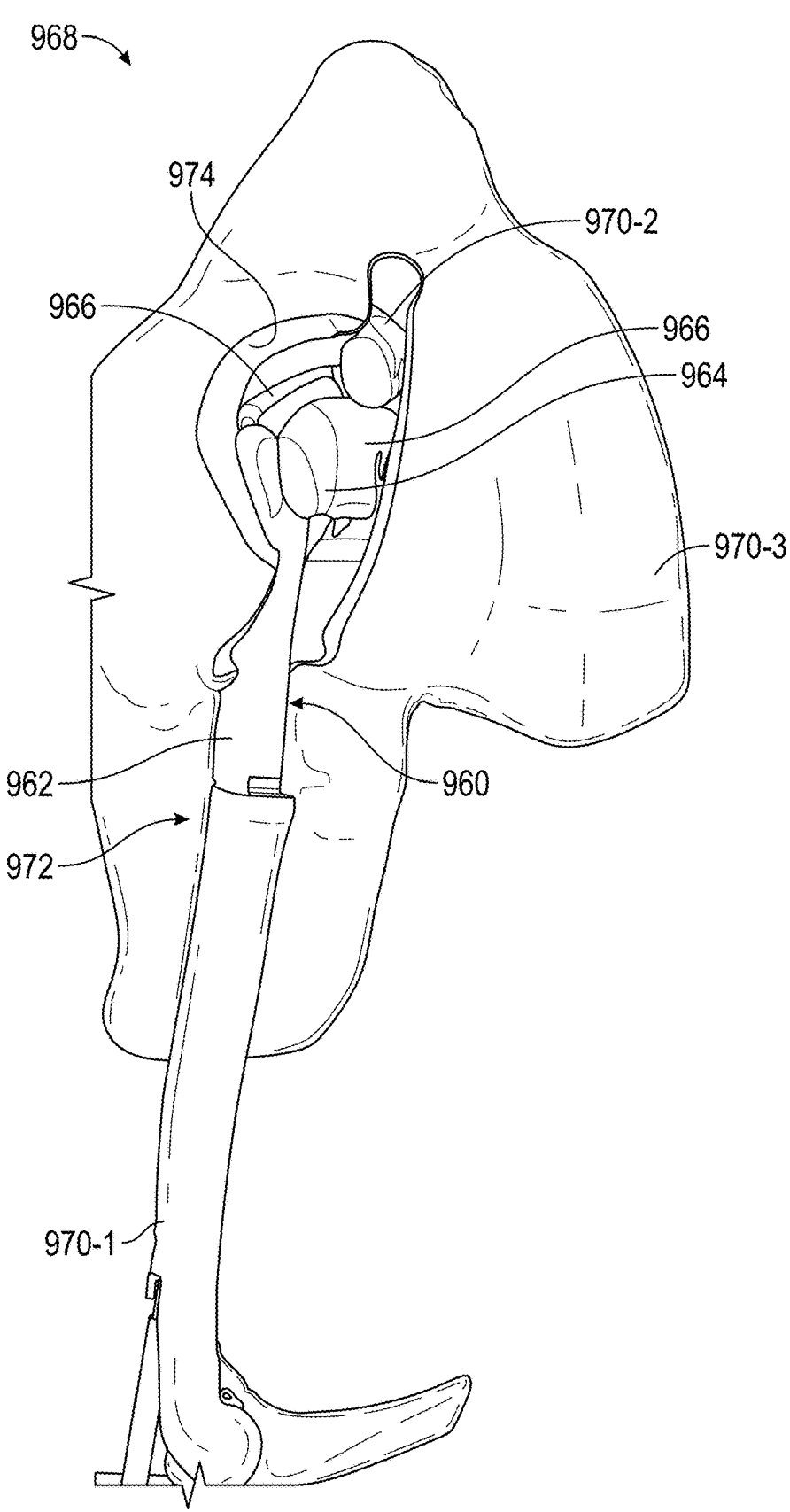

FIGS. 18-19 illustrate side views of the physical anatomical model of FIG. 17A coupled to fixtures.

Figure 20:
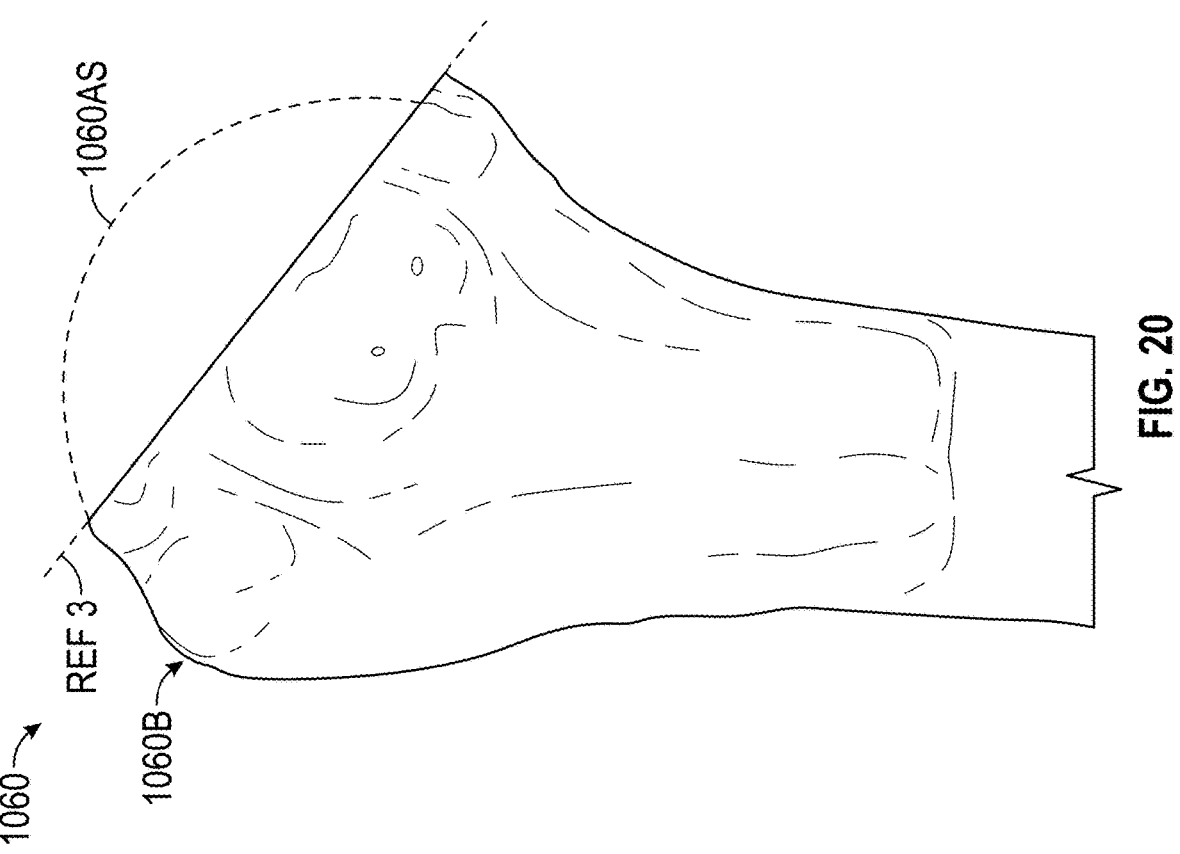

FIG. 20 illustrates a side view of another physical anatomical model including a modification.

Figure 21:
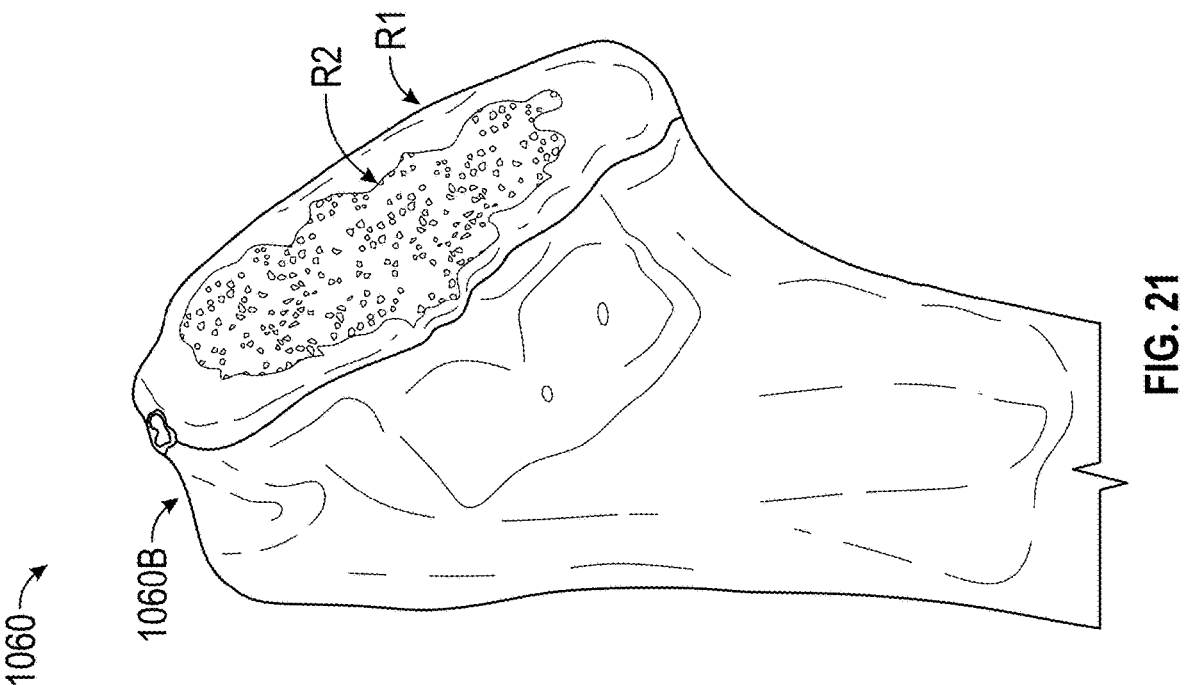

FIG. 21 illustrates a perspective view of the physical anatomical model of FIG. 20.

Figure 22:
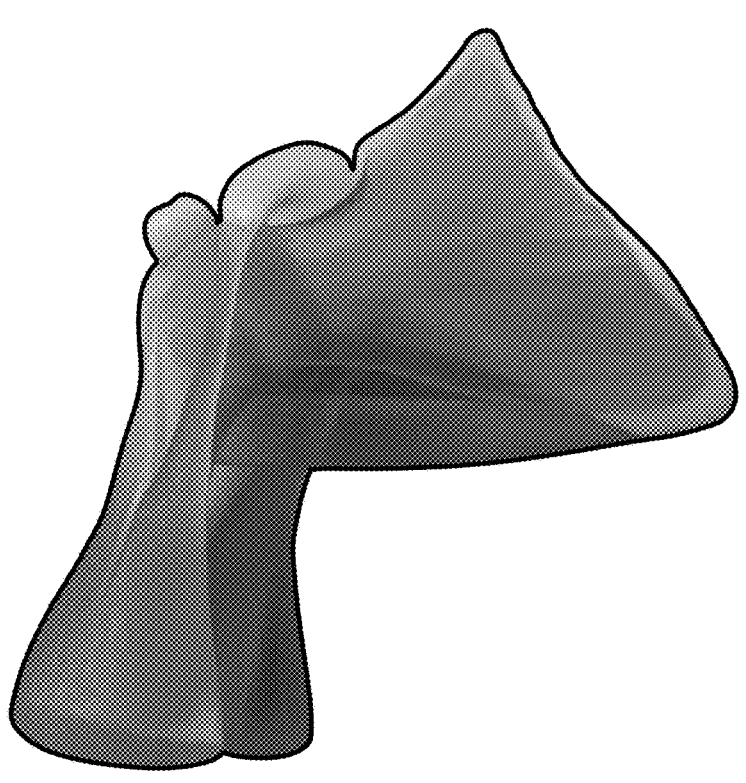
Figure 23:
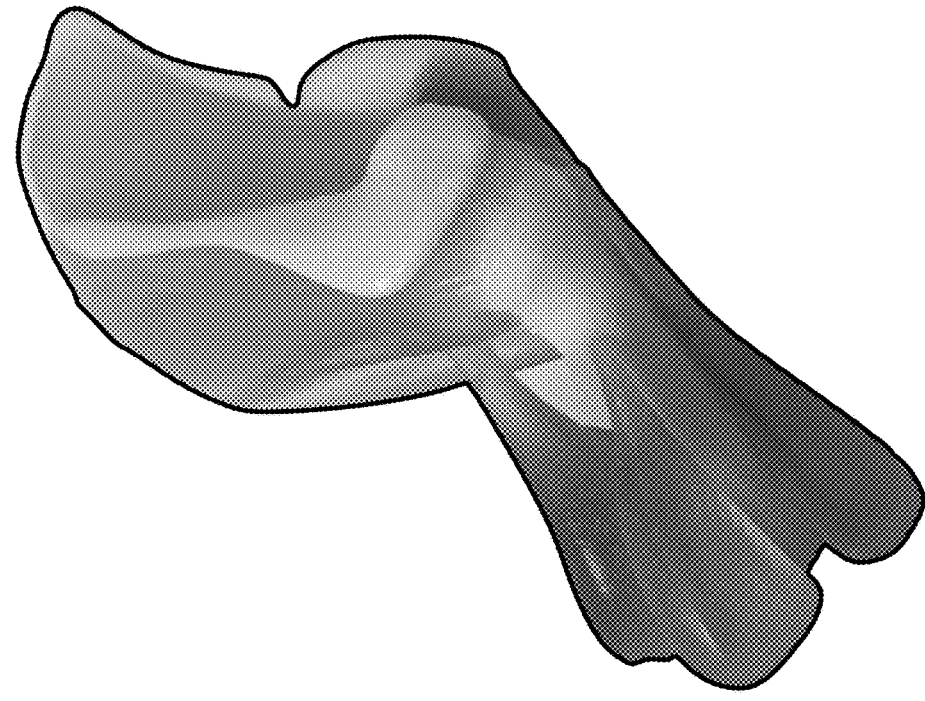

FIGS. 22-23 are grayscale images of another physical anatomical model.

Figure 24:
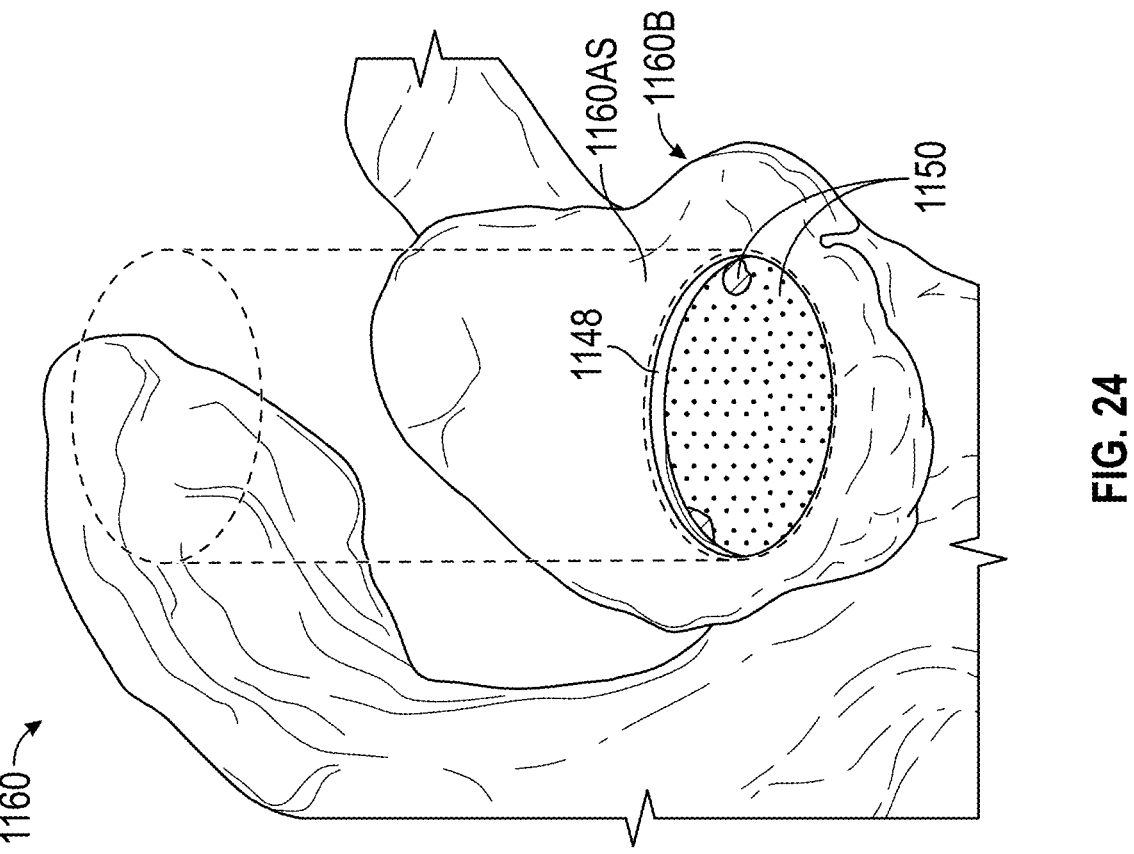

FIG. 24 illustrates another physical anatomical model including target and warning zones exposed by a modification.

Figure 25:
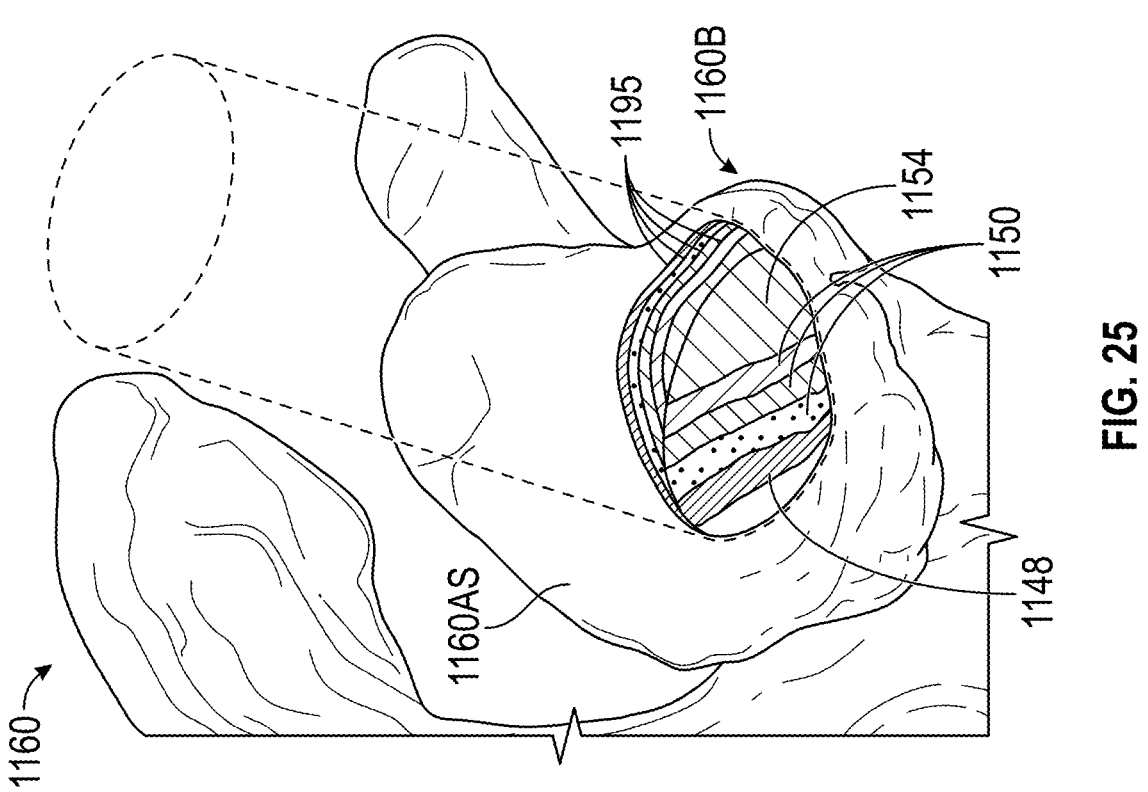

FIG. 25 illustrates the physical anatomical model of FIG. 24 including target and warning zones exposed by another modification.

Figure 26:
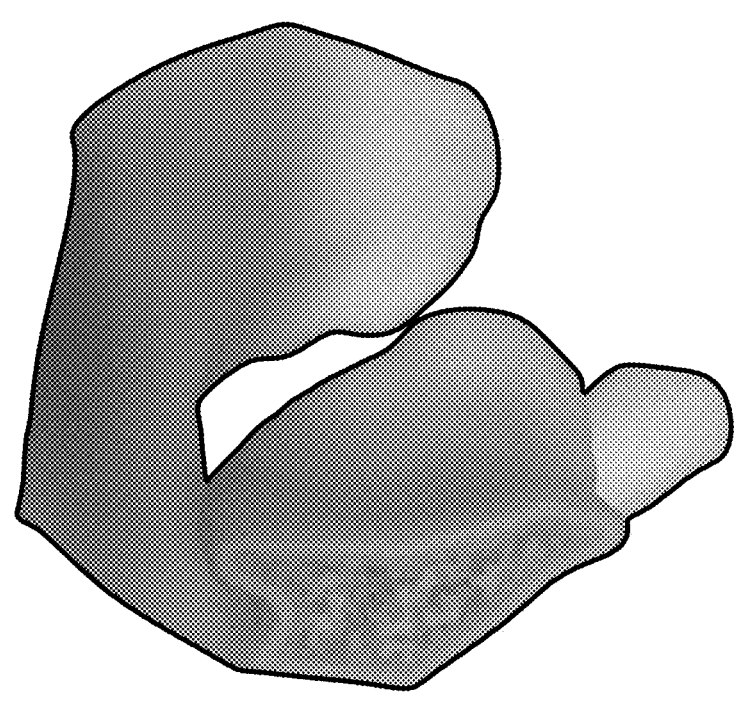
Figure 27:
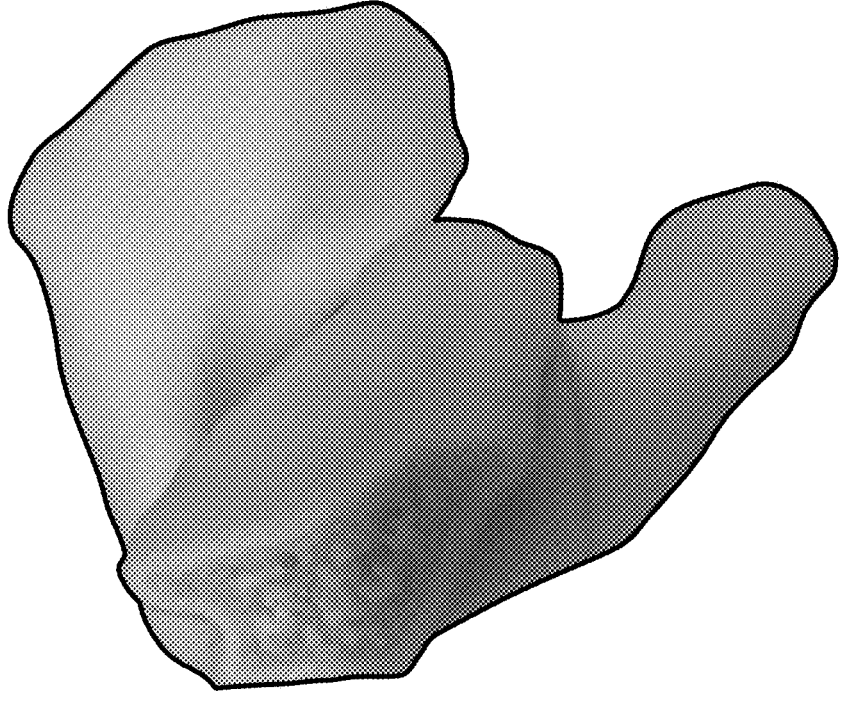

FIGS. 26-27 are grayscale images of a sectioned physical anatomical model including a warning zone established about a cancellous region of bone.

Figure 28:
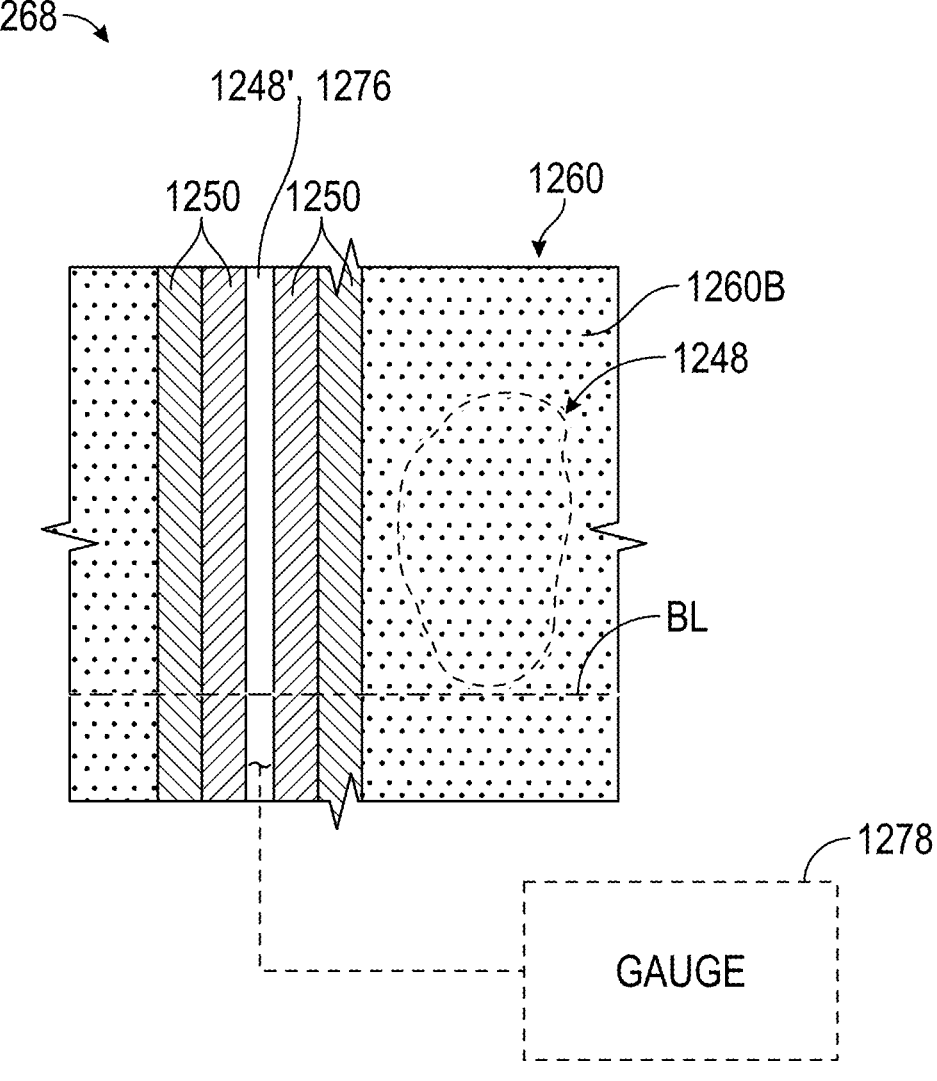

FIG. 28 illustrates an assembly incorporating a physical anatomical model.

Figures 29, 30, 31:
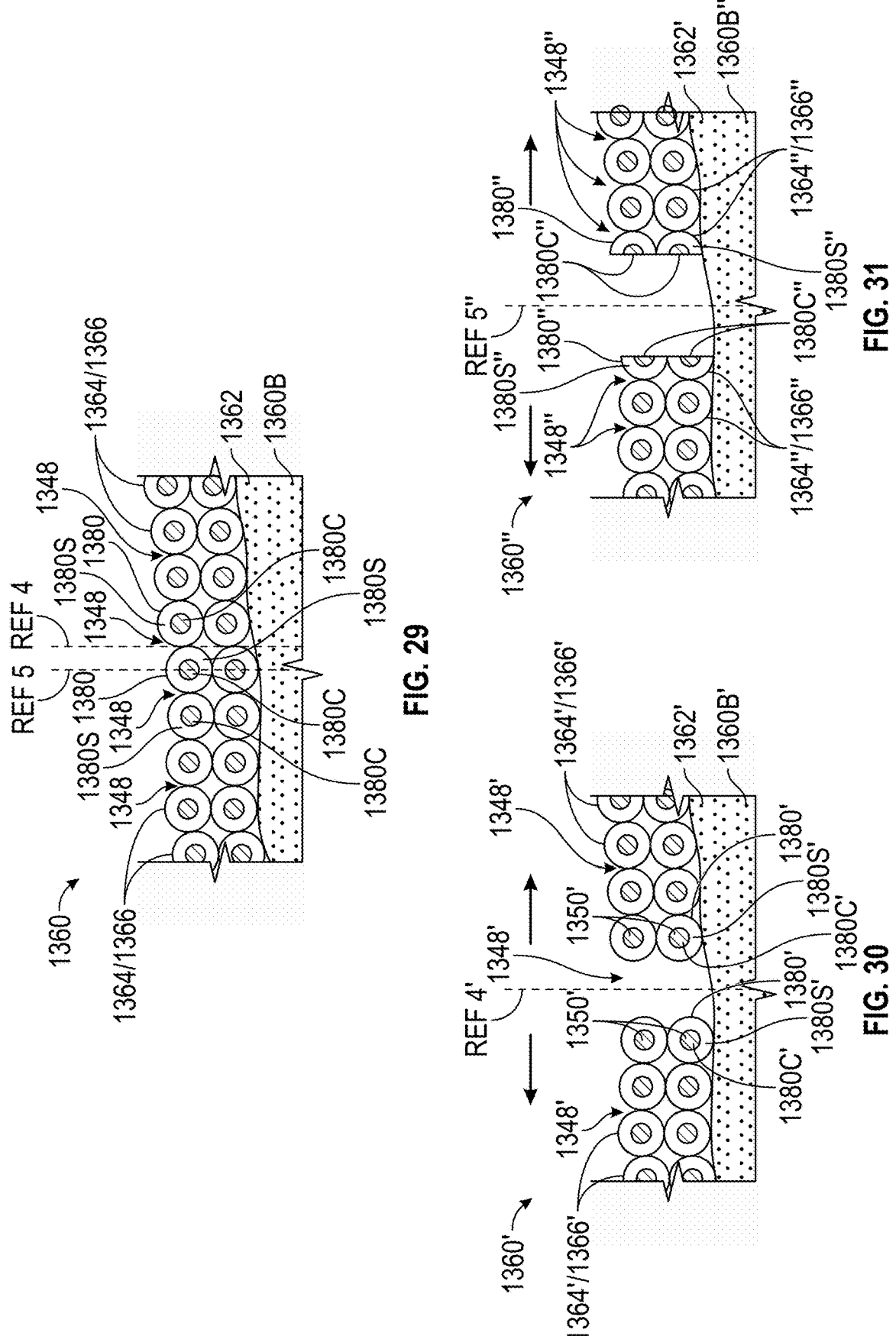

FIG. 29 illustrates another physical anatomical model including a fiber arrangement.

FIGS. 30-31 illustrate modifications to the physical anatomical model of FIG. 29.

Figure 32:
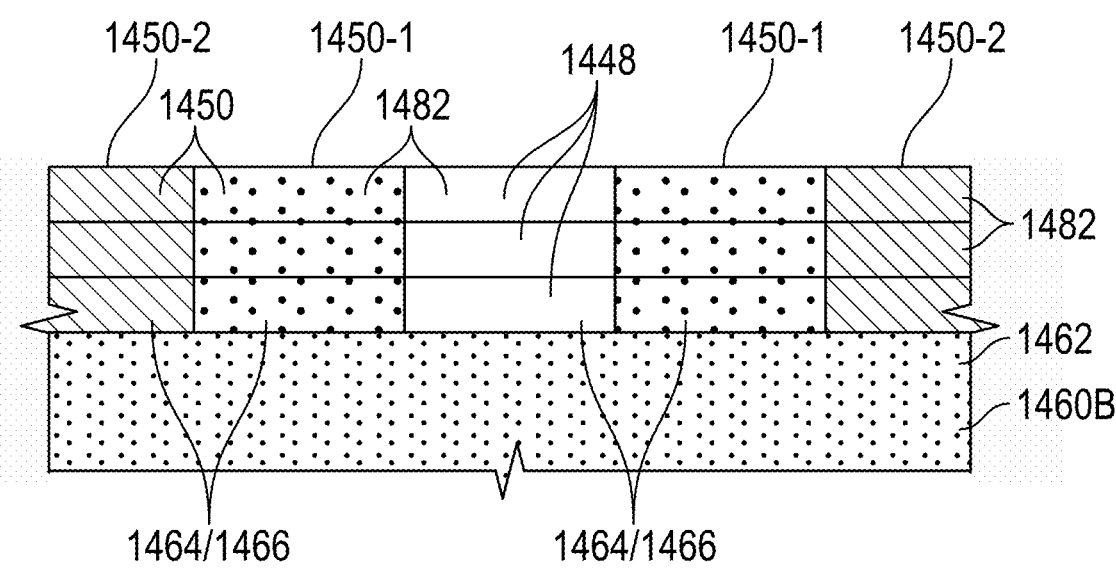

FIG. 32 illustrates another physical anatomical model including an arrangement of sheets.

Figure 33:
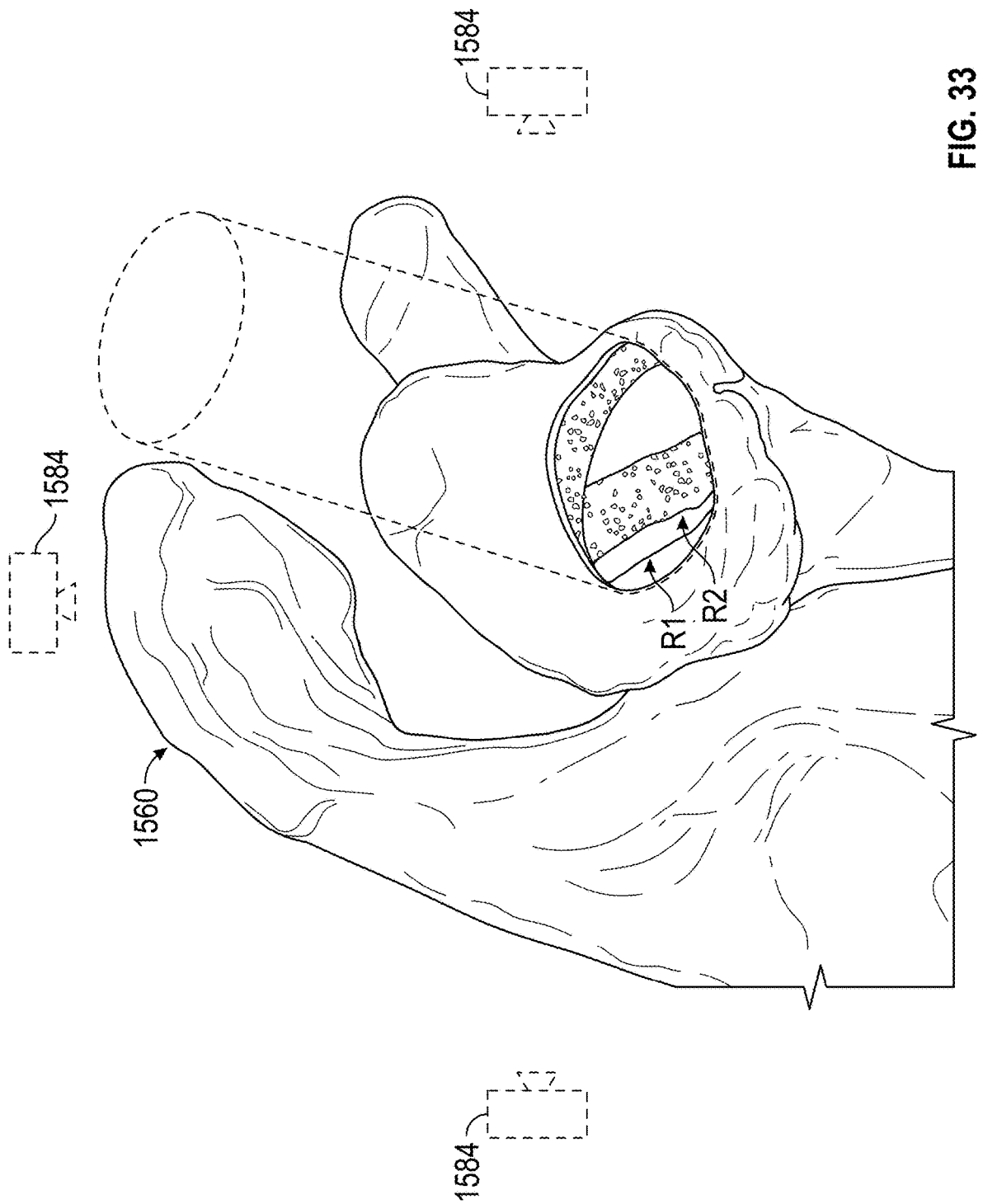

FIG. 33 illustrates a revised physical anatomical model relative to imaging devices.

Figure 34:
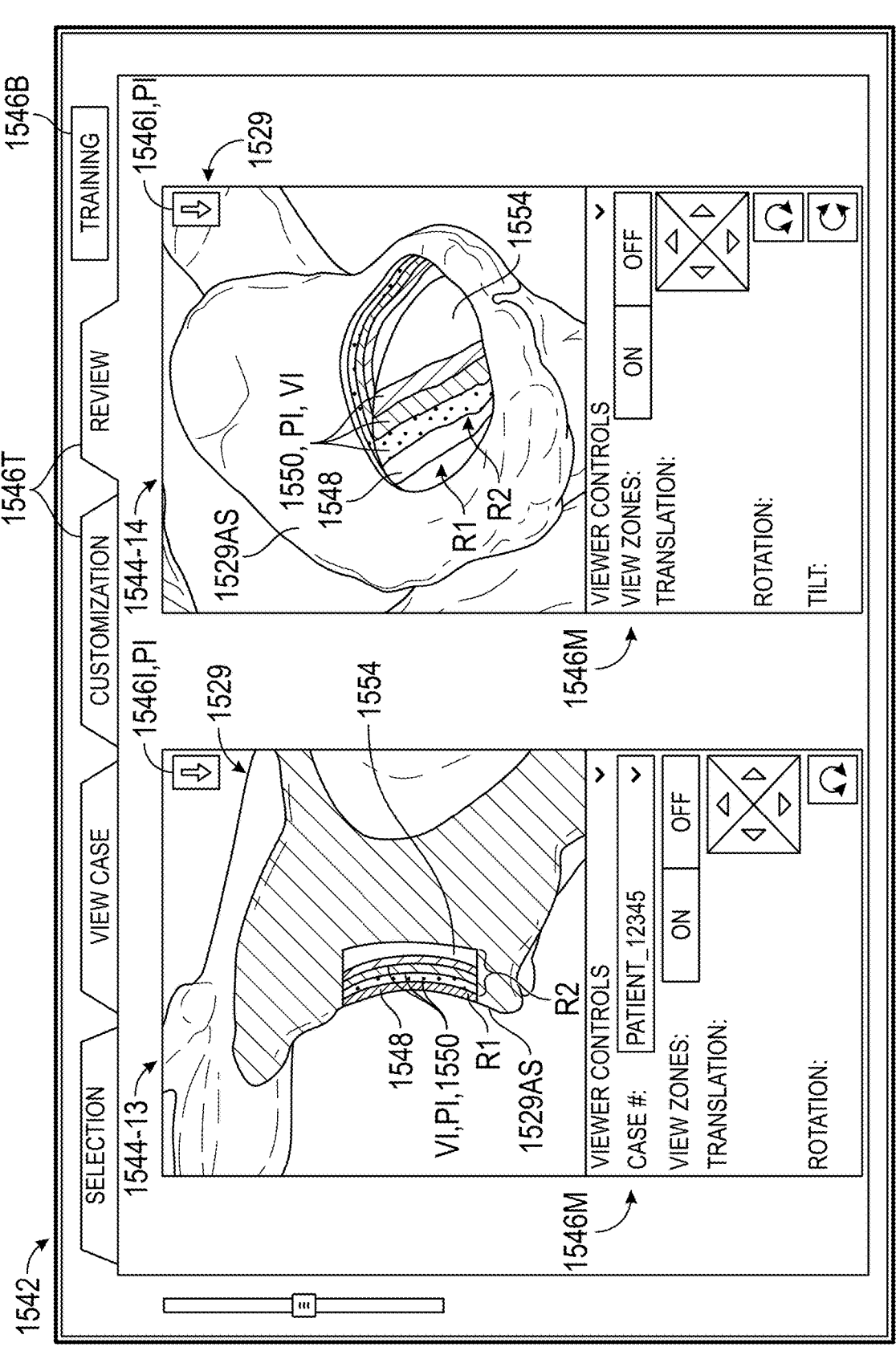

FIG. 34 illustrates original and revised virtual anatomical models associated with the physical anatomical model of FIG. 33.

FIG. 35 illustrates another physical anatomical model.

FIG. 36 illustrates a revised version of the physical anatomical model of FIG. 35 positioned relative to an imaging device.

Figure 37:
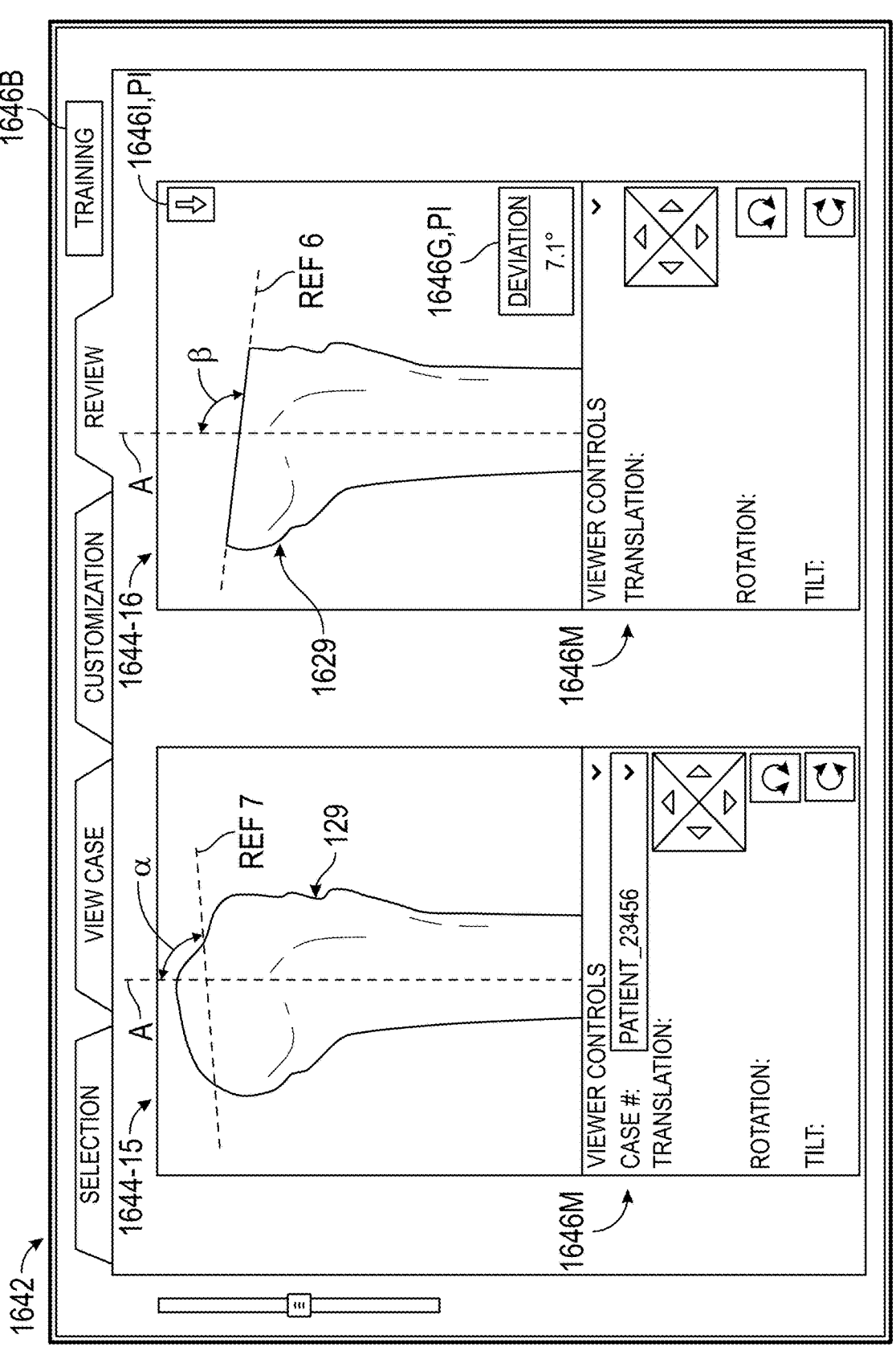

FIG. 37 illustrates original and revised virtual anatomical models associated with the physical anatomical model of FIG. 36.

Figure 38:
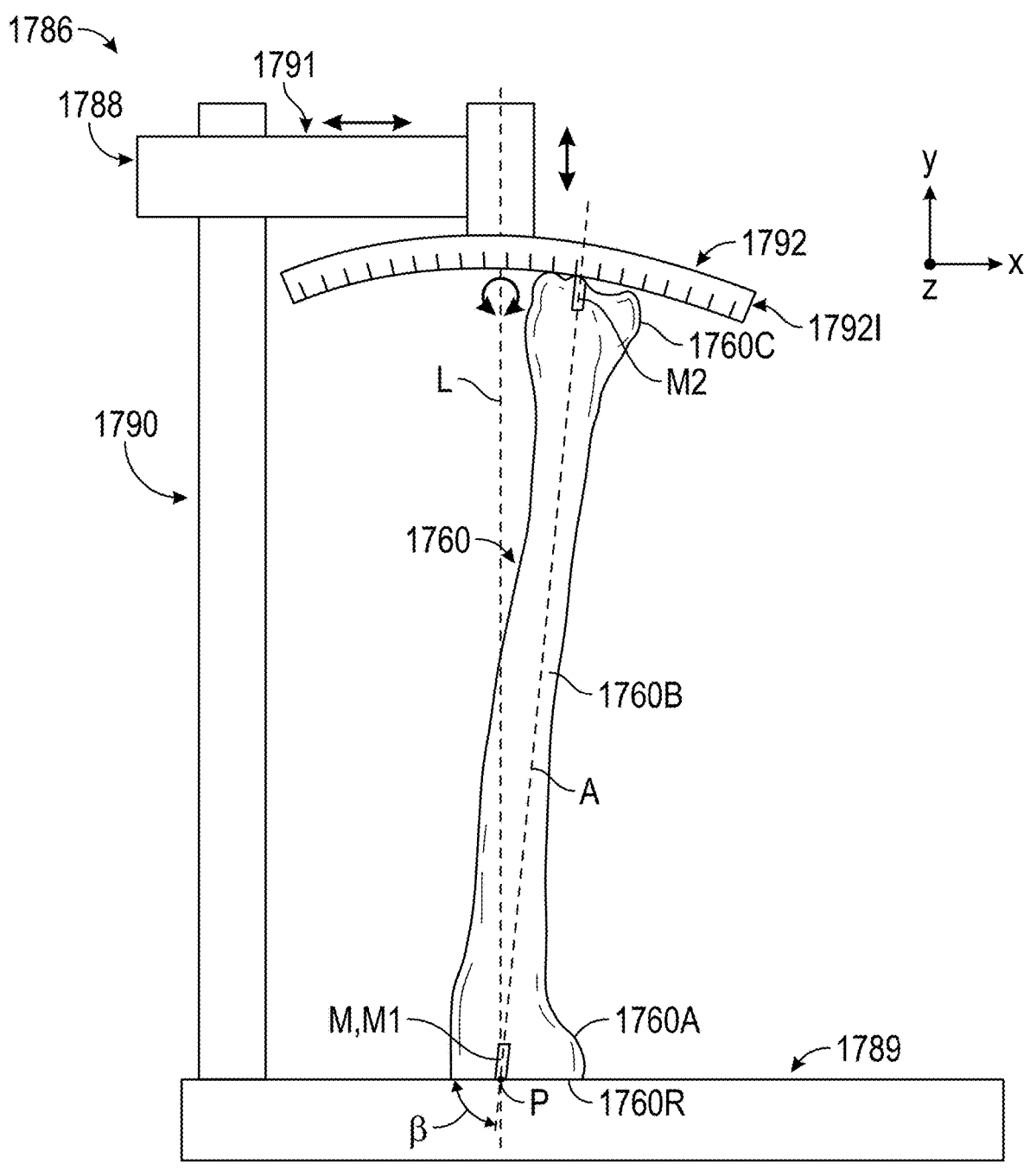

FIG. 38 illustrates a training assembly including a measurement device positioned relative to a revised physical anatomical model.

Figure 39:
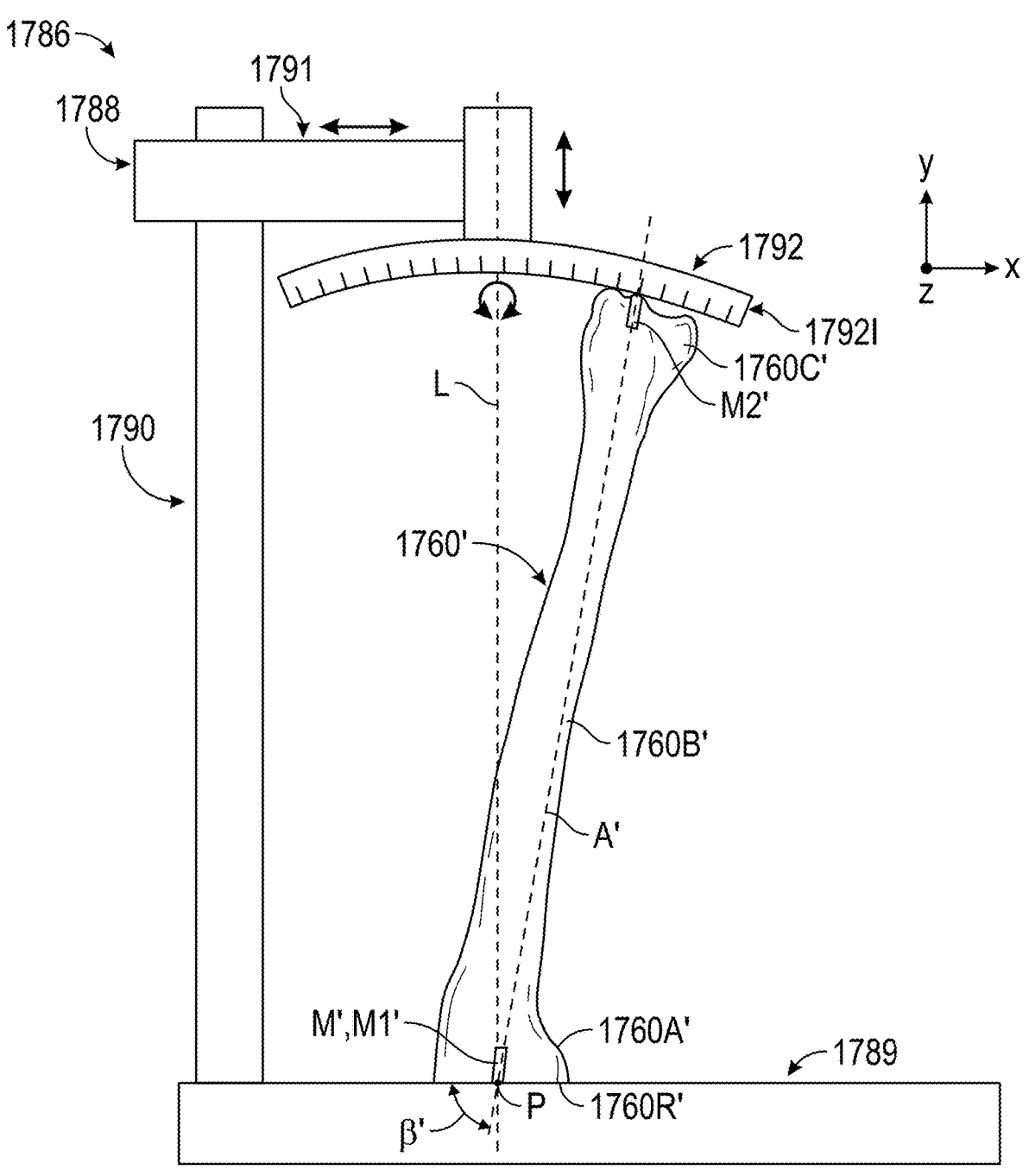

FIG. 39 illustrates the measurement device of FIG. 38 positioned relative to another revised physical anatomical model.

Figure 40:
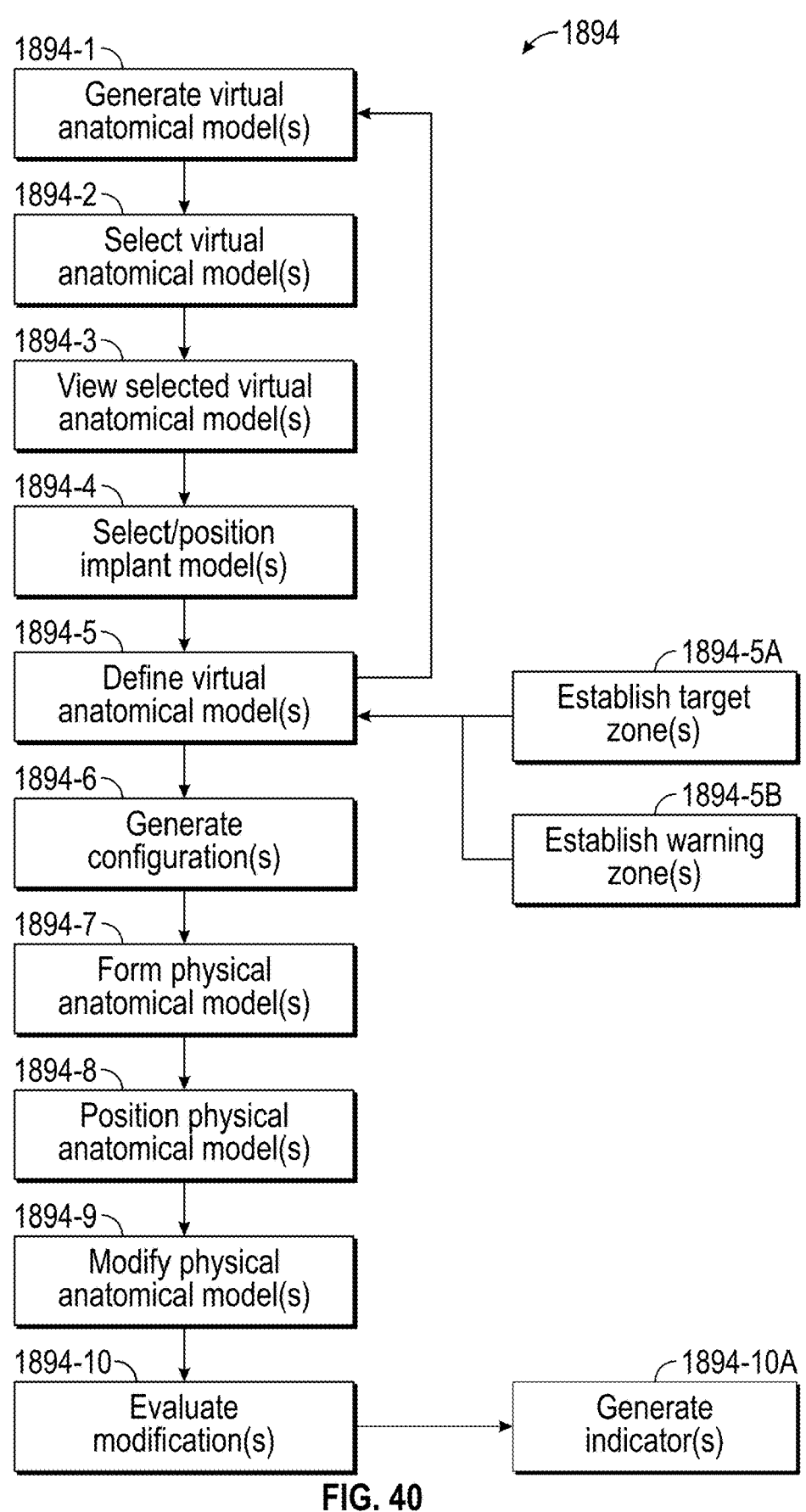

FIG. 40 illustrates an exemplary method of planning and implementing a surgical procedure.

Figure 41:
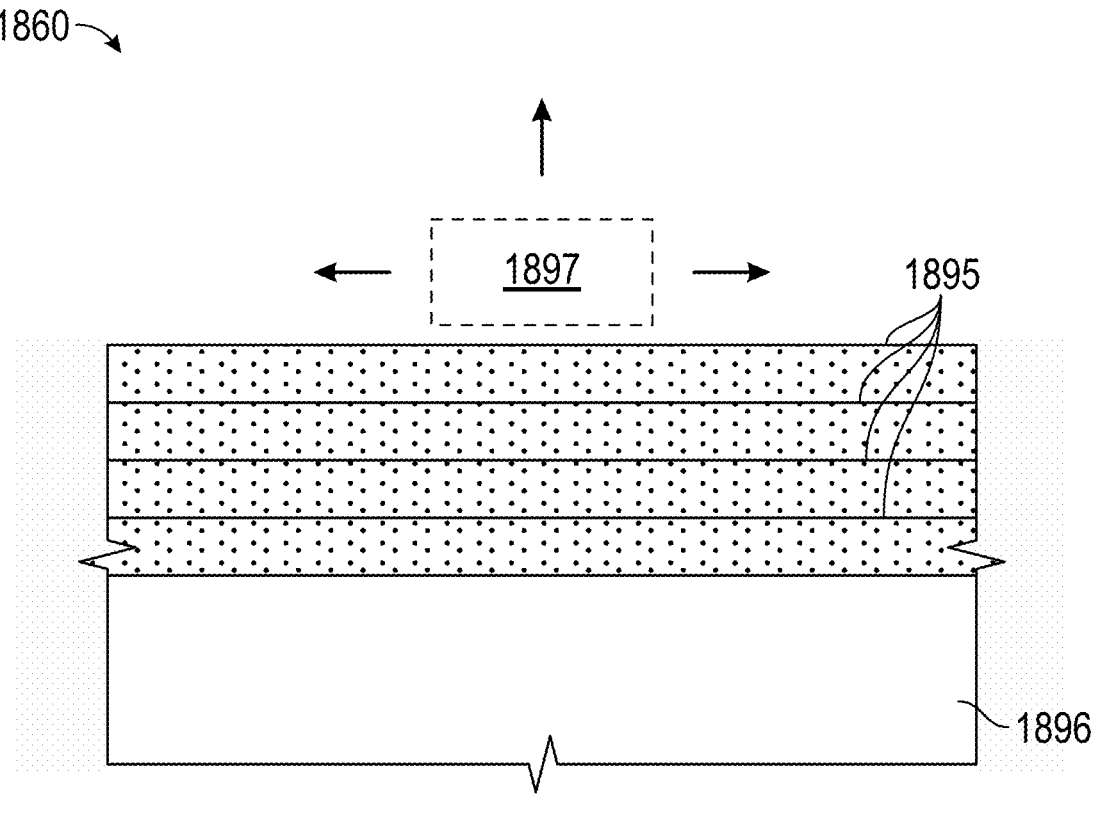

FIG. 41 illustrates another physical anatomical model.

Like reference numbers and designations in the various drawings indicate like elements.

DETAILED DESCRIPTION

This disclosure relates to surgical systems, devices and methods for planning and implementing surgical procedures utilizing physical models of anatomy. Physical anatomical models may be utilized to rehearse and train for various surgical procedures.

The disclosed techniques may be utilized to provide the surgeon a training experience that may be targeted or tailored to the surgeon based on skill set, experience, etc. The surgeon may select a particular configuration of a virtual anatomical model that may be fabricated or otherwise formed to establish a physical anatomical model based on the anatomy or pathology that the surgeon may intend to treat. In scenarios, the surgeon may not be familiar with a particular deformity and may choose to train utilizing that configuration of the physical anatomical model. The surgeon may utilize the physical anatomical model to train with particular instrumentation, implants and other devices that may be intended for a planned surgery. Once training on the physical anatomical model is completed, the surgeon may select a more challenging case in a subsequent training cycle. Unlike cadaveric and saw bone specimens, the physical anatomical model may be associated with a specific patient which may improve the ability to determine how well the surgeon actually performed the surgical procedure with respect to the intended anatomy.

The surgeon, assistant or other user may interact with a graphical user interface (GUI) to select various parameters or characteristics of the physical anatomical model. The parameters may include anatomy, joint type, tissue type, bone density, defect type, color scheme, etc., to establish a desired configuration of the physical anatomical model. The surgeon may tailor or select one or more variables or parameters specific to a patient, depending on what the surgeon would like to train. The specified parameters may be represented in the physical anatomical model.

The surgeon may interact with the user interface to select a desired case associated with a respective virtual anatomical model. The surgeon may interact with the user interface to review prior cases, such as the case of a particular esteemed surgeon which may be recognized as the "gold standard" for a respective procedure. The surgeon may select a case corresponding to an intended patient or may select a case that may closely correspond to a particular classification.

The target zones and warning zones may include one or more properties that differ from each other and/or that differ from one or more naturals properties of respective portions of the anatomy. The physical anatomical model may include different constructions, including various densities, porosities, textures, coloring and/or shading. The physical anatomical model may incorporate one or more target zones and warning zones. The warning zones may provide feedback to the surgeon, and may include visual, tactile and/or audible indicators. The target zones and warning zones may be implemented utilizing any of the techniques disclosed herein, including different colors, shades, fluorescence, light emittance and other visual contrasts, different material properties including composition comprising metallic and/or non-materials, moduli of elasticity, densities, porosities and conductivity, different tactile properties including different textures, and different audible properties including sound emittance.

The physical anatomical model may serve as an artifact for the surgeon. The surgeon may leave a training facility with a revised physical anatomical model once training is completed. The surgeon may refer to the revised physical anatomical model prior to and during a surgical procedure on a respective patient.

A physical anatomical model according to an implementation of the present disclosure includes, inter alia, a main body including a target zone and one or more warning zones adjacent to the target zone that may cooperate to establish a construction representative of an anatomy. The target zone may have a property associated with a respective portion of the anatomy. Each warning zone may have a property that may differ from a natural property of a respective portion of the anatomy and that may differ from the property of the target zone.

In a further implementation, the property of the warning zone may differ from the property of the target zone with respect to at least one of color, shade, fluorescence, light emittance, material property, modulus of elasticity, density, porosity, conductivity, tactile property, and audible property.

In a further implementation, the property of the target zone may include a color that may correspond to a natural color of the respective portion of the anatomy. The property of each warning zone may include a respective artificial color that may differ from a natural color of the respective portion of the anatomy and that may establish a visual contrast with the natural color associated with the target zone.

A physical anatomical model according to an implementation of the present disclosure includes, inter alia, a main body that may include a target zone and one or more warning zones adjacent to the target zone that may cooperate to establish a construction representative of an anatomy. The target zone may have a color that may correspond to a natural color of a respective portion of the anatomy. Each warning zone may have a respective artificial color that may differ from a natural color of a respective portion of the anatomy and that may establish a visual contrast with the natural color associated with the target zone.

In a further implementation, the one or more warning zones may be a plurality of warning zones that may correspond to a plurality of layers in stacked relationship. The artificial colors of the layers may differ from each other.

In a further implementation, the plurality of layers may substantially encircle the target zone.

In a further implementation, the target zone may have a truncated conical geometry having a base establishing an entry point along an external surface of the main body.

In a further implementation, the plurality of layers may be offset at different depths from an external surface of the main body.

In a further implementation, the target zone may establish the external surface and may be representative of cortical bone associated with the anatomy. The main body may include a third zone that may be representative of cancellous bone associated with the anatomy. The plurality of layers may be arranged such that the warning zones may be established between the target zone and the third zone.

In a further implementation, the plurality of layers may include a first set of layers and a second set of layers. The target zone may be established between the first and second sets of layers.

In a further implementation, the target zone may extend inwardly from an external surface of the main body. The one or more warning zones may be established below the external surface.

In a further implementation, the target zone and the one or more warning zones may be representative of bone tissue associated with the anatomy.

In a further implementation, the main body may include a polymeric material.

In a further implementation, the target zone and the one or more warning zones may be representative of soft tissue associated with the anatomy.

In a further implementation, the soft tissue may include muscle tissue. The main body may include a bundle of fibers that may be representative of the muscle tissue. One or more of the fibers may establish a respective one of the warning zones. The target zone may be established between an adjacent pair of the fibers.

In a further implementation, each of the fibers may include an elastomeric material.

In a further implementation, the bundle of fibers may include a first set of fibers and a second set of fibers. The first set of fibers may establish the target zone. Each fiber of the second set of fibers may establish a respective one of the warning zones.

In a further implementation, each of the fibers may include a core and an outer sheath surrounding the core. The core may establish a respective one of the warning zones.

In a further implementation, the construction may be representative of a glenoid.

A training device for a surgical procedure according to an implementation of the present disclosure includes, inter alia, a physical anatomical model including a main body representative of an anatomy and an indication member embedded in the main body. The indication member may be representative of a nerve of the anatomy. The indication member may be configured to generate an indicator in response to meeting a predetermined criterion.

In a further implementation, the indication member may include an electrically conductive material. The indicator may be associated with an electrical signal. The indication member may be configured to establish the electrical signal in response to contact between an electrically conductive device and the indication member.

In a further implementation, the indication member may be coupled to a strain gauge. The strain gauge may be responsive to tensioning the indication member.

In a further implementation, the main body may include a warning zone that may extend along the indication member. The warning zone may have an artificial color that may differ from a natural color of a respective portion of the anatomy.

A training assembly for a surgical procedure according to an implementation of the present disclosure includes, inter alia, a physical anatomical model including a main body that may have a construction representative of an anatomy. The main body may extend between a first end portion and a second end portion. A measurement device may include a base, a tower and an outrigger. The tower may extend in a first direction from the base. The outrigger may extend laterally from the tower. The outrigger may include a ruler that may be situated over a predetermined position along the base. The base may be dimensioned to support a resected surface along the first end portion of the main body at the predetermined position such that an indicator along the second end portion of the main body may be aligned with a position along ruler. Each position along the ruler may be associated with a respective angle relative an axis. The axis may extend in the first direction from the predetermined position.

In a further implementation, the portion of the main body may include a first region that may be representative of cortical bone of the anatomy and a second region that may be representative of cancellous bone of the anatomy.

In a further implementation, the first end portion may include the first region. The first region may include at least one warning zone that may have an artificial color that may differ from a natural color of a respective portion of the anatomy.

A system for rehearsing a surgical procedure according to an implementation of the present disclosure includes, inter alia, a computing device including a processor coupled to memory. The processor may be configured to access a virtual anatomical model from the memory in response to selecting one or more parameters in a graphical user interface. The virtual anatomical model may be associated with an anatomy. The processor may be configured to cause the virtual anatomical model to be displayed in the graphical user interface. The processor may be configured to generate a configuration associated with a physical anatomical model that may be representative of the virtual anatomical model.

In a further implementation, the one or more parameters may include a patient classification and a defect category that may be associated with a plurality of virtual anatomical models in the memory.

In a further implementation, the configuration may establish a target zone and one or more warning zones that may cooperate to bound the target zone in the physical anatomical model. The configuration may include the target zone assigned a color that may correspond to a natural color of a respective portion of the anatomy. The configuration may include each warning zone assigned a respective artificial color that may establish a visual contrast with the natural color associated with the target zone.

In a further implementation, the processor may be configured to set at least one parameter that may be associated with the one or more warning zones of the virtual anatomical model in response to user interaction with the graphical user interface.

In a further implementation, the processor may be configured to compare one or more revisions of the physical anatomical model to the virtual anatomical model. The processor may be configured to generate an indicator in the graphical user interface in response to the one or more revisions meeting a predetermined threshold.

A method of rehearsing for a surgical procedure according to an implementation of the present disclosure includes, inter alia, defining a virtual anatomical model associated with an anatomy and forming a plurality of layers of material to establish a physical anatomical model that may be representative of the virtual anatomical model. The layers of material may establish a target zone and one or more warning zones that may bound the target zone. The target zone may have a color that may correspond to a natural color of a respective portion of the anatomy. Each warning zone may have a respective artificial color that may establish a visual contrast with the natural color associated with the target zone.

In a further implementation, the method may include selecting the virtual anatomical model from a plurality of virtual anatomical models stored in memory of a computing device.

In a further implementation, the step of selecting the virtual anatomical model may include selecting from a patient classification and selecting from a defect category in response to user interaction with a graphical user interface.

In a further implementation, the step of defining the virtual anatomical model may include setting one or more parameters of the virtual anatomical model associated with the one or more warning zones in response to user interaction with a graphical user interface.

In a further implementation, the forming step may include printing the layers of material on each other to establish the target zone and the one or more warning zones.

In a further implementation, the layers of material may have respective moduli of elasticity that substantially correspond to moduli of elasticity of respective portions of the anatomy.

In a further implementation, the one or more warning zones may include a plurality of warning zones in stacked relationship such that the warning zones may be offset at different distances from the target zone. The artificial colors of the warning zones may differ from each other to establish a visual contrast.

In a further implementation, the forming step may occur such that the warning zones may encircle the target zone.

In a further implementation, the method may include removing a portion of the physical anatomical model to expose the one or more warning zones.

In a further implementation, the method may include removing a portion of the physical anatomical model to establish a revised physical anatomical model. The method may include comparing the revised physical anatomical model to a predetermined geometry of the virtual anatomical model. The method may include generating an indicator in response to the removed portion of the physical anatomical model meeting a predetermined threshold.

Figure 1:
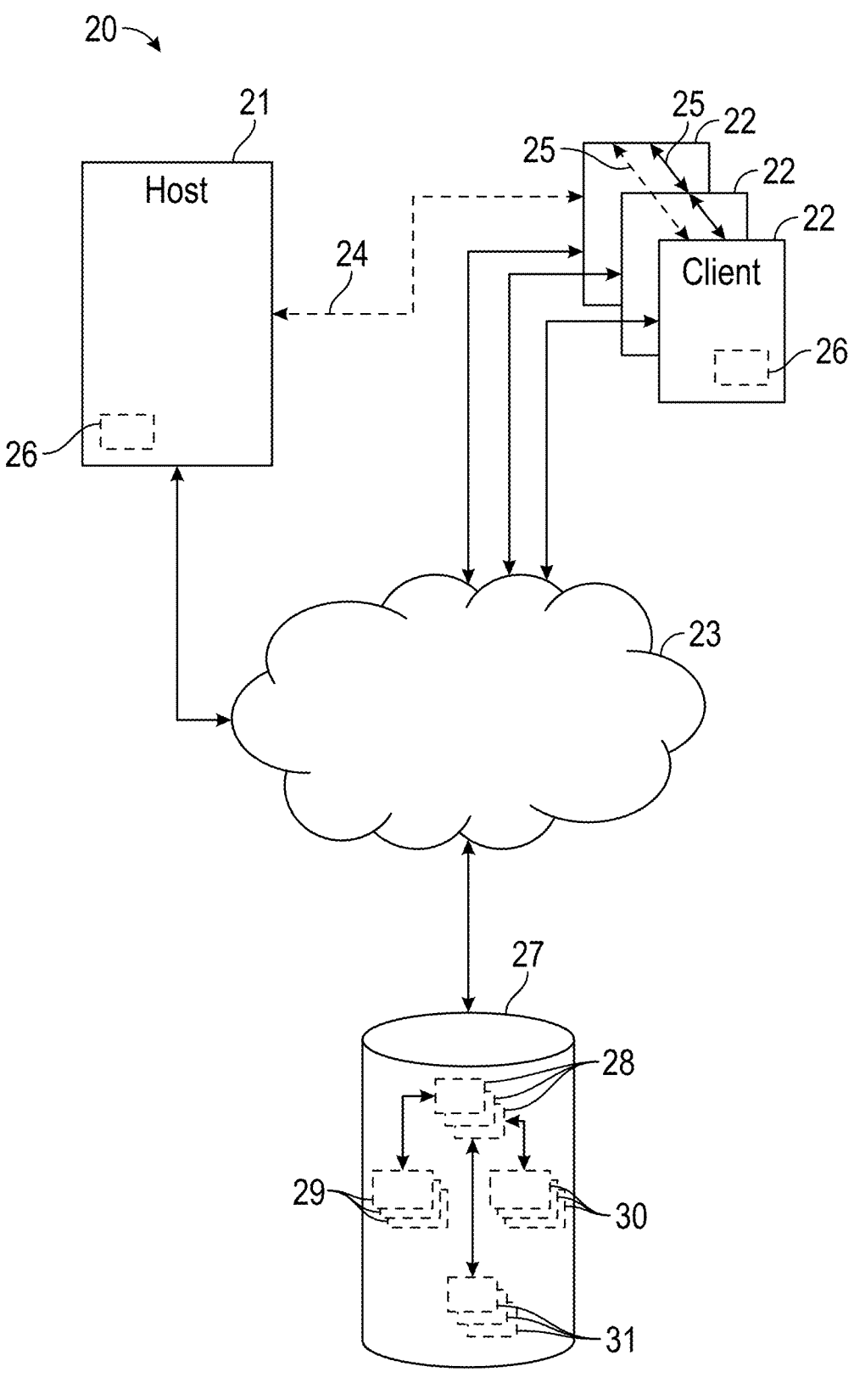
FIG. 1 illustrates an exemplary planning system.

FIG. 1 illustrates an exemplary planning system 20 that may be utilized for planning surgical procedures. The system 20 may be used for planning orthopaedic procedures, including pre-operatively, intra-operatively and/or post-operatively to create, edit, execute and/or review surgical plans. The system 20 may be used for training and rehearsing for various surgical procedures, including prior cases and surgical plans for patients.

The system 20 may include a host computer 21 and one or more client computers 22. The host computer 21 may be configured to execute one or more software programs. In some implementations, the host computer 21 is more than one computer jointly configured to process software instructions serially or in parallel.

The host computer 21 may be in communication with one or more networks such as a network 23 comprised of one or more computing devices. The network 23 may be a private local area network (LAN), a private wide area network (WAN), the Internet, or a mesh network, for example.

The host computer 21 and each client computer 22 may include one or more of a computer processor, memory, storage means, network device and input and/or output devices and/or interfaces. The input devices may include a keyboard, mouse, etc. The output device may include a monitor, speakers, printers, etc. The memory may, for example, include UVPROM, EEPROM, FLASH, RAM, ROM, DVD, CD, a hard drive, or other computer readable medium which may store data and/or other information relating to the features and techniques disclosed herein. The host computer 21 and each client computer 22 may be a desktop computer, laptop computer, smart phone, tablet, or any other computing device. The interface may facilitate communication with the other systems and/or components of the network 23.

Each client computer 22 may be configured to communicate with the host computer 21 directly via a direct client interface 24 or over the network 23. The client computers 22 may be configured to execute one or more software programs, such as various surgical tools. Each client computer 22 may be operable to access and locally and/or remotely execute a planning environment 26. The planning environment 26 may be a standalone software package or may be incorporated into another surgical tool. The planning environment 26 may be configured to communicate with the host computer 21 either over the network 23 or directly through the direct client interface 24. In another implementation, the client computers 22 are configured to communicate with each other directly via a peer-to-peer interface 25.

The planning environment 26 may provide a display or visualization of one or more virtual anatomical models 29 and related images and/or one or more implant models 30 via one or more graphical user interfaces (GUI). Each anatomical model 29, implant model 30, and related images and other information may be stored in one or more files or records according to a specified data structure.

The system 20 may include at least one storage system 27, which may be operable to store or otherwise provide data to other computing devices. The storage system 27 may be a storage area network device (SAN) configured to communicate with the host computer 21 and/or the client computers 22 over the network 23. In implementations, the storage system 27 may be incorporated within or directly coupled to the host computer 21 and/or client computers 22. The storage system 27 may be configured to store one or more of computer software instructions, data, database files, configuration information, etc.

In implementations, the system 20 may be a client-server architecture configured to execute computer software on the host computer 21, which may be accessible by the client computers 22 using either a thin client application or a web browser executing on the client computers 22. The host computer 21 may load the computer software instructions from local storage, or from the storage system 27, into memory and may execute the computer software using the one or more computer processors.

The system 20 may include one or more databases 28. The databases 28 may be stored at a central location, such as the storage system 27. In implementations, one or more databases 28 may be stored at the host computer 21 and/or may be a distributed database provided by one or more of the client computers 22. Each database 28 may be a relational database configured to associate one or more anatomical models 29 and/or one or more implant models 30 to each other and/or a surgical plan 31. Each surgical plan 31 may be associated with a respective patient. Each anatomical model 29, implant model 30 and surgical plan 31 may be assigned a unique identifier or database entry. The database 28 may be configured to store data corresponding to the anatomical models 29, implant models 30 and surgical plans 31 in one or more database records or entries, and/or may be configured to link or otherwise associate one or more files corresponding to each respective anatomical model 29, implant model 30 and surgical plan 31. Anatomical models 29 stored in the database(s) 28 may correspond to respective patient anatomies from prior and/or planned surgical cases, and may be arranged into one or more predefined categories such as sex, age, ethnicity, size, defect category, procedure type, etc. The anatomical models 29 and/or implant models 30 may be associated with respective instrumentation and devices to implement the associated surgical plan 31.

Each anatomical model 29 may include information obtained from one or more medical devices or tools, such as a computerized tomography (CT), magnetic resonance imaging (MRI) machine and/or X-ray machine, that obtains one or more images of a patient. The anatomical model 29 may include one or more digital images and/or coordinate information relating to an anatomy of the patient obtained or derived from the medical device(s). In implementations, one or more of the anatomical models 29 may be created by a designer and may represent a hypothetical anatomy. Each implant model 30 may include coordinate information associated with a predefined design. The planning environment 26 may incorporate and/or interface with one or more modeling packages, such as a computer aided design (CAD) package, to render the models 29, 30 as two-dimensional (2D) and/or three-dimensional (3D) volumes or constructs.

The implant models 30 may correspond to implants and components of various shapes and sizes. Each implant may include one or more components that may be situated at a surgical site including plates, anchors, screws, nails, suture, grafts, etc. Each implant model 30 may correspond to a single component or may include two or more components that may be configured to establish an assembly. Each anatomical model 29 and implant model 30 may correspond to 2D and/or 3D geometry, and may be utilized to generate a wireframe, mesh and/or solid construct in a display.

Each surgical plan 31 may be associated with one or more of the anatomical models 29 and/or implant models 30. The surgical plan 31 may include one or more revisions to the anatomical model 29 and information relating to a position of an implant model 30 relative to the original and/or revised anatomical model 29. The surgical plan 31 may include coordinate information relating to the revised anatomical model 29 and a relative position of the implant model 30 in predefined data structure(s). Revisions to each anatomical model 29, implant model 30 and surgical plan 31 may be stored in the database 28 automatically and/or in response to user interaction with the system 20.

One or more surgeons, assistants and other users may be provided with a planning environment 26 via the client computers 22 and may simultaneously access each anatomical model 29, implant model 30 and surgical plan 31 stored in the database(s) 28. Each user may interact with the planning environment 26 to create, view and/or modify various aspects of the surgical plan 31. Each client computer 22 may be configured to store local instances of the anatomical models 29, implant models 30 and/or surgical plans 31, which may be synchronized in real-time or periodically with the database(s) 28. The planning environment 26 may be a standalone software package executed on a client computer 22 or may be provided as one or more services executed on the host computer 21, for example.

Figure 2:
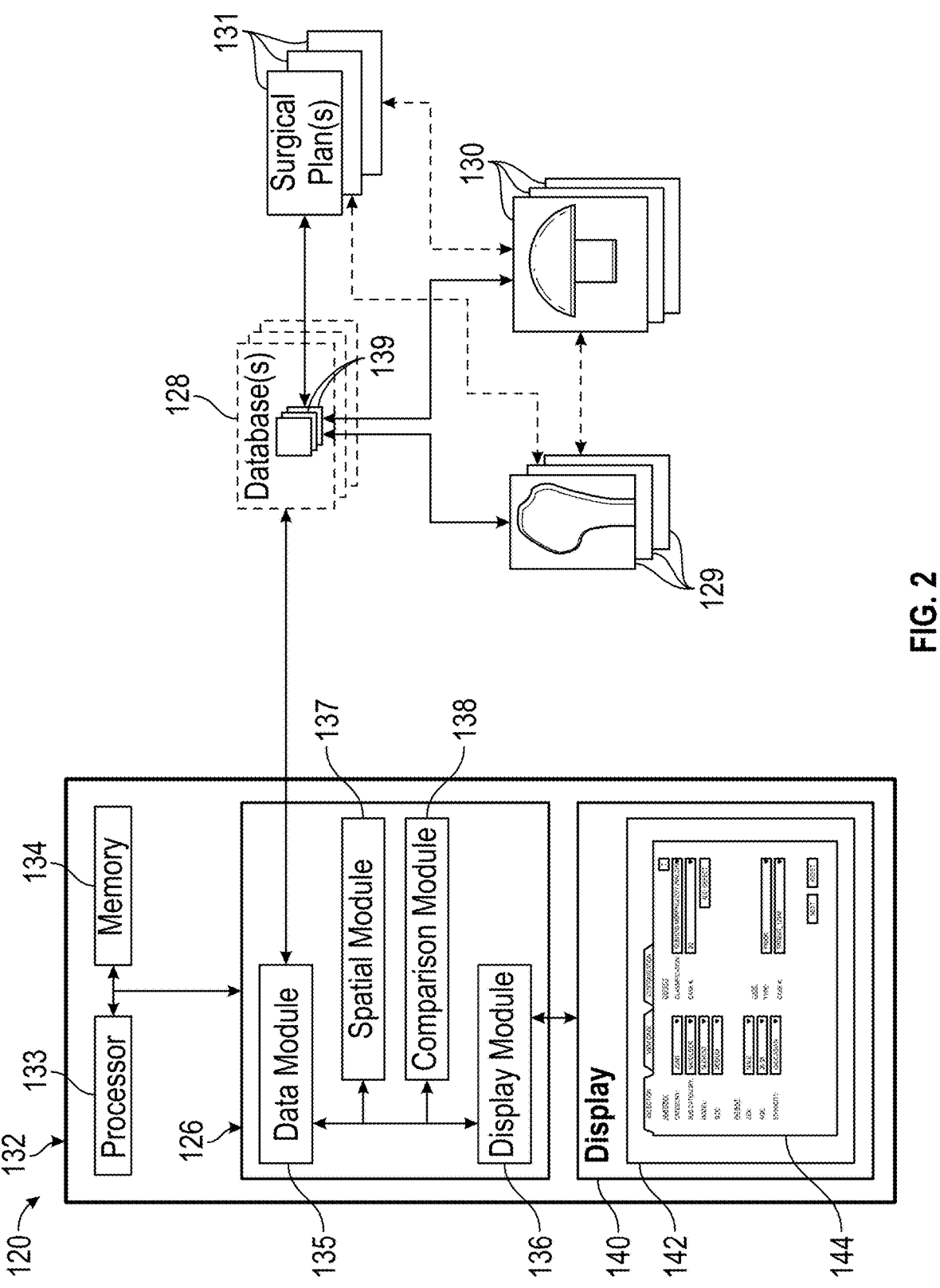
FIG. 2 illustrates another exemplary planning system including a user interface.

FIG. 2 illustrates a surgical system 120 for planning, rehearsal and/or training for a surgical procedure. The system 120 may be utilized to plan, rehearse, train and implement various orthopaedic and other surgical procedures, such as an arthroplasty to repair a joint. The system 120 may be utilized in planning a resection or revision of one or more bones. The system 120 may be utilized in planning placement of an implant to restore functionality to a joint, such as a shoulder joint during an anatomical or reverse shoulder procedure. Although the planning systems and methods disclosed herein primarily refer to repair of a shoulder, it should be understood that the planning system 120 may be utilized in the repair of other locations of the patient and other surgical procedures including repair of other joints such as an ankle, wrist, hand, hip or knee, and including repair of fractures and other tissue such as cartilage, muscles, tendons and ligaments.

The system 120 may be configured to generate configurations associated with respective physical anatomical models. The configuration may be utilized in the formation of the physical anatomical model. Each physical anatomical model may be representative of a virtual anatomical model 129, including a substantially corresponding geometry, density, porosity, color, etc. The surgeon may perform one or more modifications to the physical anatomical model to rehearse or train for a surgical procedure.

The system 120 may include a computing device 132 including at least one processor 133 coupled to memory 134. The computing device 132 can include any of the computing devices disclosed herein, including the host computer 21 and/or client computer 22 of FIG. 1. The processor 133 may be configured to execute a planning environment 126 for creating, editing, executing and/or reviewing one or more surgical (e.g., pre-operative) plans 131 during pre-operative, intra-operative and/or post-operative phases of a surgery. The anatomical model 129 and surgical plan 131 may be associated with an actual case for a patient or may be a hypothetical case established for training surgeons, assistants and medical staff.

The planning environment 126 may include at least a data module 135, display module 136, spatial module 137 and comparison module 138. The processor 133 may be configured to execute the data module 135, display module 136, spatial module 137 and comparison module 138. Although four modules are shown, it should be understood that fewer or more than four modules may be utilized and/or one or more of the modules may be combined to provide the disclosed functionality.

The data module 135 may be configured to access, retrieve and/or store data and other information in the database(s) 128 corresponding to one or more virtual anatomical model(s) 129, implant model(s) 130 and/or surgical plan(s) 131. The data and other information may be stored in the database 128 as one or more records or entries 139. In some implementations, the data and other information may be stored in one or more files that may be accessible by referencing one or more objects or memory locations referenced by the records 139.

The memory 134 may be configured to access, load, edit and/or store instances of one or more anatomical models 129, implant models 130 and/or surgical plans 131 in response to one or more commands from the data module 135. The data module 135 may be configured to cause the memory 134 to store a local instance of the anatomical model(s) 129, implant model(s) 130 and/or surgical plan(s) 131 which may be synchronized with records 139 in the database(s) 128.

The display module 136 may be configured to display data and other information relating to one or more surgical plans 131 in at least one graphical user interface (GUI) 142. The computing device 132 may be coupled to a display device 140. The display module 136 may be configured to cause the display device 140 to display information in the user interface 142. A surgeon or other user may interact with the user interface 142 via the planning environment 126 to create, edit and/or review aspects of one or more anatomical models 129. The surgeon or other user may interact with the user interface 142 via the planning environment 126 to create, edit, execute and/or review aspects of one or more surgical plans 131.

Each surgical plan 131 may be associated with one or more (e.g., original) virtual anatomical models 129 prior to any revisions, which may substantially approximate a patient anatomy. Each surgical plan 131 may be associated with one or more (e.g., revised) virtual anatomical models 129 incorporating one or more revisions to the patient anatomy and/or physical anatomical model. The original and revised anatomical models 129 may be associated with each other in the surgical plan 131. In implementations, the revisions are stored as one or more parameters of the original anatomical model 129.

The planning system 120 may be configured to generate a link to a surgical plan 131. The surgeon, assistant or other user may interact with the link to review and edit the surgical plan 131. Interacting with the link may cause the planning system 120 to display or otherwise present aspects of the surgical plan 131 in the graphical user interface 142.

Figure 3:
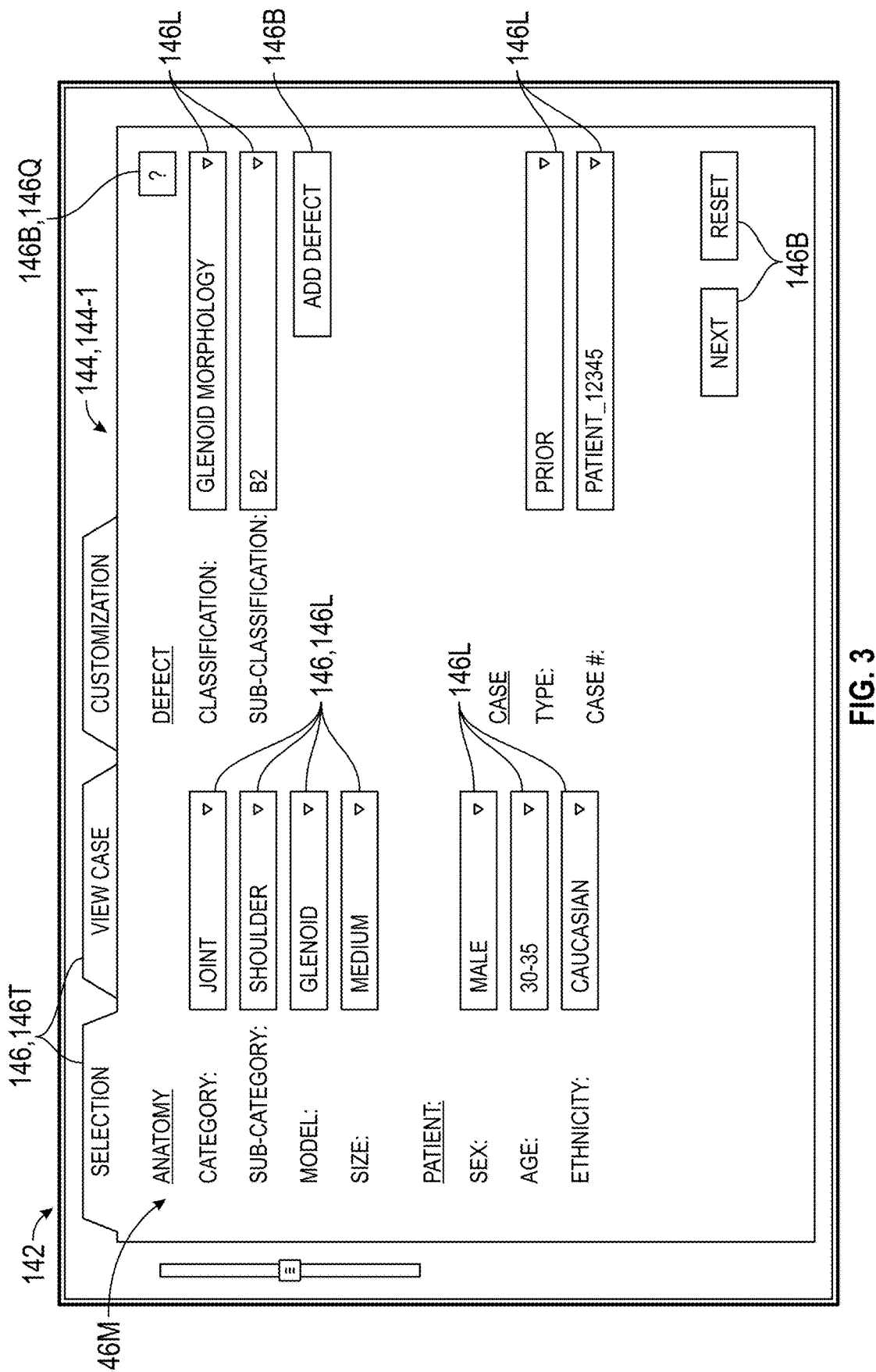
FIG. 3 illustrates the user interface of FIG. 2 including a display window including various parameters.

Referring to FIG. 3, with continuing reference to FIG. 2, the user interface 142 may include one or more display windows 144 and one or more objects 146. The objects 146 may include graphics such as menus, tabs and buttons accessible by user interaction, such as tabs 146T, buttons 146B, drop-down lists 146L, menus 146M, entry fields 146E (e.g., FIG. 7), directional indicators 146D, 146R (e.g., FIG. 5) and graphics 146G (e.g., FIG. 7). Geometric objects, including selected virtual anatomical model(s) 129 and implant model(s) 130 (e.g., FIG. 6), and other information relating to the surgical plan 131 may be displayed in one or more of the display windows 144.

The data module 135 may be configured to access a virtual anatomical model 129 from memory, such as the memory 134 and/or database 128, in response to selecting one or more parameters in a display window 144-1 of the graphical user interface 142. The anatomical model 129 may be associated with an anatomy of a patient, such as a prior case or a planned case. The display module 136 may be configured to select an anatomical model 129 from memory, such as the database 128 or memory 134, in response to user interaction with the display window 144-1 or another portion of the user interface 142.

Various parameters may be utilized to select an anatomical model 129. The parameters of the display window 144-1 may be interconnected to provide a filtering feature such that each selection of a parameter may cause the remaining parameter(s) to be filtered to depict available options. Each parameter may be associated with a set of anatomical models 129 accessible by the planning environment 126.

The surgeon may interact with the user interface 142 to select and review a desired case, such as a prior, planned or hypothetical case associated with a surgical plan 131. The surgeon may interact with the user interface 142 to review prior cases, including prior cases for a particular surgical procedure, anatomy and/or group of patients. The planning system 120 may be configured to provide analysis of the prior case such as biometric testing of a repaired joint, finite element analysis (FEA), etc. The surgeon may select a virtual anatomical model 129 corresponding to an intended patient. The selected model 129 may correspond to an acquired CT scan of the patient. The surgeon may select a virtual anatomical model 129 that may be associated with a particular classification.

The anatomical models 129 may be categorized by anatomy, patient, defect, case, etc. The parameters may include a patient classification and a defect category. Anatomical parameters may be arranged in one or more lists 146L by category (e.g., joint, etc.), sub-category (e.g., shoulder, ankle, hip, etc.), model (e.g., glenoid, humerus, etc.) and anatomical size (e.g., small, medium, large). The categories may be subdivided by gross anatomy including surface anatomy (e.g., the external body), regional anatomy (e.g., specific regions of the body), and systemic anatomy (e.g., specific organ systems). Patient parameters may include sex, age and ethnicity. The spatial module 137 may be configured to scale a geometry of the selected anatomical model 129 in response to selection of an anatomical size.

Figure 4:
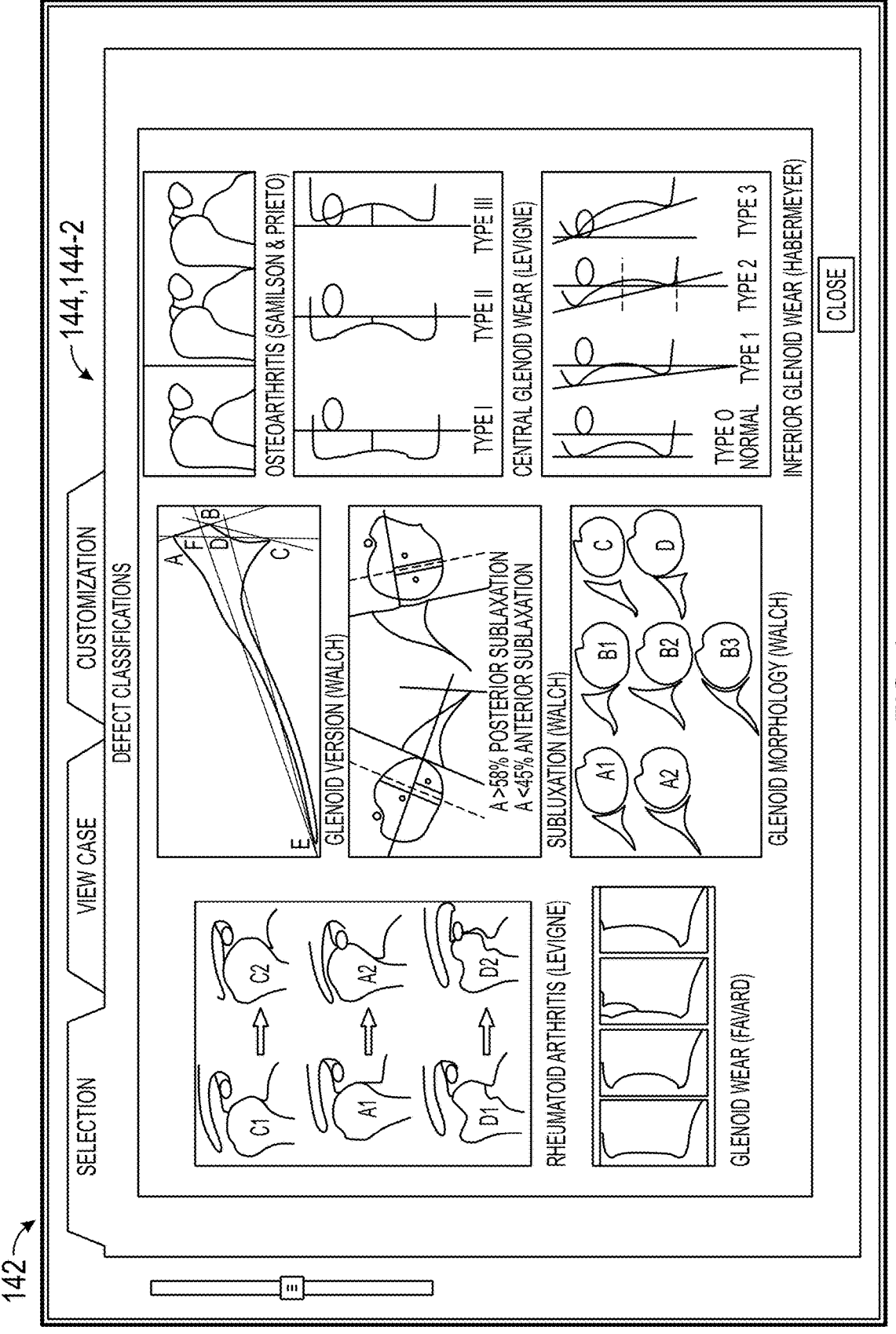
FIG. 4 illustrates a display window of the user interface of FIG. 2 including a help screen presenting exemplary defect classifications.

The surgeon may select the virtual anatomical model 129 according to a severity of various defects, such as mild, severe, non-pathological, fractures, etc. Defect parameters may be established for the various defects and may be arranged by classification, subclassification, etc. The surgeon, assistant or other user may interact with a button 146B (see, e.g., question mark button 146Q) for an explanation of the defect parameters, as illustrated by the display window 144-2 of FIG. 4. For example, selection of a glenoid model from the list 146L may cause a help screen to be generated and displayed with one or more defect classifications in response to selection of the button 146Q. As illustrated in FIG. 4, the defect classifications may include osteoarthritis including osteophytes associated with lateralization (see, e.g., Samilson and Prieto), central glenoid wear (see, e.g., Levigne), inferior glenoid wear and lateralization (see, e.g., Habermeyer), rheumatoid arthritis including superior wear and lateralization (see, e.g., Levigne), glenoid wear including superior wear (see, e.g., Favard), glenoid version (see, e.g., Walch), subluxation (see, e.g., Walch) and glenoid morphology including superior/inferior classification (see, e.g., Walch). The defect classifications of FIG. 4 are known, but utilization of the defect classifications as disclosed herein is not known. For example, the surgeon may select a relatively rare case such as a B2 or C2 classification of a glenoid based on information displayed in the help screen. The user may interact with a button 146B or another portion of the user interface 142 to specify more than one defect. The surgeon may select from the various classifications to determine various treatment options.

Case parameters may include case type (e.g., prior, planned and hypothetical), case number, etc. The user may interact with the lists 146L to select a particular case, which may be filtered based on previous selections of the parameters. Each case may be associated with a respective surgical plan 131. The surgical plan 131 may be associated with an anatomical model 129 prior to any revisions and may be associated with another (e.g., revised) anatomical model 129 incorporating one or more revisions based on implementation of an associated surgical procedure. Exemplary revisions may include removal of material utilizing one or more drilling, milling, resection, reaming and cutting operations.

Figure 5:
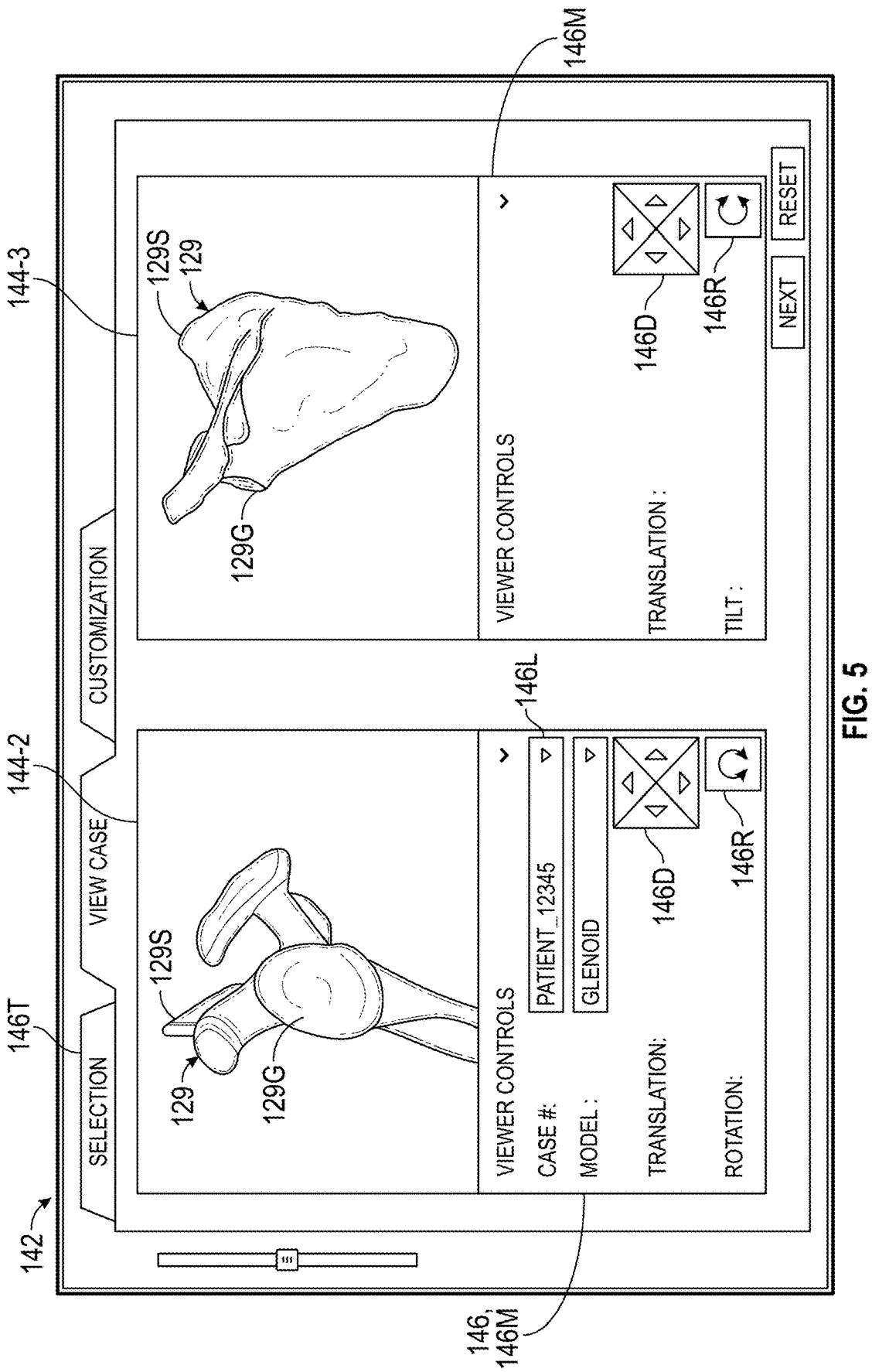
FIG. 5 illustrates the user interface of FIG. 2 including display windows depicting a virtual anatomical model.

Referring to FIG. 5, with continuing reference to FIGS. 2-3, the surgeon, assistant or other user may interact with the user interface 142 to view the selected anatomical model(s) 129 in display windows 144-2, 144-3 of the user interface 142. The data module 135 may be configured to cause the display module 136 to display the selected anatomical model(s) 129 in the user interface 142 in response to selection of the parameter(s). In the implementation of FIG. 5, the selected anatomical model 129 may be associated with a glenoid 129G of a shoulder joint 129S, although it should be understood that the system 120 may be utilized with various anatomy.

The display module 136 may be configured to display the selected anatomical model 129 at different positions and/or orientations in the display windows 144-2, 144-3. Although a particular number of display windows 144 are illustrated, it should be understood that the user interface 142 may be configured with any number of display windows 144 in accordance with the teachings disclosed herein. The display windows 144-2, 144-3 may be configured to display a two-dimensional (2D) and/or three-dimensional (3D) representation of the selected anatomical model 129. The user may interact with the user interface 142 to view the selected anatomical model(s) 129 at the various positions and orientations.

Figure 6:
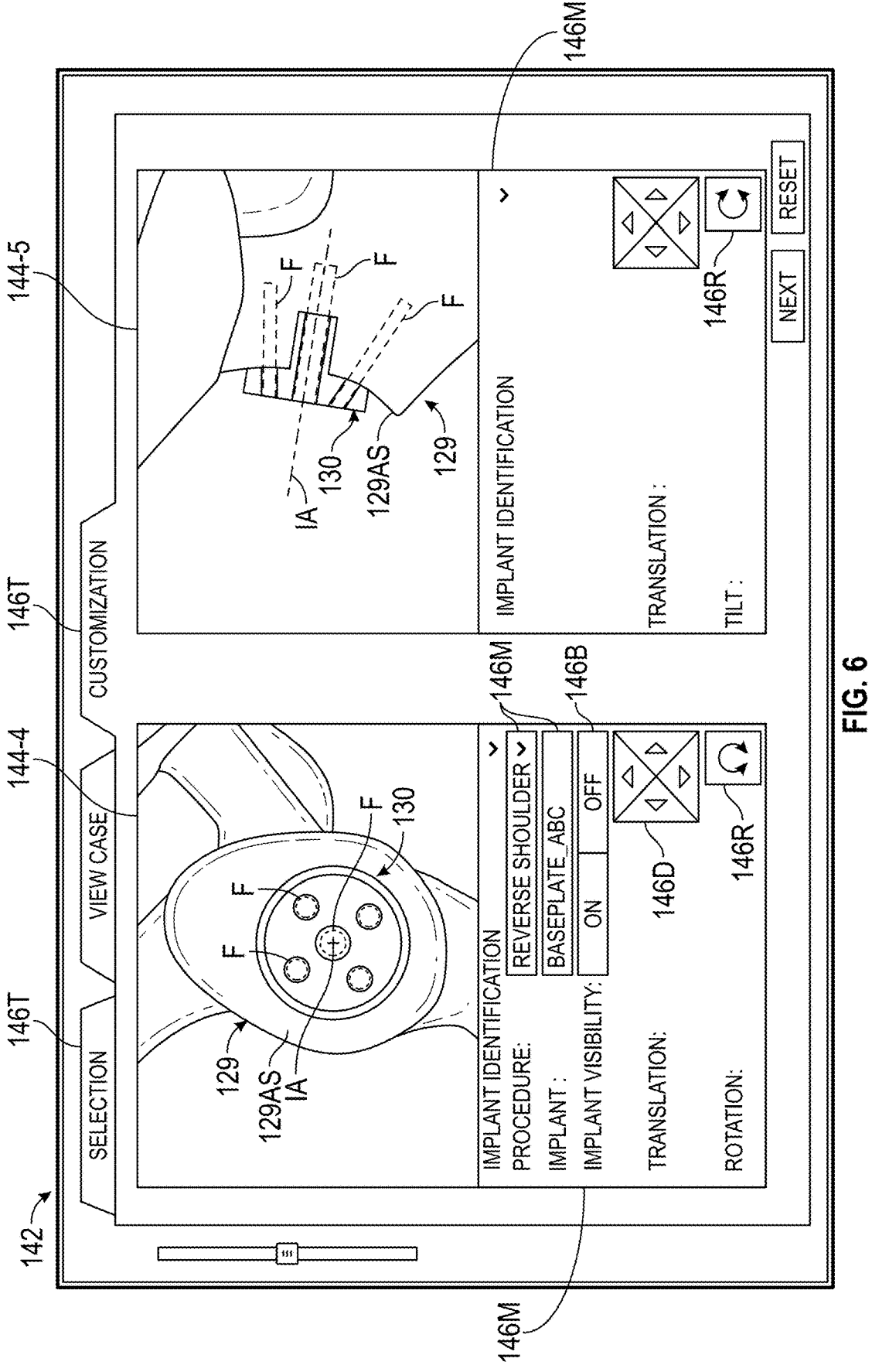
FIG. 6 illustrates the user interface of FIG. 2 including display windows depicting an implant model positioned relative to the virtual anatomical model of FIG. 5.

Referring to FIG. 6, with continuing reference to FIGS. 2 and 5, the surgeon, assistant or other user may interact with the user interface 142 to customize or otherwise specify one or more parameters associated with the selected anatomical model 129. The user may interact with the menus 146M, directly with display windows 144-4, 144-5, or with another portion of the user interface 142 to specify one or more aspects of, or modifications to, the surgical plan 131.

The user may interact with menu 146M or another portion of the user interface 142 to select one or more implant models 130 from a set of implant models 130 stored in memory such as the database 128 or memory 134. The data module 135 may be configured to access the selected implant model 130 automatically or in response to user interaction with the user interface 142. The data module 135 may be configured to store an instance of the virtual anatomical model and implant model 130 in the memory 134.

The implant models 130 may be associated with implants of various configurations, shapes, sizes, procedures, instrumentation, etc. The implant model 130 may include one or more components. Exemplary implants may include base plates coupled to an articulation member, bone plates configured to interconnect adjacent bones or bone fragments, intermedullary nails, suture anchors, etc. The articulation member may have an articular surface dimensioned to mate with an articular surface of an opposed bone or implant.

The display module 136 may be configured to display one or more selected virtual anatomical models 129 and/or implant models 130 in the display windows 144. The display module 136 may be configured such that the selected anatomical model 129 and/or implant model 130 may be selectively displayed and hidden (e.g., toggled) in one or more of the display windows 144 in response to user interaction with the user interface 142, which may provide the surgeon with enhanced flexibility in reviewing aspects of the surgical plan 131.

The display windows 144-4, 144-5 may be configured to display the selected anatomical model 129 and implant model 130 relative to each other. The spatial module 137 may be configured to position the selected implant model(s) 130 into contact with the anatomical model(s) 129 at a specified or defined position and orientation. The implant model 130 may be positioned relative to a surface of the anatomical model 129, such as an articulation surface 129AS which may be associated with an articular surface of a bone. The user may interact with the menus 146M, directly with the display windows 144-4, 144-5, or with another portion of the user interface 142 to position and orient the selected implant model 130 relative to the anatomical model 129, including an implant axis IA of the implant model 130. The user may interact with the menu 146M, the display windows 144-4, 144-5 or another portion of the user interface 142 to move the selected anatomical model 129 and/or selected implant model 130 in 2D space (e.g., up, down, left, right) and/or 3D space (e.g., rotation, tilt, zoom, etc.), which may occur in response to interaction with the directional indicators 146D, 146R.

The display module 136 may be configured to display one or more fastener models F (shown in dashed lines). The fastener models F may be associated with respective fasteners configured to secure an implant associated with the selected implant model 130.

Figure 7:
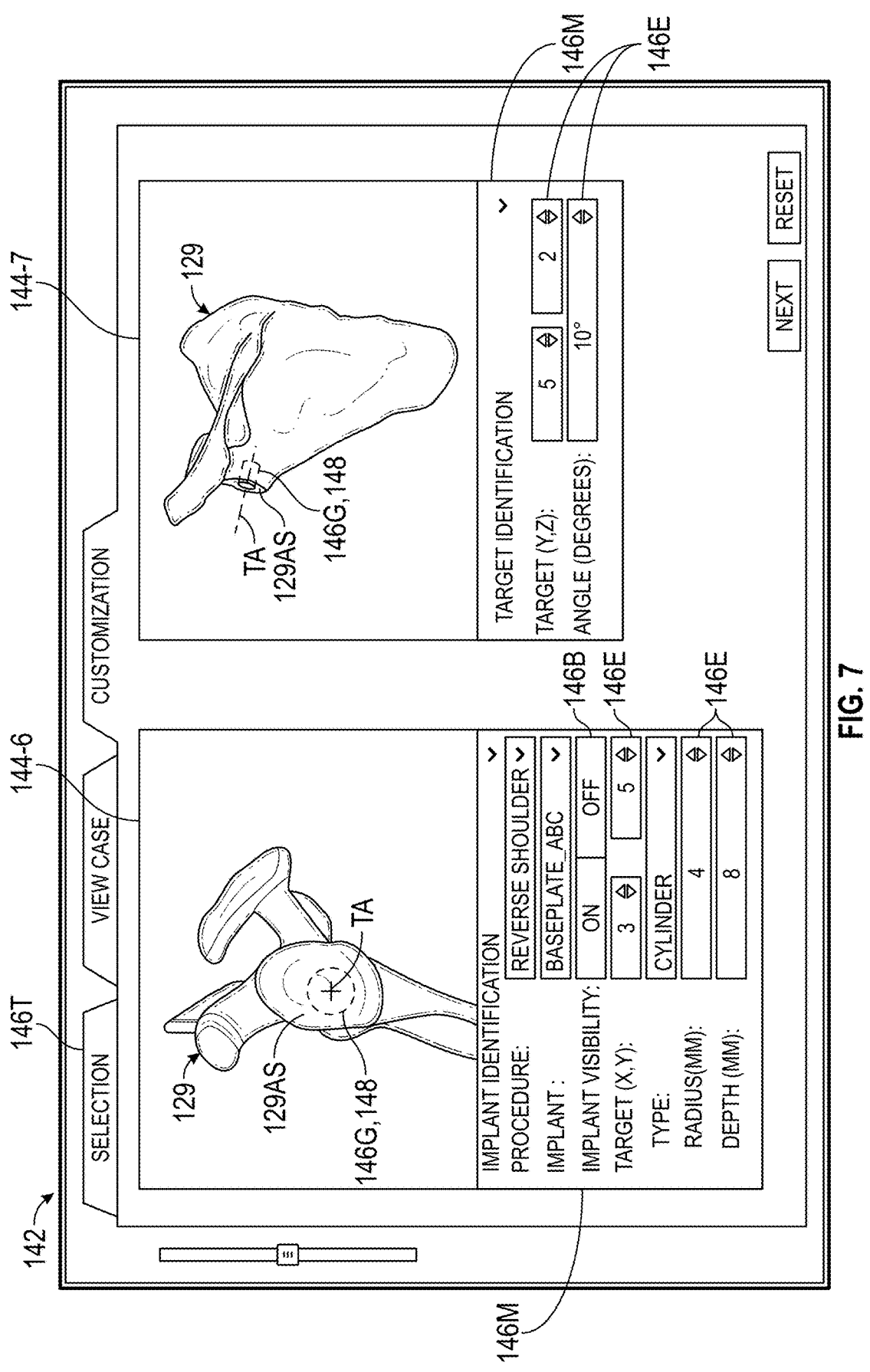
FIG. 7 illustrates a target zone established relative to the virtual anatomical model of FIG. 5.

Referring to FIG. 7, with continuing reference to FIGS. 2 and 5-6, the surgeon, assistant or other user may interact with the user interface 142 to customize the selected anatomical model(s) 129. The display windows 144 may include display windows 144-6, 144-7. The user may interact with the menu 146M to toggle on and off visibility of the selected implant model 130.

The surgeon may desire to specify one or more zones (e.g., regions) associated with a surgical procedure. The zones may be formed in an associated physical anatomical model to provide feedback to the surgeon. In implementations, the feedback may include one or more visual, audible and/or tactile indicators in response to interaction.

The spatial module 137 may be configured to establish one or more target zones (e.g., localized regions) 148. The user may interact with the menus 146M, display windows 144-6, 144-7 or another portion of the user interface 142 to establish the target zone(s) 148. Each target zone 148 may be established along any portion of the virtual anatomical model 129. In implementations, the target zone 148 may extend along the articulation surface 129AS of the anatomical model 129.

The user may interact with the user interface 142 to specify various aspects of the target zone 148. The target zone 148 may have various 3D geometries, including cones, cylinders, cubes and cuboids, prisms, pyramids, spheres, complex geometries, etc. The spatial module 137 may be configured to assign a default geometry of the target zone 148 based on the selected anatomical model 129, implant model 130, surgical plan 131 and/or other parameters selected by the user (see, e.g., FIG. 3). Each target zone 148 may be dimensioned to approximate a portion of a volume of the selected implant model 130. The target zone 148 may be dimensioned for positioning a fixation member such as an anchor or post of the selected implant model 130 (see, e.g., FIG. 6). Each target zone 148 may be associated with a respective graphic 146G. The graphic 146G may have a geometry that substantially corresponds to a geometry of the target zone 148.

The user may interact with the user interface 142 to specify a position and orientation of a target axis TA associated with the target zone 148. The spatial module 137 may be configured to set a position and orientation of the target axis TA to be substantially collinear with or otherwise substantially parallel to an implant axis IA of the implant model 130 (FIG. 6). For the purposes of this disclosure, the terms "substantially," "about" and "approximately" mean ±5 percent of the stated value or relationship unless otherwise indicated. The user may interact with the menu 146M to specify one or more dimensions of the target zone 148, including width, length, depth, radius, etc., based on a geometry of the target zone 148.

Figure 8:
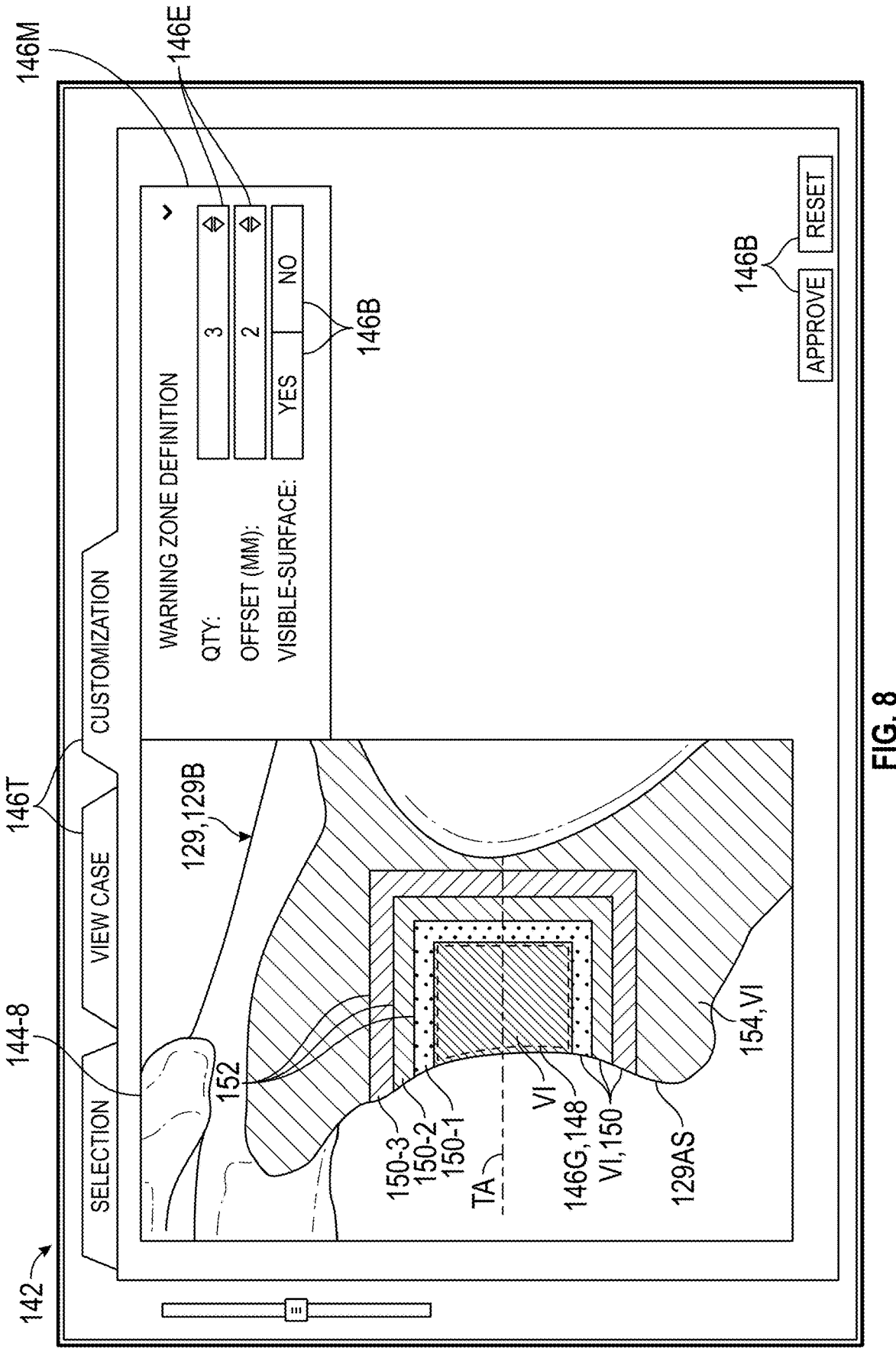
FIG. 8 illustrates warning zones established relative to the target zone of FIG. 7.

Referring to FIG. 8, with continuing reference to FIGS. 2 and 7, the spatial module 137 may be configured to establish one or more warning zones 150. The warning zones 150 may be generated manually or automatically in response to establishing the respective target zone(s) 148. The warning zones 150 may be established according to the selected parameters, including the selected anatomy, procedure type, defect classification(s), case, etc. The warning zones 150 may be procedure specific and/or pathological specific. The display module 136 may be configured to display the warning zones 150 relative to the selected anatomical model 129 in a display window 144-8. The spatial module 137 may be configured to establish a third zone 154. The third zone 154 may include a remainder of a volume of the anatomical model 129 excluding the target zone(s) 148 and warning zone(s) 150.

The target zone(s), warning zone(s) 150 and/or third zone 154 may be established by a main body 129B of the virtual anatomical model 129. The warning zones 150 may be established along an external surface of the anatomical model 129 and/or within a thickness of the anatomical model 129 underlying the external surface, such as the articulation surface 129AS. The surgeon, assistant or other user may interact with the user interface 142 to specify whether or not the warning zones 150 are visible along an external surface of the anatomical model 129. In the implementation of FIG. 8, the warning zones 150 may include three warning zones 150-1 to 150-3 that may extend inwardly from the articulation surface 129AS. The warning zones 150-1 to 150-3 may serve to provide the surgeon a visual indication of a proximity to the target zone 148. External warning zones may present less of a challenge to the surgeon. The surgeon may select to have warning zones only formed below the external surface of the anatomical model, which may more closely approximately a surgical procedure on the anatomy and may be relatively more challenging.

The planning environment 126 may be configured such that at least one or more parameters associated with the warning zones 150 may be set in response to user interaction with the user interface 142. The user may interact with the menu 146M, directly with the display window 144-8, or with another portion of the user interface 142 to define each of the warning zones 150. Various parameters associated with warning zones 150 may be utilized, including quantity, offset (e.g., thickness), etc.

The warning zones 150 may correspond to a plurality of layers 152 in stacked relationship such that the warning zones 150 are offset at different predefined distances from the target zone 148. In implementations, the warning zones 150 and respective layers 152 may be established at increasing offsets from a perimeter of the target zone 148. The thicknesses of the warning zones 150 may be the same or may differ. In the implementation of FIG. 8, a quantity of three warning zones 150 may be established (indicated at 150-1, 150-2, 150-3) adjacent to the target zone 148. Although three warning zones 150 are shown, it should be understood that fewer or more than three warning zones 150 may be established for each target zone 148, such as only one warning zone 150. The warning zones 150 and respective layers 152 may substantially encircle or otherwise bound the target zone 148 to establish a boundary for performing a surgical procedure.

The warning zones 150 may visually contrast with each other and/or the target zone 148 to provide the surgeon with an indication of an amount of deviation from the target zone 148. For example, the surgeon may perform a drilling operation that may extend through the target zone 148 and into one or more of the warning zones 150. The warning zones 150 may serve to indication an amount of excess depth of the drilling operation. The display module 136 may be configured to display a visual contrast between the warning zones 150 and a remainder of the anatomical model 129, including the target zone(s) 148 and third zone 154. In implementations, the visual contrast may be established by one or more visual indicators VI applied to the respective target zone 148, warning zones 150 and/or third zone 154 (shown in hatching for illustrative purposes). In implementations, the target zone(s) 148 and/or third zone(s) 154 may omit any visual indicators VI (see, e.g., FIG. 9).

The target zone(s) 148, warning zones 150 and third zone 154 may be established according to one or more visual or color schemes. In implementations, the target zone 148 and/or third zone 154 may be assigned a color that corresponds to a natural color of a respective portion of the anatomy. The warning zones 150 may be assigned one or more artificial colors to establish a visual contrast. The visual contrast may assist the surgeon in identifying the target zone 148 and any deviations from the target zone 148 into the warning zones 150. For the purposes of this disclosure, the term "natural" color means a color that substantially corresponds to an expected or actual color of the respective tissue, and the term "artificial" color means a color that does not naturally occur for the respective tissue.

Each warning zone 150 may be assigned a respective artificial color that may differ from a natural color of a respective portion of the anatomy and that may establish a visual contrast with the natural color associated with the target zone 148. The artificial colors of the warning zones 150 and associated layers 152 may be the same or may differ from each other. The respective colors of the warning zones 150-1 to 150-3 are shown in hatching for illustrative purposes. Exemplary artificial colors may include yellow, orange, red, green, blue, etc. In other implementations, the warning zones 150 may be assigned a color that substantially corresponds to a natural color of a respective portion of the anatomy, but that may have a shade that differs by at least 10 percent or more from the natural color to establish a visual contrast.

Figure 9:
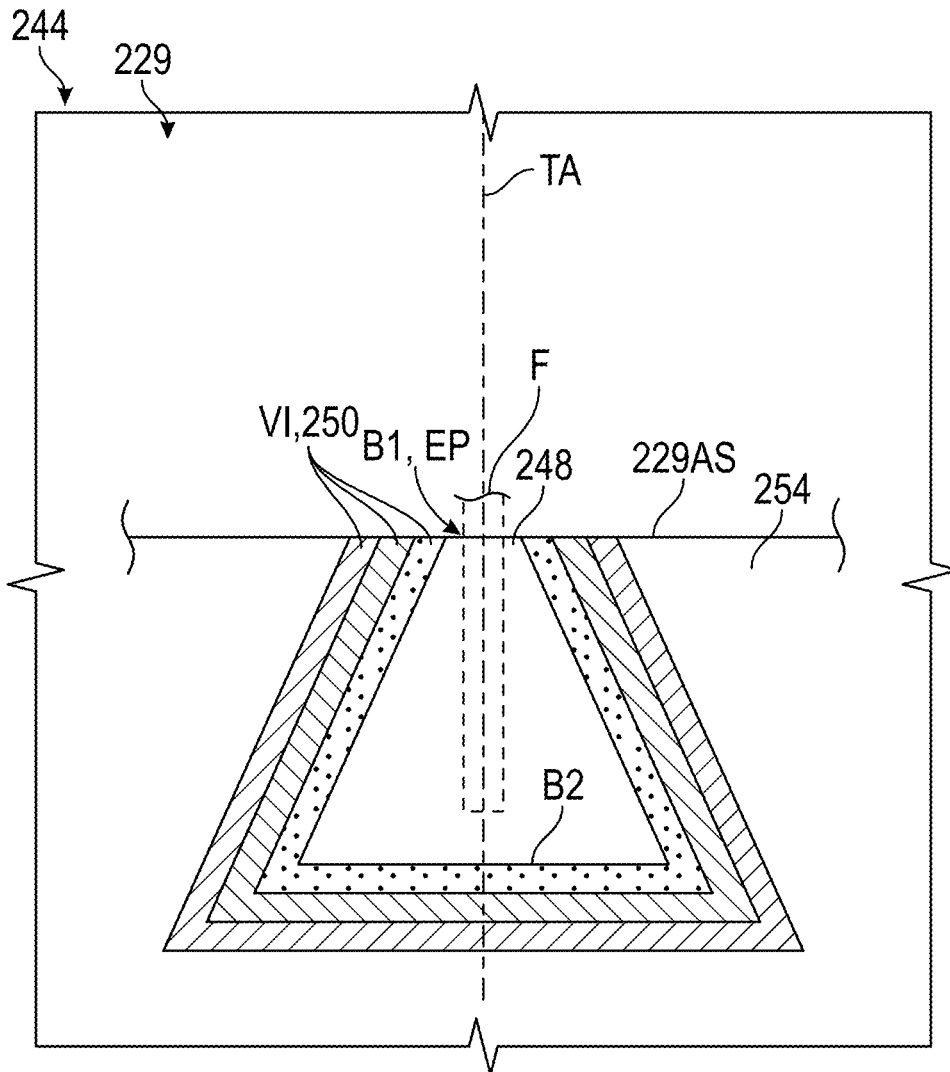
FIG. 9 illustrates another virtual anatomical model in a graphical user interface.

The target zone(s) 148 and warning zone(s) 150 may have other configurations. In the implementation of FIG. 9, the virtual anatomical model 229 may have a main body 229B. A target zone 248 and one or more warning zones 250 may be established in the main body 229B. The target zone 248 may have a substantially truncated conical geometry having a first base B1 and a second base B2. The first base B1 may have a radius that differs from (e.g., is less than) a radius of the second base B2. The first base B1 may establish an entry point EP along an external surface of the main body 229B. The entry point EP may be substantially aligned with a target axis TA. The external surface may be established by an articulation surface 229AS of the selected anatomical model 229. The target axis TA may be associated with a suitable trajectory of a portion of an implant and/or fastener. The entry point EP may be representative of safe passage for a surgical device through a portion of the tissue. The entry point EP may be dimensioned to receive a fastener model F (shown in dashed lines). Walls of the target zone 248 may be sloped to limit a range of angles of the fastener model F relative to the target axis TA. The warning zones 250 may extend along the second base B2 to bound a height of the target zone 248 and an insertion depth of the fastener model F.

In the implementation of FIGS. 10-11, a volume of target zone 348 may have a substantially cuboid geometry with a substantially rectangular perimeter. Target zone 348 and warning zones 350 may be spaced apart from an external surface of a main body 329B of the anatomical model 329, which may be established by an articulation surface 329AS. The warning zones 350 may be configured to substantially surround the target zone 348 as a set of concentric loops.

In the implementation of FIG. 12, the target zone(s) 448 and warning zone(s) 450 may be lateralized relative to an external surface of a virtual anatomical model 429. A graphical user interface 442 may include display windows 444-8, 444-9. The display window 444-8 may be configured to display a sectional view of the anatomical model 429 relative to a reference plane REF1 (shown in dashed lines). The display window 444-9 may be configured to display a perspective view of the anatomical model 429 sectioned along the reference plane REF1.

Target zone(s) 448, warning zone(s) 450 and/or third zone(s) 454 may be established in a volume of a main body 429B of the anatomical model 429. The target zone 448 may be established along, and may extend inwardly from, an external surface of the main body 429B. The external surface may be an articular surface 429AS associated with a joint of the respective anatomy.

The warning zones 450 may be lateralized and may correspond to various reaming depths. The warning zones 450 may indicate that an implemented reaming depth may be insufficient and/or excessive. The warning zones 450 may include warning zones 450-1 to 450-3 established by respective layers 452. The warning zones 450 may be established below the external surface of the main body 429B. The warning zones 450 and respective layers 452 may be offset at different depths from the target zone 448 and/or external surface of the main body 429B.

The target zone 448 and warning zones 450 may be representative of bone tissue associated with the anatomy. The target zone 448 may be representative of cortical bone associated with the anatomy, such as cortical bone along an articular surface of a glenoid. The third zone 454 may establish a non-cortical region representative of cancellous or trabecular bone associated with the anatomy. The target zone 448 and third zone 454 may be assigned a color that closely approximates the cortical and trabecular bone of an anatomy of a patient, respectively. The layers 452 may be arranged such that the warning zones 450 are established between the target zone 448 and third zone 454. In implementations, the warning zones 450-1 to 450-3 may correspond to depths of 1 mm, 2 mm and 3 mm below the target zone 448.

In the implementation of FIG. 13, a target zone 548 may be established between one or more warning zones 550. The warning zones 550 may be formed by respective layers 552. The layers 552 may be substantially parallel and may have substantially the same thicknesses, or the thicknesses may differ. The layers 552 may include a first set of layers 552-1 and a second set of layers 552-2. The first set of layers 552-1 may establish warning zones 550-1 to 550-3. The second set of layers 552-2 may establish warning zones 550-4 to 550-6. The target zone 548 may be established between the first and second sets of layers 552-1, 552-2. The target zone 548 may be associated with an intended resection plane that may be engaged with a reciprocating or oscillating saw to form a cut along a long bone such as a proximal portion of a tibia or a distal portion of a femur, for example.

The physical anatomical model may include other representative tissue incorporating warning zones. Certain procedures may include navigating into and through 3D muscular intervals. The procedure may including navigating through and in between the layers without violating the muscular structure (e.g., separating without cutting). For example, a surgeon planning for a hip arthroplasty may desire to minimize or otherwise reduce injury to the soft tissue. The warning zones may confine a particular region of a physical anatomical model of the soft tissue so that the surgeon may be required to open up the representative soft tissue without ripping the representative soft tissue. If the surgeon cuts through the representative soft tissue, the warning zone may be presented to the surgeon. The surgeon may excise the representative soft tissue along natural boundaries to avoid the warning zones. The warning zones may not be visible on the external surface of the representative soft tissue. If surgeon deviates to a side of the zone, the warning zone may be revealed.

Referring to FIG. 14, with continuing reference to FIG. 2, the virtual anatomical model 629 may include bone and other tissue, including soft tissue. The soft tissue may include tendon, ligament and/or muscle tissue including one or more fibers. The user interface 642 may include display windows 644-10, 644-11 configured to display the anatomical model 629. The display window 644-11 may be configured to display a section of the anatomical model 629 with respect to a reference plane REF2 (shown in dashed lines).

The spatial module 137 may be configured to establish one or more target zones 648 and warning zone 650. The target zone(s) 648 and warning zone(s) 650 may be representative of soft tissue associated with the anatomy. A third zone 654 may be established, which may be representative of relatively hard tissue such as cartilage and/or bone tissue.

The anatomical model 629 may include one or more fibers 656 associated with fibers of the anatomy. A bundle of fibers 656 may be formed along, may extend from, or may be arranged adjacent to a main body 629B. The bundle of fibers 656 may be representative of the soft tissue, such as muscle tissue. The target zones 648 and warning zones 650 may cooperate to establish the bundle of fibers 656. The display module 136 may be configured to display the fibers 656 in plan and sectional views, as illustrated in the display windows 644-10, 644-11, respectively. One or more target zones 648 may be established in the fibers 656 and/or between adjacent fibers 656.

Each of the fibers 656 may include an internal core 656C and an outer sheath 656S. The sheath 656S may substantially surround the core 656C. One or more target zones 648 may be established between adjacent fibers 656. The target zones 648 may be representative of a pathway between the adjacent fibers 656. The core 656C may establish a respective one of the warning zones 650. The sheath 656S may substantially surround at least one warning zone 650 of the respective fiber 656. In implementations, sheaths 656S of the adjacent fibers 656 may establish the respective target zone 648.

The external surface established by the sheath 656S of each fiber 656 may be assigned a color substantially corresponding to a natural color of the respective tissue. The core 656C may be assigned an artificial color that may differ from a natural color of the respective tissue such that the target zone(s) 648 and warning zone(s) 650 visually contrast each other.

In the implementation of FIG. 15, a bundle of fibers 756 may include first, second and third set of fibers 756-1, 756-2, 756-3. The first set of fibers 756-1 may establish a target zone 748. Each fiber 756 of the second and third sets of fibers 756-2, 756-2 may establish a respective warning zone 750. Individual target zones 748 may be established by respective fibers 756. Individual warning zones 750 may be established by a core and/or sheath of the respective fiber 756. The second and third sets of fibers 756-2, 756-3 may be established on opposed sides of the first set of fibers 756-1 such that the first set of fibers 756-1 establishes a localized region or pathway.

In the implementation of FIG. 16, a graphical user interface 842 may include a display window 844-12 configured to display an anatomical model 829. The anatomical model 829 may be associated with one or more tissue types, including bone, cartilage, tendons, ligaments, muscle tissue, etc. The anatomical model 829 may include bundles of fibers 856 that establish one or more muscle groups 858. The muscle groups 858 may be associated with one or more target zones 848 and/or warning zones 850. In the implementation of FIG. 16, the anatomical model 829 may be representative of a shoulder joint including one or more of the muscle groups 858.

The surgeon, assistant or other user may interact with menus 846M, directly with the display window 844-12 or another portion of the user interface 842 to set each of the muscle groups 858 as a target zone 848 or warning zone 850. In the implementation of FIG. 16, the target zone 848 may be associated with a lateral head of a deltoid, warning zone 850-1 may be associated with a posterior head of the deltoid, and warning zone 850-2 may be associated with an anterior head of the deltoid. In another implementation, a portion of a virtual anatomical model associated with a deltoid may be selected as a first warning zone assigned a first color (e.g., red), a teres minor may be selected as a second warning zone assigned a second color (e.g., blue), and a region in between the deltoid and teres minor may be selected as a target zone assigned a third color (e.g., green). Utilizing the techniques disclosed herein, the surgeon may interact with a physical anatomical model formed from a construction defined by the virtual anatomical model 829 as a training tool to help the surgeon navigate or guide instruments through the muscle during a shoulder arthroplasty.

Referring back to FIG. 2, the surgeon, assistant or other user may interact with the user interface 142 to approve selections of the various parameters associated with the selected virtual anatomical model 129. In implementations, the user may select a button 146B to approve the selections and other parameters associated with the virtual anatomical model 129 (see, e.g., FIG. 8).

The spatial module 137 may be configured to generate a configuration (e.g., definition) associated with a physical anatomical model. The configuration may be representative of the virtual anatomical model 129. The configuration may be established according to the selection of the parameters associated with the selected virtual anatomical model 129, including any target zones 148 and warning zones 150 (see, e.g., FIG. 8). The configuration may be a file stored in, or linked to, a record 139 in the database 128. The configuration may include data and other information sufficient to establish the physical anatomical model based on a geometry and the parameters of the selected virtual anatomical model 129, including coordinate information, moduli of elasticity of the associated tissues, color schemes associated with target zones 148 and warning zones 150, etc.

The physical anatomical model may be formed subsequent to selecting and approving the virtual anatomical model 129 and the various parameters. The physical anatomical model may be representative of various tissue including bone tissue and soft tissue. The physical anatomical model may have a construction that is representative of anatomy, including joints, bones, muscle, tendons, ligaments, internal organs, etc. The physical anatomical model may be configured to provide indicators or feedback to the surgeon prior to, during and/or subsequent to execution of a surgical procedure. The feedback may be patient or non-patient specific. In implementations, the planning system 120 may be configured to provide verbal or visual feedback such as a prompt for the surgeon to aim for a specific area of bone or soft tissue.

Various techniques may be utilized to construct or otherwise form the physical anatomical models disclosed herein, including the physical anatomical model 960. The physical anatomical models may be constructed or otherwise formed utilizing any of the techniques disclosed herein, and may incorporate any of the features disclosed herein including a geometry of the respective virtual anatomical model(s), moduli of elasticity of the associated tissue(s), color scheme(s) and geometries associated with the target zone(s) and/or warning zones, layer and fiber arrangements, etc. The physical anatomical model may be formed to closely resemble or approximate a geometry of the associated anatomy, including soft tissue and bone. In implementations, the surgeon may interact with the physical anatomical model such that portion(s) of the physical anatomical model may feel similar to soft (e.g., cancellous) bone tissue. The physical anatomical model may be printed or otherwise formed according to the various parameters selected in the user interface. Various parameters may be utilized to form the physical anatomical model, including any of the parameters disclosed herein, such as density of bone and soft tissue, thickness of cortical bone, target and warning zones, patient age, etc.

The planning system 120 may configured to cause the virtual anatomical model 129 to be printed or otherwise formed based on the selected parameters. In implementations, material may be printed in one or more layers on a substrate to establish the physical anatomical model. The material may be printed according to the configuration associated with the virtual anatomical model. In other implementations, the physical anatomical model is established by one or more casting operations. The physical anatomical model may have a unitary construction or may have two or more components fixedly attached or otherwise secured to each other to establish a unit.

Referring to FIG. 17A, with continuing reference to FIG. 2, an implementation of a physical anatomical model 960 is shown. FIG. 17B is a grayscale image of the physical anatomical model 960. The physical anatomical model 960 may be associated with any of the anatomy disclosed herein.

The anatomical model 960 may include portions 962, 964, 966. The portion 962 may establish a main body 960B and may be representative of bone tissue, such as a portion of a humerus including the humeral head. The portions 964 may be formed on, or may otherwise extend from, the portion 962 and may be representative of soft tissue such as one or more tendons. The tendons may be associated with a rotator cuff. The portions 966 may extend from the respective portions 964 and may be representative of muscle tissue.

Various materials may be utilized to form the physical anatomical models disclosed herein, including the physical anatomical model 960. In implementations, the portion 962 establishing the main body 960B may be formed from a substantially rigid material, such as a polymeric material, including photopolymers, silicones and thermoplastics. Each of the fibers of the portions 964, 966 may be formed from a relatively flexible material, including an elastomeric material such as rubber or silicone.

Referring to FIGS. 18-19, with continuing reference to FIG. 17A, the physical anatomical model 960 may be incorporated into an assembly (e.g., training device) 968. The assembly 968 may include one or more fixtures (e.g., jigs) 970. Each fixture 970 may be reusable or may be single use. Each fixture 970 may be representative of surrounding tissue or a portion of a joint. A first fixture 970-1 may be representative of a portion of a humerus. A second fixture 970-2 may be representative of a portion of a shoulder such as a glenoid or an implant having an articular surface dimensioned to establish a joint. The physical anatomical model 960 may be mounted or otherwise secured to one or more of the fixtures 970 at an interface 972. The interface 972 may be established by an interference fit, a quick release connection or fasteners. The surgeon may utilize the fixtures 970 to simulate rotating or moving a limb in an operating room. The assembly 968 may include a fixture 970-3 representative of skin tissue, as illustrated in FIG. 19. The fixture 970-3 may be formed from a relatively flexible material, such as an elastomeric material. The surgeon may form one or more openings 974 in the fixture 970-3 to simulate performing an incision to expose a joint or another portion of the anatomy.

Referring to FIGS. 20-21, with continuing reference to FIG. 17, the surgeon may perform one or more modifications to the physical anatomical model 960, as illustrated by physical anatomical model 1060. The surgeon may perform a resection along a reference plane REFS, which may simulate resecting a portion of an articulation surface 1060AS, which may be associated with a humeral head (shown in dashed lines in FIG. 19). The resection may expose a first region R1 and a second region R2 (FIG. 20). The first region R1 may be substantially solid. The second region R2 may be relatively porous. The first region R1 may be representative of cortical bone. The second region R2 may be representative of cancellous bone.

FIGS. 22-23 are grayscale images of another physical anatomical model including portions corresponding to different tissue types. The physical anatomical model may be representative of a shoulder joint including a portion of a humerus and shoulder, tendons of a rotator cuff, and muscle tissue.

FIGS. 24-25 illustrate another physical anatomical model 1160. The anatomical model 1160 may be established according to a configuration generated by the system 120 (FIG. 2), such as a configuration associated with the virtual anatomical model 429 and target and warning zones 448, 450 (FIG. 12). The anatomical model 1160 may include a main body 1160B establishing the target zone 1148 (FIG. 24) and one or more warning zones 1150 associated with the virtual anatomical model 429. The target zone 1148 and warning zones 1150 may cooperate to establish a construction representative of an anatomy. In implementations, the construction may be representative of a shoulder including a glenoid. The target zone 1148, warning zones 1150 and third zone 1154 (FIG. 25) may be established by the configuration associated with the virtual anatomical model 429.

The warning zones 1150 may be established adjacent to the target zone 1148. The warning zones 1150 and third zone 1154 may cooperate to bound the target zone 1148 in the physical anatomical model 1160. The target zone 1148 may correspond to the target zone 448. The warning zones 1150 may correspond to the respective warning zones 450. The third zone 1154 may correspond to the third zone 454. The configuration may be utilized to form target zone(s) 1148 assigned respective color(s) corresponding to natural color(s) of respective portion(s) of the anatomy. The configuration may be utilized to form warning zone(s) 1150 assigned respective artificial color(s) that establish a visual contrast with the natural color(s) associated with the target zone(s) 1148. Each warning zone 1150 may have a respective artificial color that may differ from a natural color of a respective portion of the anatomy.

The surgeon may perform one or more modifications to the physical anatomical model 1160. The surgeon may perform a reaming operation at various angles or orientations (different orientations illustrated in dashed lines in FIGS. 24-25) relative to an articulation surface 1160AS or another external surface of the anatomical model 1160. The articulation surface 1160AS may be representative of an articular surface of a bone, such as a glenoid face. The reaming operation may expose or reveal the target zone 1148 and/or one or more of the warning zones 1150. The target zone 1148 and warning zones 1150 may be formed of material having different moduli of elasticity such that the surgeon may be required to apply different amounts of pressure to ream through the material. In implementations, the target zone 1148 may have a modulus of elasticity that may be greater than a modulus of elasticity of one or more of the warning zones 1150. The moduli of elasticity of the warning zones 1150 may progressively decrease with respect to an offset of the respective warning zone 1150 from the target zone 1148.

FIGS. 26-27 are grayscale images of a physical anatomical model. The physical anatomical model may be representative of a shoulder sectioned along a glenoid. The sectioning may expose material representative of cortical and cancellous regions of bone. The material may include a warning zone established about a perimeter of the cancellous region.

FIG. 28 illustrates another assembly (e.g., training device) 1268. The assembly 1268 may incorporate a physical anatomical model 1260. The physical anatomical model 1260 may include a main body 1260B representative of an anatomy, such as a bone or joint.

The physical anatomical model 1260 may be configured to provide feedback associated with adjacent tissue including bone and nerve tissue. For older patients, over tensioning may occur when a joint is moved. The physical anatomical model 1260 may be configured to generate a snapping noise in response to interaction. In implementations, a particular portion of the physical anatomical model 1260 that may be representative bone may be configured to snap. This may occur for instance when the surgeon attempts to move the representative joint over a particular range of motion. For example, 8 mm of lateralization may be suitable for younger patients, but may not be suitable for older patients. During a shoulder repair, the surgeon may consider an axial nerve that extends about a humerus. The patient may experience numbness due to over-tensioning of the axial nerve (e.g., with use of a retractor).

Various techniques may be utilized to establish the snapping feature. At a predetermined force, deformation of soft tissue (e.g., muscle, nerve, etc.) or bony tissue may be permanent. A break line BL may be formed in the main body 1260B or another portion of the physical anatomical model 1260 (shown in dashed lines for illustrative purposes). The break line BL may be established by a notch, a reduction in material and/or a reduction in density.

The main body 1260B of the physical anatomical model 1260 may include one or more target zones 1248 and one or more warning zones 1250. A target zone 1248 may be established a distance from the indication member 1276 (shown in dashed lines for illustrative purposes). The indication member 1276 may serve as a target zone or may serve as a warning zone or indicator. The indication member 1276 may establish the target zone 1148 (indicated at 1148'). One or more warning zones 1250 may extend along the indication member 1276.

One or more indication members 1276 may be embedded in or may extend along the main body 1260B. The indication member 1276 may be representative of a nerve of the anatomy. The indication member 1276 may be configured to generate an indicator in response to meeting a predetermined criterion. The indication member 1276 may be configured to establish the snapping feature. The indication member 1276 may be formed by a flexible material such as an elastomer. The indication member 1276 may be configured to snap in response to stretching or tensioning the indication member 1276 above a predetermined limit.

In other implementations, the indication member 1276 may be a cable coupled to a gauge 1278, such as a strain gauge or an electronic circuit. The gauge 1278 may be responsive to tensioning the indication member 1276. The predetermined criterion may include a predefined threshold associated with tensioning the indication member 1276. The predefined threshold may be associated with an amount of force sufficient to cause permanent deformation of a representative nerve or snapping of a representative bone. The gauge 1278 may generate an audible signal (e.g., buzz) or visual signal (e.g., illumination of a light emitting diode) in response to the predefined threshold or other predetermined criterion being met, which may indicate that excessive tension may have been applied to the indication member 1276.

In implementations, the indication member 1276 may include an electrically conductive material such as an exposed wire or one or more layers of a metal or alloy. The indication member 1276 may be formed on a non-conductive material such as a plastic material. The main body 1260B may be printed or otherwise formed around a periphery of the indication member 1276, or the indication member 1276 may be inserted after the main body 1260B is formed. The indication member 1276 may be associated with an electrical signal. The indication member 1276 may be configured to establish the electrical signal in response to contact between the indication member 1276 and an electrically conductive device such as a metallic instrument. The indication member 1276 may have other configurations, such as suture sewn into the main body 1260B of the physical anatomical model 1260, etc.

FIG. 29 illustrates another physical anatomical model 1360. The physical anatomical model 1360 may be associated with a bone, such as a portion of a humerus. The physical anatomical model 1360 may be formed according to a configuration established by the system 120 (FIG. 2), such as a configuration associated with the virtual anatomical model 629 and related parameters, including the target and warning zones 648, 650 (see FIG. 14). The anatomical model 1360 may include portions 1362, 1364/1366. The portion 1362 may establish a main body 1360B and may be representative of bone tissue. The portion 1364/1364 may be formed on the portion 1362 and may include one or more fibers 1380. The fibers 1380 may be representative of soft tissue such as tendon, ligament or muscle tissue. Each fiber 1380 may include a core 1380C and sheath 1380S, which may be configured according to respective cores 656C and sheaths 656S of the fibers 656 (FIG. 14).

The cores 1380C may establish one or more warning zones 1350. One or more target zones 1348 may be established between adjacent fibers 1380. The target zones 1348 may be representative of a pathway between the adjacent fibers 1380. In implementations, the sheaths 1380S of the adjacent fibers 1380 may establish respective target zones 1348.

The surgeon may perform one or more modifications to the physical anatomical model 1360. The surgeon may separate the fibers 1380 along a reference plane REF4 and/or reference plane REFS with an instrument such as a scalpel. The reference plane REF4 may intersect one or more of the target zones 1348. The reference plane REFS may intersect with one or more of the warning zones 1350. Separating the fibers 1380 along reference plane REF4 may avoid exposing or revealing the warning zones 1350, as illustrated by the physical anatomical model 1360' of FIG. 30. Separating the fibers 1380' may represent separating or parting fibers of ligament, tendon or muscle tissue while leaving the fibers substantially intact. Separating the fibers 1380 along reference plane REFS may expose one or more of the warning zones 1350, as illustrated by the physical anatomical model 1360" of FIG. 31. Exposing or revealing the warning zones 1350" may represent cutting through fibers of ligament, tendon or muscle tissue.

In the implementation of FIG. 32, physical anatomical model 1460 may include one or more sheets 1482 formed on or otherwise arranged along a main body 1460B. The main body 1460B may establish a portion 1462. The sheets 1482 may establish respective portions 1464/1466. The sheets 1482 may establish respective target zones 1448 and/or warning zones 1450. The sheets 1482 may be arranged in various patterns to establish one or more target zones 1448 and warning zones 1450. In implementations, a set of the sheets 1482 may establish a column or row of target zones 1448. Adjacent sets of the sheets 1482 may establish columns or rows of warning zones 1450. Adjacent sets of the sheets 1482 may be arranged to establish warning zones 1450 offset at different distances from the target zone(s) 1448, as illustrated by warning zones 1450-1, 1450-2. The sheets 1482 may be made of any of the materials disclosed herein and may be relatively pliable.

Referring to FIG. 33, with continuing reference to FIG. 2, the system 120 may include a comparison to plan feature configured to provide feedback to the surgeon. The surgeon may perform one or more modifications to a physical anatomical model 1560. The physical anatomical model 1560 may have substantially the same geometry and construction as the physical anatomical model 1160, but may omit the target zone 1148 and warning zones 1150 (FIG. 25). The surgeon may perform a reaming operation (shown in dashed lines) on the model 1560, which may simulate resecting a portion of an articular surface of a glenoid. The resection may expose a first region R1 and second region R2. The first region R1 may be substantially solid. The second region R2 may be relatively porous. The first region R1 may be representative of cortical bone. The second region R2 may be representative of cancellous bone. In implementations of the anatomical model 1560, each of the first and second regions R1, R2 may have a color corresponding to a natural color of a respective portion of the anatomy.

One or more imaging devices 1584 (shown in dashed lines for illustrative purposes) may be configured to capture a geometry of the physical anatomical model 1560 and any modification(s) by the surgeon. The imaging device 1584 may include one or more cameras arranged in an array about the model 1560. The anatomical model 1560 may be scanned with the imaging device(s) 1584 and digitized into one or more digital images.

Referring to FIG. 34, with continuing reference to FIGS. 2 and 33, the spatial module 137 may be configured to generate one or more revised virtual anatomical models 1529 based on the digital images from the imaging device(s) 1584. The display module 136 may be configured to display the revised virtual anatomical model 1529 in display windows 1544-13, 1544-14 of the user interface 1542.

The comparison module 138 may be configured to compare the images and/or revised virtual anatomical model 1529 associated with the model 1560 to a surgical plan 131 to determine how accurately the surgical plan 131 was implemented by the surgeon utilizing the physical anatomical model 1560. The comparison module 138 may utilize various criteria to make the determination, such as trajectory and placement. In implementations, the comparison module 138 may cause the display module 136 to display portions of each target zone 1548, warning zone 1550 and/or third zone 1554 exposed by the modification(s) to the physical anatomical model 1560. The exposed target zone 1548 may be associated with the first region R1, and the exposed warning zone(s) 1550 may be associated with the second region R2 of the physical anatomical model 1560.

The comparison module 138 may be configured to compare one or more revisions of the physical anatomical model 1560 to an original virtual anatomical model 429 utilized to establish the configuration of the physical anatomical model 1560, including any established target and warning zones 448, 450 and other parameters (FIG. 12). The comparison module 138 may be configured to compare one or more revisions of the physical anatomical model 1560 as represented by the revised virtual anatomical model 1529 to the original virtual anatomical model 429.

The comparison module 138 may be configured to generate one or more indicators PI in the graphical user interface 1542 in response to the one or more revisions meeting predetermined threshold(s). Various indicators PI may be utilized, including textual and graphical indicators. A volume of the warning zones 1550 and offsets from the target zone 1548 may establish respective thresholds. The warning zones 1550 may be associated with respective visual indicators VI that establish the indicators PI. In implementations, the user interface 1542 may include graphic(s) 15461 that serve as indicator(s) PI.

In implementations, the surgeon may perform a surgical procedure on the physical anatomical model 1560 based on prior education or training that may be outdated. The system 120 may be configured to generate a training plan including materials associated with the respective outcome. The planning system 120 (FIG. 2) may be configured to present to the surgeon relatively more recent literature to educate the surgeon. The literature may be tailored or presented to the surgeon based on which of the warning zone(s) 1550 may be engaged by the surgeon. In implementations, a pop-up window may be generated in response to engaging a particular one of the warning zone 1550 (e.g., if the surgeon engages zone 1550-2). The surgeon, assistant or other user may interact with a button 1546B or another portion of the user interface 1542 to review the training materials. The surgeon may repeat a procedure utilizing another instance of the physical anatomical model 1560 to validate the training, including for a new technique or product.

The system 120 may be utilized to compare digitized outcomes for a group of surgeons. The system 120 may be utilized to generate instances of a common physical anatomical model associated with a common surgical plan 131. Modifications to the common physical anatomical models by the surgeons may be compared to validate or otherwise evaluate a surgical procedure, instrumentation, device, etc.

FIG. 35 illustrates another physical anatomical model 1660. The physical anatomical model 1660 may be a long bone, such as a tibia. The surgeon may perform one or more modifications to the physical anatomical model 1660. For example, the surgeon may perform a resection along reference plane REF6 on the model 1660 to remove a portion of material of the model 1660, which may simulate resecting a portion of an articular surface of the bone. Removing the material may establish a revised physical anatomical model 1660', as illustrated in FIG. 36. Imaging device(s) 1684 (shown in dashed lines for illustrative purposes) may be configured to capture a geometry of the physical anatomical model 1660' including any modifications.

Referring to FIG. 37, with continuing reference to FIGS. 2 and 35-36, a revised virtual anatomical model 1629 may be generated based on digital image(s) from the imaging device(s) 1684. The display module 136 may be configured to display the revised virtual anatomical model 1629 in a display window 1644-16 and an associated original virtual anatomical model 129 in a display window 1644-15. The comparison module 138 may be configured to compare the images and/or revised virtual anatomical model 1629 associated with the revised physical anatomical model 1660' to the original virtual anatomical model 129 of a surgical plan 131 to determine how accurately the surgical plan 131 was implemented by the surgeon utilizing the physical anatomical model 1660. The comparison module 138 may be configured to compare one or more revisions of the physical anatomical model 1660 to the original virtual anatomical model 129 utilized to establish the configuration of the physical anatomical model 1660, including a specified reference plane REFI and/or other parameters.

The comparison module 138 may be configured to compare the revised physical anatomical model 1660', as represented by the virtual anatomical model 1629, to a predetermined geometry of the associated virtual anatomical model 129. In implementations, the reference plane REF7 may represent a planned resection plane with respect to a longitudinal axis A of the virtual anatomical model 129. The reference plane REF7 may establish an angle α relative to the longitudinal axis A. The reference plane REF6 may represent an actual resection plane formed by the resection to the physical anatomical model 1660. The reference plane REF6 may establish an angle β relative to the longitudinal axis A. Angles α, β may be referred to as a "varus/valgus angle" or may be referenced with respect to a "posterior slope" for a proximal tibia, distal femur, distal humerus, etc. Angles α, β may be referred to as a "caput-collum-diaphyseal (CCD) angle" or "neck shaft angle" for a proximal femur, humeral head, etc. The comparison module 138 may be configured to determine a difference between the angles α, β. The comparison module 138 may be configured to generate an indicator PI in response to the removed portion of the physical anatomical model 1660 meeting a predetermined threshold. In implementations, a first predetermined threshold may be a difference between the angles α, β being greater than 3 percent, absolute. More than one predetermined threshold may be utilized. In implementations, a second predetermined threshold may be a difference between the angles α, β being greater than 5 percent, absolute.

Indicators PI may include one or more graphics 16461, 1646G. Graphic 1646G may be configured to display a value of the difference between the angles α, β. Graphic 16461 may be configured to indicate whether or not the difference between the angles α, β exceeds the predetermined threshold(s).

FIG. 38 illustrates a training assembly 1786 for a surgical procedure. The training assembly 1786 may include a measurement device 1788 configured to compare one or more revisions of a physical anatomical model 1760 to a virtual anatomical model 129 (FIG. 2) utilized to establish a configuration of the physical anatomical model 1760, including any of the parameters disclosed herein.

The measurement device 1788 may include a base 1789, a tower 1790 and an outrigger 1791. The tower 1790 may extend in a first (e.g., vertical) direction Y from the base 1789. The outrigger 1791 may extend laterally in a second (e.g., horizontal) direction X from the tower 1790. The outrigger 1791 may include a ruler 1792 situated over a predetermined position P along the base 1789. The ruler 1792 may be suspended from the outrigger 1791 over the base 1789 at a predetermined position. The ruler 1792 and/or outrigger 1791 may be moveable relative to the base 1789 and tower 1790. The base 1789 may be positioned on a table top or another static structure.

The physical anatomical model 1760 may include a main body 1760B having a construction representative of an anatomy. The main body 1760B may extend between a first end portion 1760A and a second end portion 1760C.

One or more markers (e.g., indicators) M may be formed along surfaces of the anatomical model 1760 for positioning the model 1760 relative to the device 1788. Each marker M may be established at a predetermined position and orientation relative to an axis A of the model 1760. The markers M may include first and second markers M1, M2. The first marker M1 may be formed along the first end portion 1760A of the model 1760. The second marker M2 may be formed along the second end portion 1760C of the model 1760. The first marker M1 may be substantially aligned with the predetermined position P such that the second marker M2 may be aligned with a position along the ruler 1792.

The base 1789 may be dimensioned to support a resected surface 1760R along the first end portion 1760A of the main body 1760B at the predetermined position P such that the marker M2 may be aligned with a position along ruler 1792. The resected portion of the main body 1760B may include a first region representative of cortical bone of the anatomy and a second region representative of cancellous bone of the anatomy (see, e.g., FIG. 21). In implementations, the first end portion 1760A may include the first region and/or second region. The first region may include at least one warning zone that may have an artificial color that differs from a natural color of a respective portion of the anatomy (see, e.g., FIG. 33).

The ruler 1792 may include indicia 17921. Each position along the ruler 1792 established by the indicia 17921 may be associated with a respective angle relative an axis L of the device 1788. The axis L may extend in the first direction Y from the predetermined position P. The axis L may extend through, and may be substantially perpendicular to, the predetermined position P.

The surgeon may evaluate an angle β established between the resected surface 1760R and an axis A of the model 1760 based on a position of the marker M2 relative to the indicia 17921. For example, the angle β may be less than an angle β associated with a resected surface 1760R' of the physical anatomical model 1760' of FIG. 39. The device 1788 may serve to provide the surgeon with feedback regarding the angle β formed by the resection without evaluating the resection with an imaging device. The surgeon may make one or more additional modifications to the model 1760 to establish a new resected surface 1760R and then may evaluate changes in the associated angle β.

FIG. 40 illustrates an exemplary method of planning and performing a surgical procedure in a flowchart 1894. The method 1894 may be utilized to pre-operatively plan, rehearse and/or train for various surgical procedures, such as an arthroplasty for restoring functionality to shoulders, ankles, knees, hips and other joints having advanced cartilage disease. The method 1894 may be utilized with any of the planning systems and virtual and physical anatomical models disclosed herein. The method 1894 may be utilized to evaluate the accuracy in which a surgeon implements a surgical procedure on a physical anatomical model associated with an anatomy of a patient. Fewer or additional steps than are recited below could be performed within the scope of this disclosure, and the recited order of steps is not intended to limit this disclosure. Reference is made to the system 120 and user interface 142 for illustrative purposes.

Referring to FIG. 2, with continuing reference to FIG. 40, at step 1894-1 one or more virtual anatomical models 129 may be generated. Each virtual anatomical model 129 may be associated with an anatomy of a patient and may be generated utilizing any of the techniques disclosed herein.

Referring to FIG. 3, with continuing reference to FIGS. 2 and 36, at step 1894-2 one or more virtual anatomical models 129 may be selected from a set of virtual anatomical models 129. The virtual anatomical models 129 may be stored in memory of a computing device, such as in the database 128 or the memory 134 of the computing device 132. Selecting the virtual anatomical model 129 may include selecting from various parameters associated with the set of virtual anatomical models 129. The parameters may include any of the parameters disclosed herein, including patient classification and defect category. The parameters may be selected in response to user interaction with the graphical user interface 142. The virtual anatomical models 129 may include any of the anatomies and tissue types disclosed herein, including bone, ligament, tendon, cartilage, etc. Referring to FIG. 5, with continuing reference to FIGS. 2 and 40, at step 1894-3 the selected virtual anatomical model(s) 129 may be viewed in the graphical user interface 142.

Referring to FIG. 6, with continuing reference to FIGS. 2 and 40, at step 1894-4 one or more implant models 130 may be selected and positioned relative to the selected virtual anatomical model(s) 129. Each implant model 130 may be selected from a set of implant models 130. The implant models 130 may be stored in memory of a computing device, such as in the database 128 or the memory 134 of the computing device 132. The implant models 130 may be associated with any of the implants disclosed herein.

At step 1894-5, aspects of one or more of the virtual anatomical models 129 may be defined. Each virtual anatomical model 129 may be defined prior, during and/or subsequent to generating the virtual anatomical model 129 at step 1894-1 and/or selecting the virtual anatomical model 129 at step 1894-2. Defining the virtual anatomical model 129 may include setting one or more parameters of the virtual anatomical model 129, including any of the parameters disclosed herein. The parameters may be selected in response to user interaction with the graphical user interface 142, as illustrated by FIGS. 7-8. The parameters may be associated with one or more target zones 148 and/or warning zones 150 (FIG. 8).

Step 1894-5 may include establishing one or more target zones at step 1894-5A, as illustrated by the target zone 148 of FIG. 7. Step 1894-5 may include establishing one or more warning zones at step 1894-5B, as illustrated by the warning zones 150 of FIG. 8. The target zone(s) 148 and warning zone(s) 150 may be established utilizing any of the techniques disclosed herein, including any of the disclosed geometries, arrangements, and visual contrast and color schemes.

At step 1894-6, one or more configurations (e.g., definitions) may be generated. Each configuration may be associated with a physical anatomical model and may be generated utilizing any of the techniques disclosed herein. The configuration may be representative of the selected virtual anatomical model 129. Each configuration may be generated in response to selecting the respective virtual anatomical model 129 at step 1894-2 and/or defining the selected virtual anatomical model 129 at step 1894-5. The configuration may be established according to the selection or specification of any parameters associated with the selected virtual anatomical model 129, including any target zones 148 and warning zones 150 (see, e.g., FIGS. 7-8). The configuration may include data and other information sufficient to establish a physical anatomical model based on the parameters of the selected virtual anatomical model 129, including coordinate information, moduli of elasticity of the associated tissues, color schemes associated with target zones and warning zones, etc.

At step 1894-7, one or more physical anatomical models may be fabricated or otherwise formed based on the generated configuration. Each physical anatomical model may be formed utilizing any of the techniques disclosed herein. In the implementation of FIG. 41, one or more layers 1895 of material are printed or otherwise formed on a substrate 1896 to establish a physical anatomical model 1860. The physical anatomical model 1860 may be representative of a virtual anatomical model. A device 1897 such as a three-dimensional printer may be configured to form the layers 1895 according to data and other information associated with the respective configuration (shown in dashed lines for illustrative purposes). The layers 1895 of material may include any of the any of constructions, materials, coloring, textures, porosities, etc. disclosed herein. The layers 1895 may have respective moduli of elasticity that substantially correspond to moduli of elasticity of respective biomaterial of the anatomy.

The porosities of the material forming the physical anatomical model 1860 may substantially approximate the porosity or density of the respective tissue. In implementations, the porosities may be tailored or changed for certain techniques. The density may be varied independent of anatomic size and/or pathology. Poor bone density represented by a physical anatomical model may prompt the surgeon to select a particular implant for imbedding in the bone. If the surgeon resects a physical anatomical model of a humeral head, the surgeon may obtain a visual or tactile response by feeling the softness of the representative bone and seeing the darkness of the representative bone that may likely to be represented in a scanned image. If the surgeon selects a stemless device for implantation in bone with poor bone density, the surgeon may understand why the selection may not be beneficial through observation of the modified physical anatomical model. The feedback may cause the surgeon to select a stem-based device based on bone quality. In another training session, the surgeon may be presented with a physical anatomical model representative of relatively more dense bone. The surgeon may feel a surface representative of resected bone and based on feeling the surgeon may determine that the representative bone is relatively more dense, which may prompt the surgeon to select a stemless implant.

Utilizing the techniques disclosed herein, the surgeon may have an opportunity to make implant selections based on feeling and visualize of the physical anatomical model.

Step 1894-7 may include forming the layers 1895 of material to establish the physical anatomical model 1860. The layers 1895 may be formed concurrently and/or sequentially. Each layer 1895 may be homogenous or heterogenous. Heterogenous layers may incorporate different regions associated with respective tissue types, densities, porosities, colors, etc. Step 1894-7 may include printing the layers 1895 of material on each other to establish one or more target zones and/or warning zones bounding the target zone(s), as illustrated by the target zone 1148 and warning zones 1150 of the physical anatomical model 1160 of FIG. 25. The warning zones 1150 may be formed in stacked relationship such that the warning zones 1150 are offset at different distances from the target zone 1148. Layers 1195 may be formed such that the warning zones 1150 may substantially encircle the target zone 1148. The target zones and warning zones may be formed to establish any of the color schemes, visual contrasts and other indicators disclosed herein. Each target zone may have a color that may correspond to a natural color of a respective portion of the anatomy. Each warning zone may have a respective artificial color that may establish a visual contrast with the natural color associated with the target zone, as illustrated by the target zone 1148 and warning zones 1150. The artificial colors of the warning zones may differ from each other to establish a visual contrast, also as illustrated by the target zone 1148 and warning zones 1150.

In other implementations, step 1894-7 may include forming one or more fibers, which may be arranged in bundles, as illustrated by the portions 964, 966 and associated fibers of FIG. 18.

At step 1894-8, the physical anatomical model may be positioned or otherwise prepared. As illustrated by FIG. 18, the physical anatomical model 960 may be secured to one or more fixtures 970 to establish an assembly 968.

At step 1894-9, one or more modifications to the physical anatomical model(s) may be performed. Step 1894-9 may include removing a portion of the physical anatomical model to establish a revised physical anatomical model. Various modifications may be performed to simulate surgical operations performed on an anatomy, including any of the modifications disclosed herein such as one or more incision, cutting, drilling, reaming, resection and implantation operations (see, e.g., FIGS. 20-21). Each modification may result in permanently altering a geometry of the physical anatomical model. Step 1894-9 may include removing a portion of the physical anatomical model to expose one or more warning zones, as illustrated by the physical anatomical model 1160 of FIGS. 24-25 and physical anatomical model 1360" of FIG. 31 (see also FIGS. 26-27).

At step 1894-10, modification(s) to the physical anatomical model(s) may be evaluated utilizing any of the techniques disclosed herein. Step 1894-10 may include generated a virtual anatomical model based on the revised physical anatomical model, as illustrated by the physical model 1560 of FIG. 32 and the revised virtual model 1529 of FIG. 34 (see also models 1660' and 1629 of FIGS. 36-37). Step 1894-10 may include comparing the revised physical anatomical model(s) to a predetermined geometry of the virtual anatomical model(s), as illustrated by FIGS. 34 and 37. Step 1894-10 may include generating one or more indicators at step 1894-10A, including any of the indicators disclosed herein. The indicator(s) may be generate in response to the removed portion of the physical anatomical model meeting any of the predetermined criteria disclosed herein, such as one or more predetermined thresholds, as illustrated in FIGS. 34 and 37. Evaluating the modification(s) to the physical anatomical model may include positioning the revised physical anatomical model relative to the measurement device 1788 of FIG. 37.

The novel devices and methods of this disclosure provide versatility in planning, rehearsing and training for surgical procedures utilizing physical anatomical models. The physical anatomical models may be representative of various anatomy, including anatomy associated with various classifications and defects. The surgeon may interact with the disclosed system to gain familiarity with the selected anatomy and various surgical procedures that may be utilized to implement a surgical plan. The physical anatomical models may be representative of various tissue types and may incorporate one or more indicators including target and warning zones. The indicators may assist the surgeon in determining the accuracy of implementing surgical procedures on the physical anatomical model.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A physical anatomical model comprising:
    a main body including a target zone and one or more warning zones adjacent to the target zone that cooperate to establish a construction representative of an anatomy;
    wherein the target zone has a property associated with a respective portion of the anatomy; and
    wherein each warning zone has a property that differs from a natural property of a respective portion of the anatomy and that differs from the property of the target zone.

2. The physical anatomical model as recited in claim 1, wherein the property of the target zone includes a color that corresponds to a natural color of the respective portion of the anatomy, the property of each warning zone includes a respective artificial color that differs from a natural color of the respective portion of the anatomy and that establishes a visual contrast with the natural color associated with the target zone, the one or more warning zones are a plurality of warning zones corresponding to a plurality of layers in stacked relationship, and the artificial colors of the layers differ from each other.

3. The physical anatomical model as recited in claim 2, wherein the plurality of layers substantially encircle the target zone.

4. The physical anatomical model as recited in claim 3, wherein the target zone has a truncated conical geometry having a base establishing an entry point along an external surface of the main body.

5. The physical anatomical model as recited in claim 2, wherein the plurality of layers are offset at different depths from an external surface of the main body.

6. The physical anatomical model as recited in claim 5, wherein:
    the target zone establishes the external surface and is representative of cortical bone associated with the anatomy;
    the main body includes a third zone representative of cancellous bone associated with the anatomy; and
    the plurality of layers are arranged such that the warning zones are established between the target zone and the third zone.

7. The physical anatomical model as recited in claim 2, wherein the plurality of layers includes a first set of layers and a second set of layers, and the target zone is established between the first and second sets of layers.

8. The physical anatomical model as recited in claim 1, wherein the target zone extends inwardly from an external surface of the main body, and the one or more warning zones are established below the external surface.

9. The physical anatomical model as recited in claim 1, wherein the target zone and the one or more warning zones are representative of bone tissue associated with the anatomy.

10. The physical anatomical model as recited in claim 1, wherein:

the target zone and the one or more warning zones are representative of soft tissue associated with the anatomy;

the soft tissue includes muscle tissue; and the main body includes a bundle of fibers representative of the muscle tissue, one or more of the fibers establishes a respective one of the warning zones, and the target zone is established between an adjacent pair of the fibers.

11. The physical anatomical model as recited in claim 10, wherein each of the fibers comprises an elastomeric material.

12. The physical anatomical model as recited in claim 10, wherein:

the bundle of fibers include a first set of fibers and a second set of fibers, the first set of fibers establish the target zone, and each fiber of the second set of fibers establishes a respective one of the warning zones.

13. The physical anatomical model as recited in claim 10, wherein:

each of the fibers include a core and an outer sheath surrounding the core; and the core establishes a respective one of the warning zones.

14. The physical anatomical model as recited in claim 1, wherein the construction is representative of a glenoid.

15. A method of rehearsing for a surgical procedure comprising:

defining a virtual anatomical model associated with an anatomy; and forming a plurality of layers of material to establish a physical anatomical model representative of the virtual anatomical model, wherein the layers of material establish a target zone and one or more warning zones bounding the target zone, the target zone has a color that corresponds to a natural color of a respective portion of the anatomy, and each warning zone has a respective artificial color that establishes a visual contrast with the natural color associated with the target zone.

16. The method as recited in claim 15, wherein:

selecting the virtual anatomical model from a plurality of virtual anatomical models stored in memory of a computing device; and the step of selecting the virtual anatomical model includes selecting from a patient classification and selecting from a defect category in response to user interaction with a graphical user interface.

17. The method as recited in claim 15, wherein:

the forming step includes printing the layers of material on each other to establish the target zone and the one or more warning zones; and the layers of material have respective moduli of elasticity that substantially correspond to moduli of elasticity of respective portions of the anatomy.

18. The method as recited in claim 15, wherein:

the one or more warning zones include a plurality of warning zones in stacked relationship such that the warning zones are offset at different distances from the target zone, and the artificial colors of the warning zones differ from each other to establish a visual contrast; and the forming step occurs such that the warning zones encircle the target zone.

19. The method as recited in claim 15, further comprising:

removing a portion of the physical anatomical model to expose the one or more warning zones.

* * * * *